(12) United States Patent
Araki et al.

(10) Patent No.: US 10,988,494 B2
(45) Date of Patent: Apr. 27, 2021

(54) EUROPIUM COMPLEX

(71) Applicants: TOSOH CORPORATION, Shunan (JP); SAGAMI CHEMICAL RESEARCH INSTITUTE, Ayase (JP)

(72) Inventors: Keisuke Araki, Ayase (JP); Hiroya Honda, Ayase (JP); Naoyuki Koiso, Ayase (JP); Ryo Nakagame, Ayase (JP); Fumiaki Yoshitomi, Ayase (JP); Kohei Iwanaga, Ayase (JP); Taishi Furukawa, Ayase (JP)

(73) Assignees: TOSOH CORPORATION, Shunan (JP); SAGAMI CHEMICAL RESEARCH INSTITUTE, Ayase (JP)

( * ) Notice: Subject to any disclaimer, the term of this patent is extended or adjusted under 35 U.S.C. 154(b) by 0 days.

(21) Appl. No.: 16/766,015

(22) PCT Filed: Nov. 27, 2018

(86) PCT No.: PCT/JP2018/043579
§ 371 (c)(1),
(2) Date: May 21, 2020

(87) PCT Pub. No.: WO2019/103155
PCT Pub. Date: May 31, 2019

(65) Prior Publication Data
US 2020/0354389 A1 Nov. 12, 2020

(30) Foreign Application Priority Data
Nov. 27, 2017 (JP) .............................. JP2017-227187
Mar. 20, 2018 (JP) .............................. JP2018-052956

(51) Int. Cl.
C07F 15/00 (2006.01)

(52) U.S. Cl.
CPC .................................. C07F 15/00 (2013.01)

(58) Field of Classification Search
CPC ...................................................... C07F 15/00
See application file for complete search history.

(56) References Cited

U.S. PATENT DOCUMENTS

| | | | | |
|---|---|---|---|---|
| 3,377,292 A | * | 4/1968 | Halverson ............... | C09K 11/06 252/301.18 |
| 10,399,999 B2 | * | 9/2019 | Hasegawa ............... | C09K 11/06 |

(Continued)

FOREIGN PATENT DOCUMENTS

| | | |
|---|---|---|
| CN | 103936777 | 7/2014 |
| JP | 2003-81986 | 3/2003 |

(Continued)

OTHER PUBLICATIONS

Y. Hasegawa et al., 119 The Journal of Physical Chemistry A, 4825-4833 (2015) (Year: 2015).*

(Continued)

Primary Examiner — Alexander R Pagano
(74) Attorney, Agent, or Firm — Nixon & Vanderhye PC

(57) ABSTRACT

To provide europium complexes having high photostability. A europium complex expressed with the following formula (A):

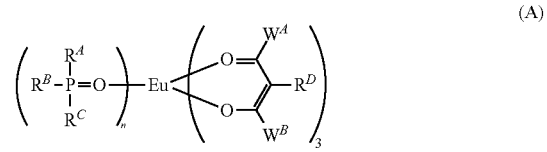

(A)

{wherein, $R^A$ and $R^B$ are independently a cyclic alkyl group with 3 to 10 carbons, respectively, and $R^C$ is a cyclic alkyl group with 3 to 10 carbons or a phenyl group expressed with the following formula (B):

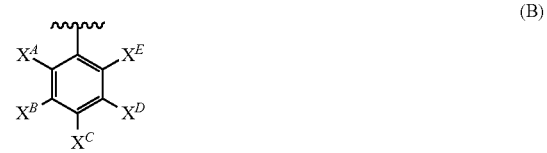

(B)

(wherein, $X^A$, $X^B$, $A^C$, $X^D$ and $X^E$ independently represent a hydrogen atom; a fluorine atom; an alkyl group with 1 to 3 carbon(s); an alkyloxy group with 1 to 3 carbon(s); an aryloxy group with 6 to 10 carbons; a fluoroalkyl group with 1 to 3 carbon(s); a fluoroalkyloxy group with 1 to 3 carbon(s); or a phenyl group that may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group or a cyano group, respectively);
$R^A$ is a cyclic alkyl group with 3 to 10 carbons;
$R^B$ and $R^C$ are a phenyl group expressed with the formula (B), provided, however, that a case where $R^A$ a cyclohexyl group, and, $R^B$ and $R^C$ are a phenyl group is excluded; or $R^A$, $R^B$ and $R^C$ independently represent an ortho-substituted phenyl group expressed with the following formula (Ba):

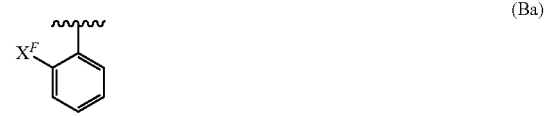

(Ba)

(wherein, $X^E$ represents a hydrogen atom, an alkyl group with 1 to 3 carbon(s), an alkyloxy group with 1 to 3 carbon(s), a fluoroalkyl group with 1 to 3 carbon(s), a (Continued)

fluoroalkyloxy group with 1 to 3 carbon(s), a naphthyl group that may be substituted with a fluorine atom, a pyridyl group that may be substituted with a fluorine atom, or a phenyl group that is expressed with a formula (C):

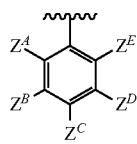

(C)

[wherein, $Z^A$, $Z^C$ and $Z^E$ independently represent a hydrogen atom, a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a phenyl group that may be substituted with a fluorine atom, a hydroxyl group or a cyano group; $Z^B$ and $Z^D$ independently represent a hydrogen atom or a fluorine atom, respectively], provided, however, that a case where $R^A$, $R^B$ and $R^C$ are all a phenyl group is excluded), respectively; $R^D$ represents a hydrogen atom, a deuterium atom or a fluorine atom; $W^A$ and $W^B$ independently represent an alkyl group with 1 to 6 carbon(s), a fluoroalkyl group with 1 to 6 carbon(s), a phenyl group, a 2-thienyl group or a 3-thienyl group; and 'n' represents an integer of 1 to 3}.

19 Claims, 25 Drawing Sheets

(56) References Cited

U.S. PATENT DOCUMENTS

| | | | |
|---|---|---|---|
| 10,745,614 B2 * | 8/2020 | Nakanishi | C07F 9/65515 |
| 2007/0273274 A1 * | 11/2007 | Horiuchi | F21K 9/64 |
| | | | 313/504 |
| 2009/0224048 A1 * | 9/2009 | Hasegawa | C09K 11/06 |
| | | | 235/454 |
| 2012/0140439 A1 | 6/2012 | Hasegawa et al. | |
| 2014/0106270 A1 * | 4/2014 | Takamiya | G03G 9/0817 |
| | | | 430/105 |
| 2014/0171600 A1 * | 6/2014 | Hasegawa | C08G 83/001 |
| | | | 525/538 |
| 2015/0280037 A1 * | 10/2015 | Kataoka | B32B 17/10669 |
| | | | 136/257 |
| 2016/0160121 A1 * | 6/2016 | Hasegawa | C07F 9/6521 |
| | | | 534/15 |
| 2017/0121597 A1 * | 5/2017 | Kataoka | C09K 11/06 |
| 2017/0130035 A1 * | 5/2017 | Kataoka | C08K 9/10 |
| 2020/0063030 A1 * | 2/2020 | Kitagawa | C07C 49/323 |

FOREIGN PATENT DOCUMENTS

| | | |
|---|---|---|
| JP | 2005-223276 | 8/2005 |
| JP | 2014-197144 | 10/2014 |
| RU | 1 453 860 | 4/1996 |
| WO | WO 2011/013520 | 2/2011 |

OTHER PUBLICATIONS

S. Miyazaki et al., 124 The Journal of Physical Chemistry A, 6601-6606 (2020) (Year: 2020).*
W. Quirino et al., 515 Thin Solid Films, 927-931 (2006) (Year: 2006).*
H. Kawai et al., 581 Molecular Crystals and Liquid Crystals, 95-100 (2013) (Year: 2013).*
International Search Report issued in PCT/JP2018/043579 dated Feb. 5, 2019.
Knyazev et al., "Influence of Lewis Bases on the Mesogenic and Luminescent Properties of Homogeneous Films of Europium(III) Tris (β-diketonate) Adducts" *European Journal of Inorganic Chemistry*, vol. 2017, No. 3, p. 639-645, ISSN 1434-1948 (Jan. 18, 2017).
Proceedings of the 98th CSJ Annual Meeting (2018), *The Chemical Society of Japan*, 2PA-194.
Summary of Lectures at the 36th Inorganic Polymer Workshop, *The Society of Polymer Science*, Japan, 2017, p. 47.
Zairov et al., "Nanoparticles based on gadolinium(III) and europium(III) complexes for biovisualization" *Russian Chemical Bulletin, International Edition*, vol. 65, No. 5, p. 1325-1331, ISSN 1066-5285 (May 2016).
Zairov et al., "Polymethoxyphenyl-Substituted [2-(5-Chloro-2-hydroxy-4-methylphenyl)-2-phenylvinyl]phosphine Oxides: Synthesis and Complexation with Eu(TTA)$_3$", *Russian Journal of Organic Chemistry*, 2014, vol. 50, No. 4, p. 547-551, ISSN 1070-4280.

* cited by examiner

[FIG. 1]
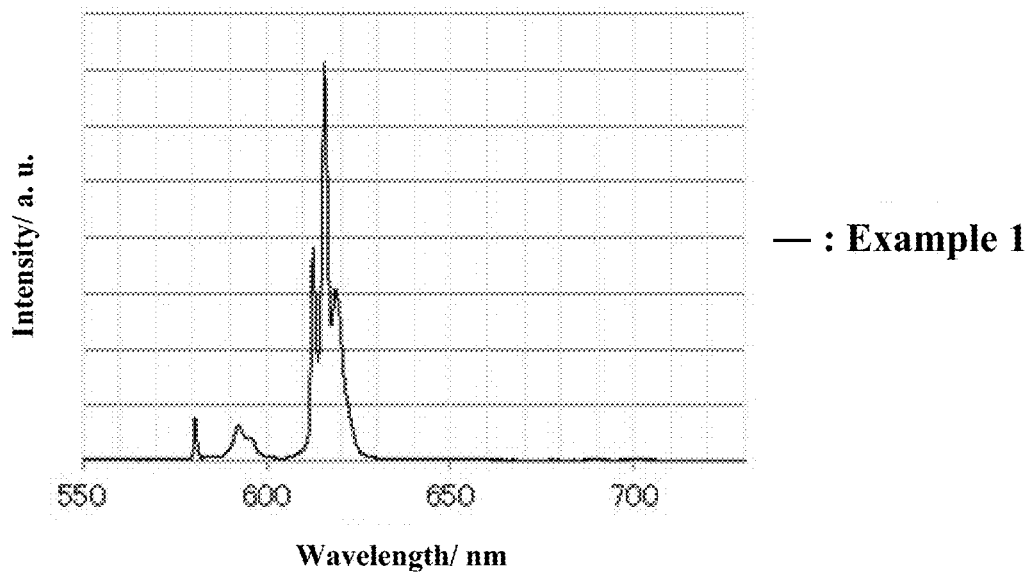
— : Example 1
[FIG. 2]
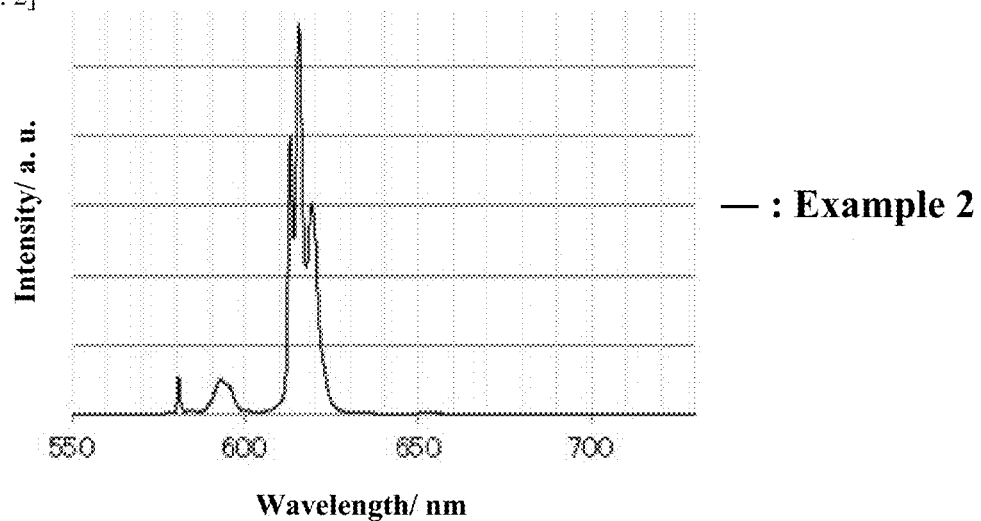
— : Example 2

[FIG. 3]
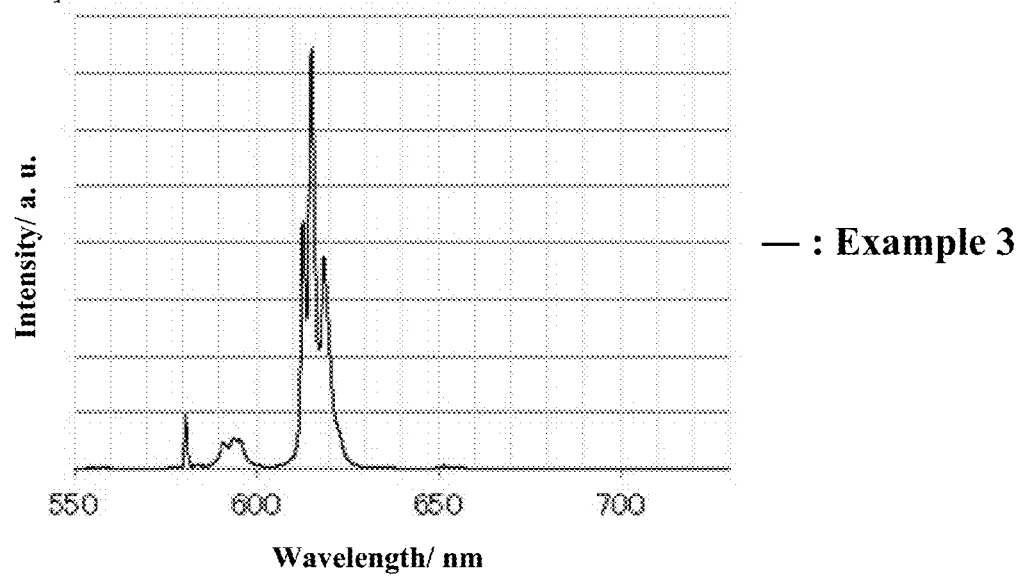
— : Example 3
[FIG. 4]
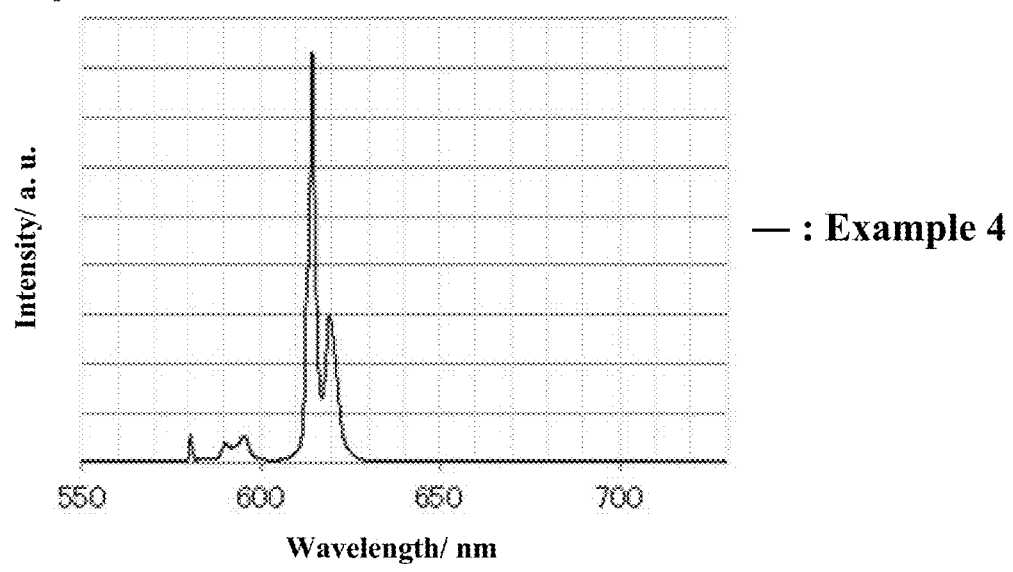
— : Example 4

[FIG. 5]
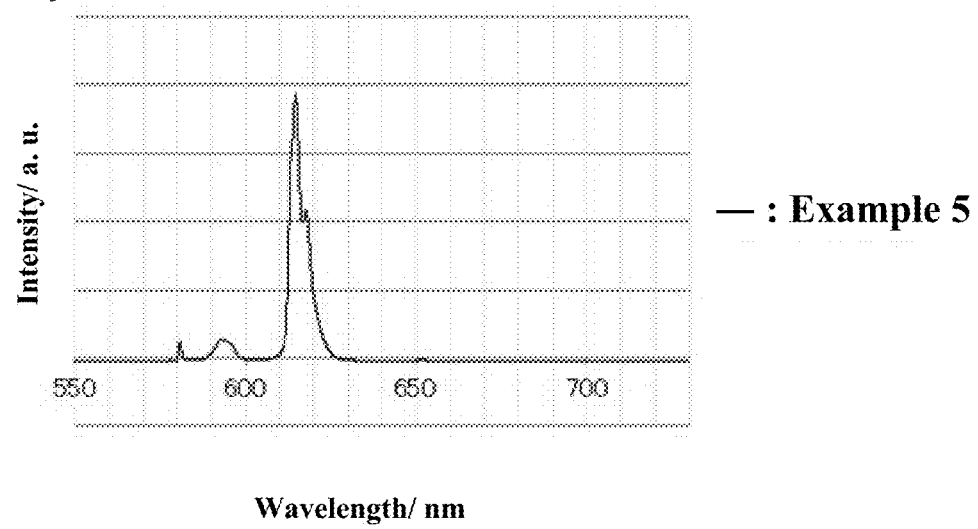
— : Example 5
Wavelength/ nm
[FIG. 6]
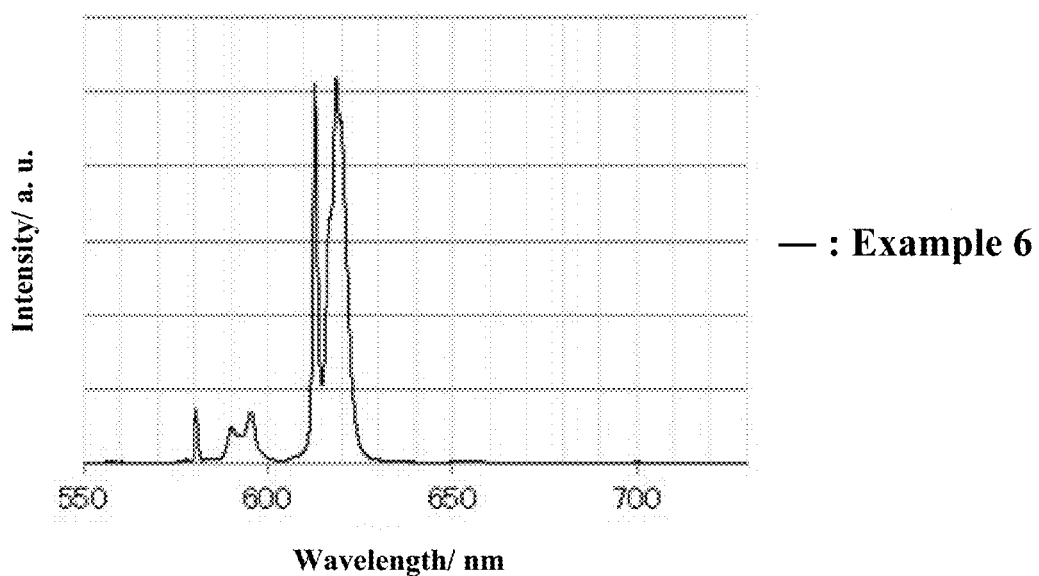
— : Example 6
Wavelength/ nm

[FIG. 7]
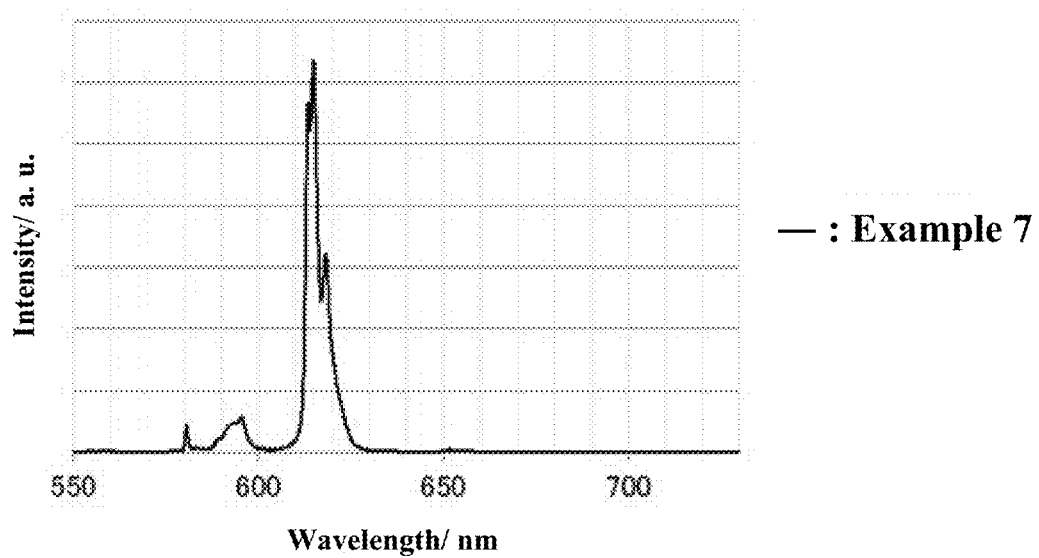
— : Example 7
[FIG. 8]
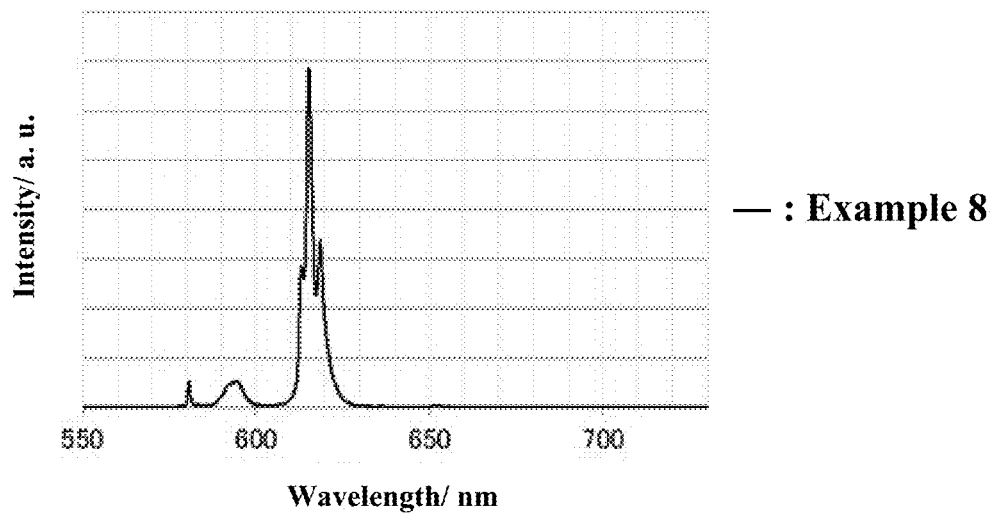
— : Example 8

[FIG. 9]
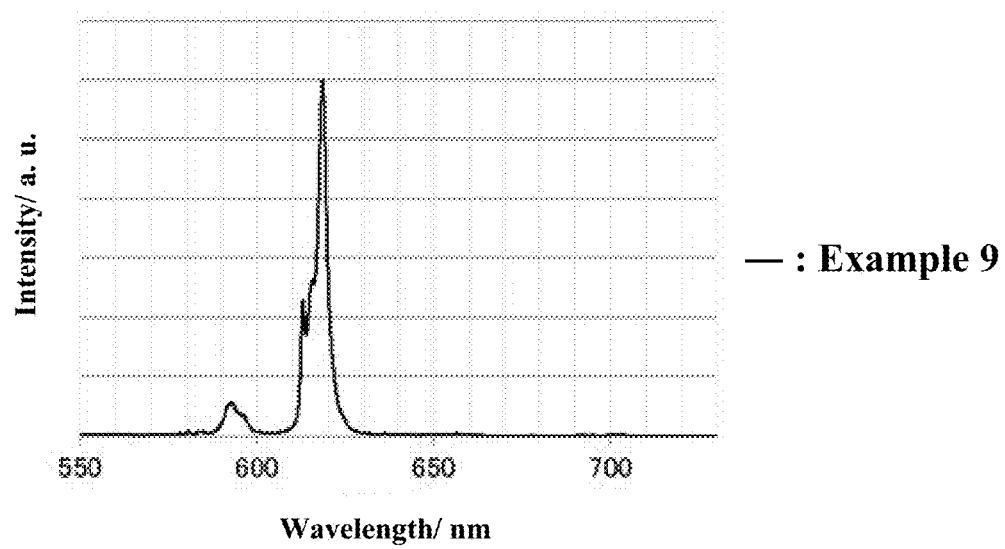
— : Example 9
[FIG. 10]
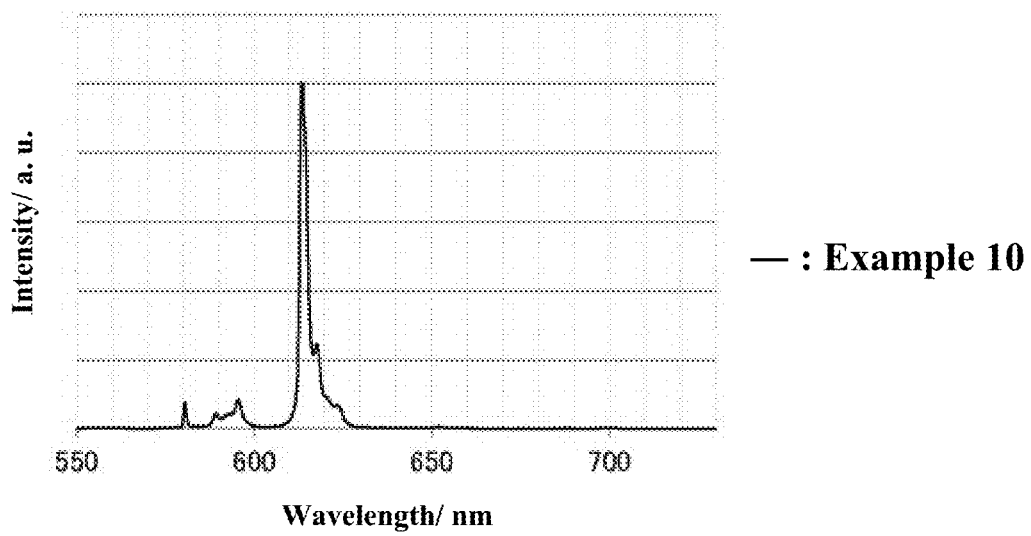
— : Example 10

[FIG. 11]
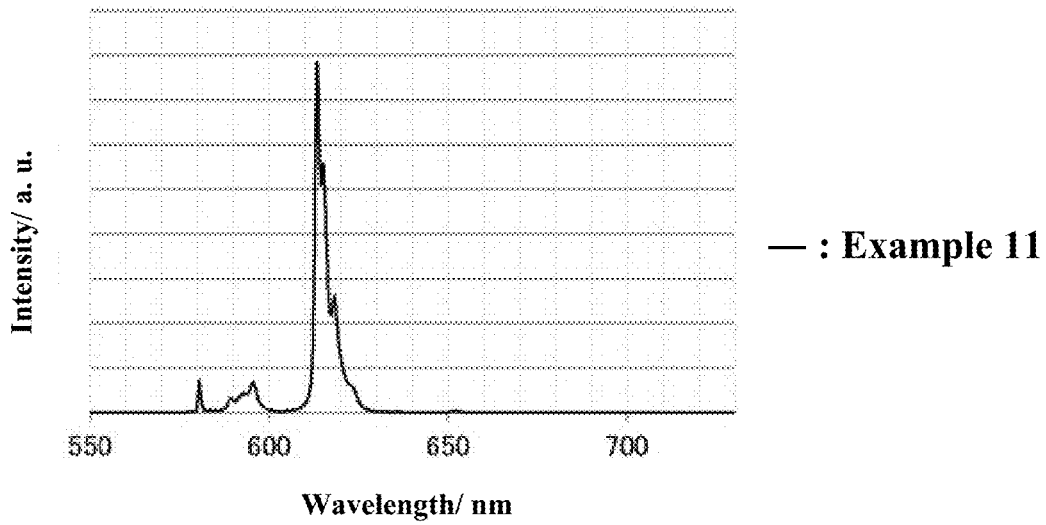
— : Example 11
[FIG. 12]
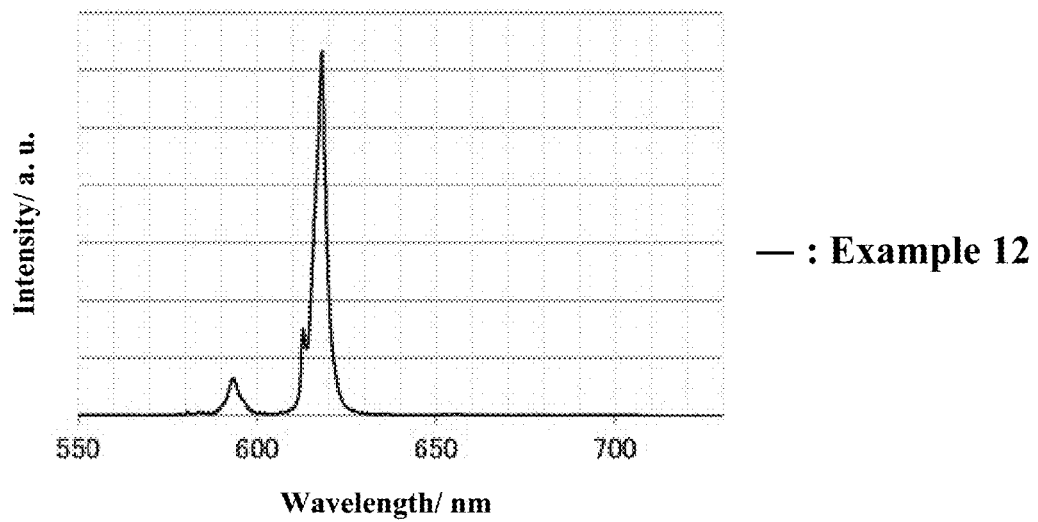
— : Example 12

[FIG. 13]
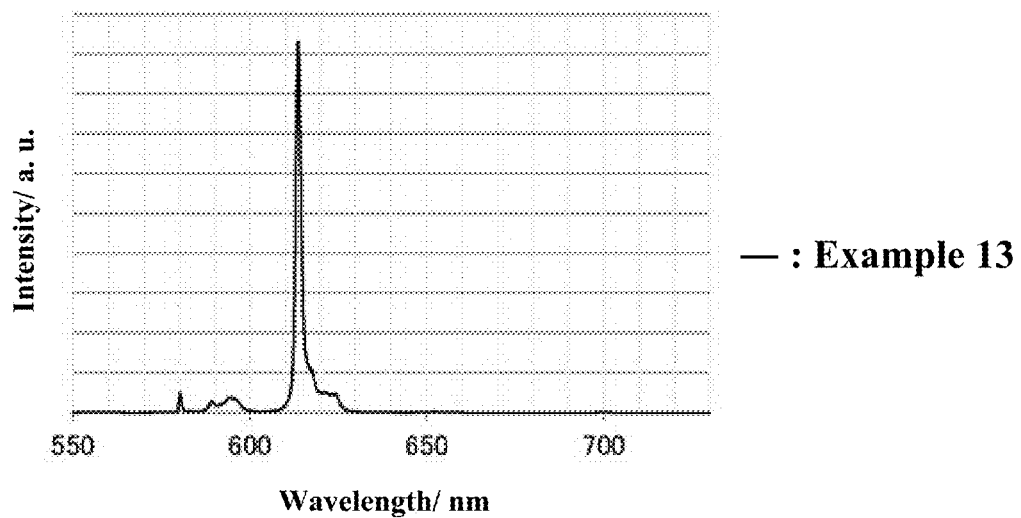
— : Example 13
[FIG. 14]
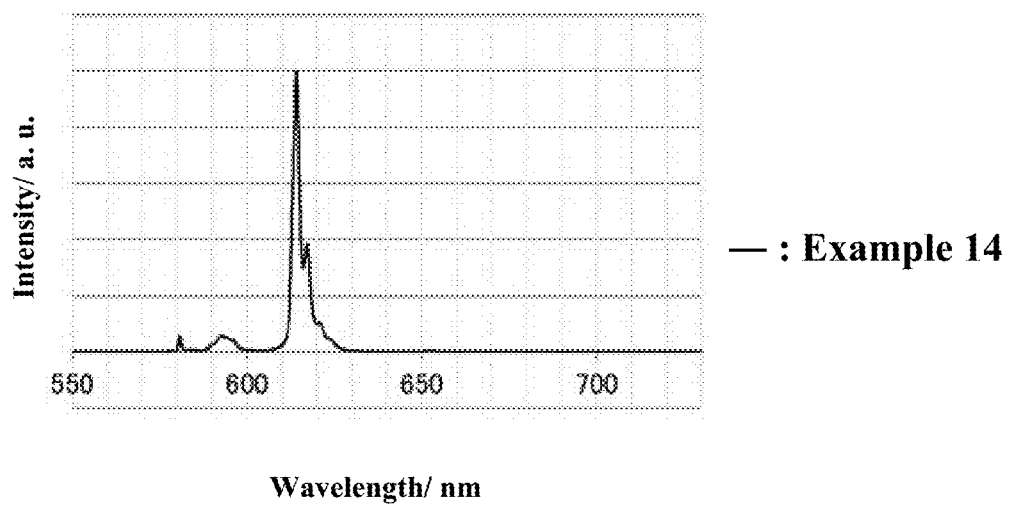
— : Example 14

[FIG. 15]
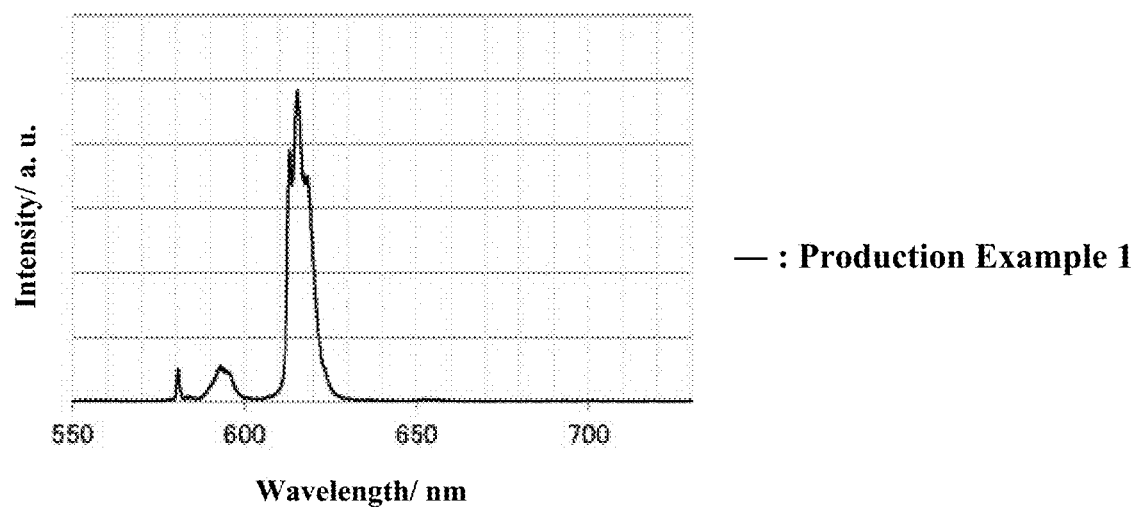
— : Production Example 1
[FIG. 16]
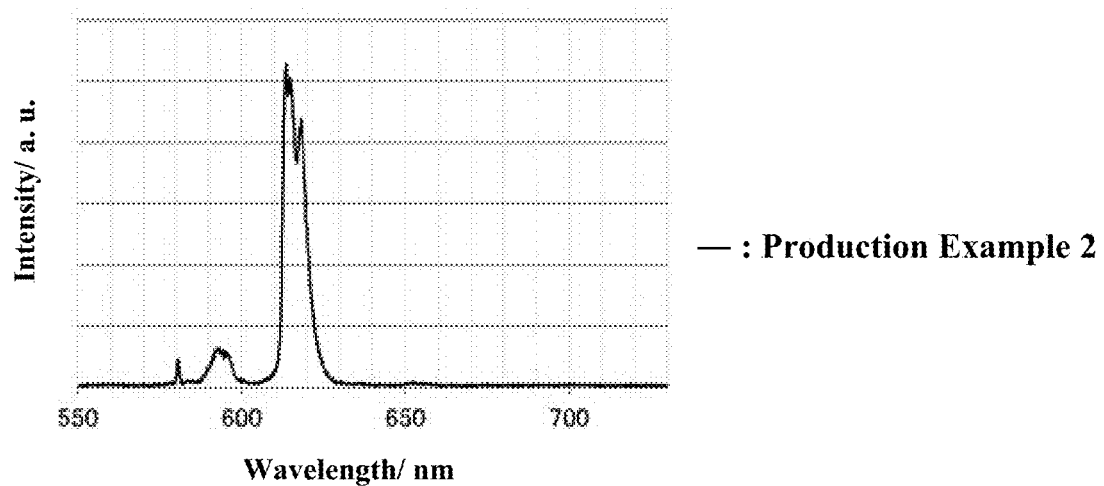
— : Production Example 2

[FIG. 17]
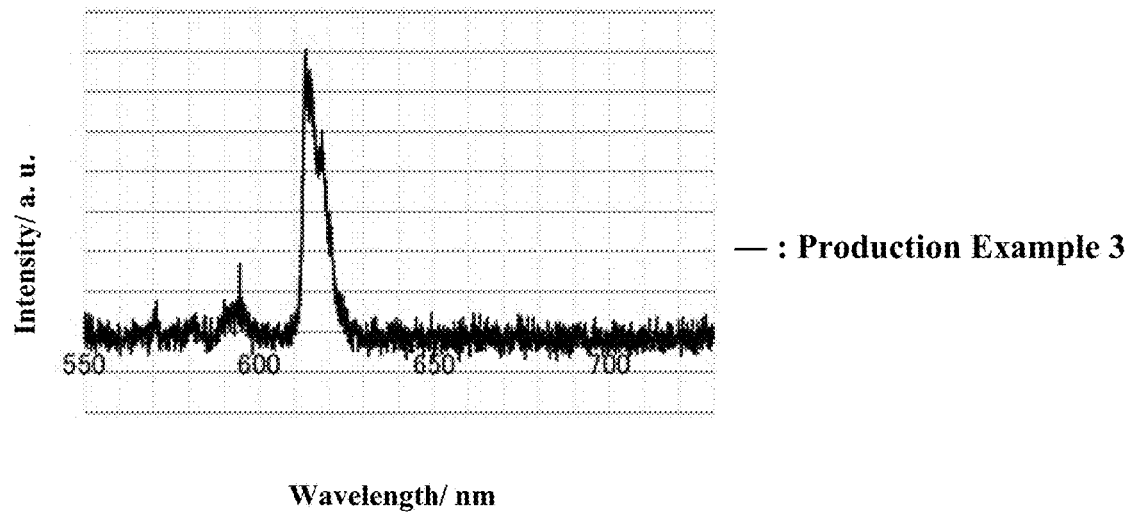
[FIG. 18]
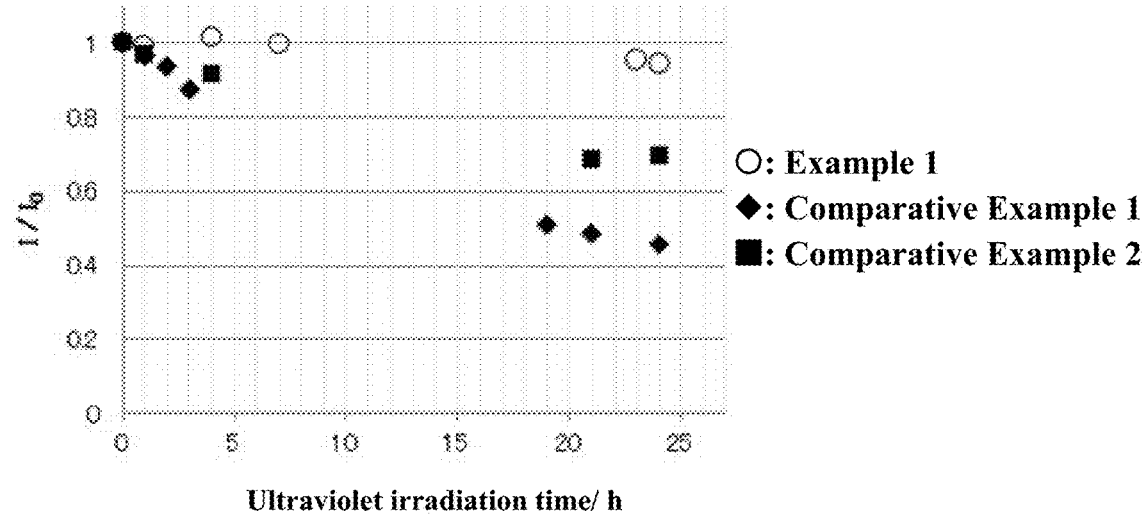

[FIG. 19]
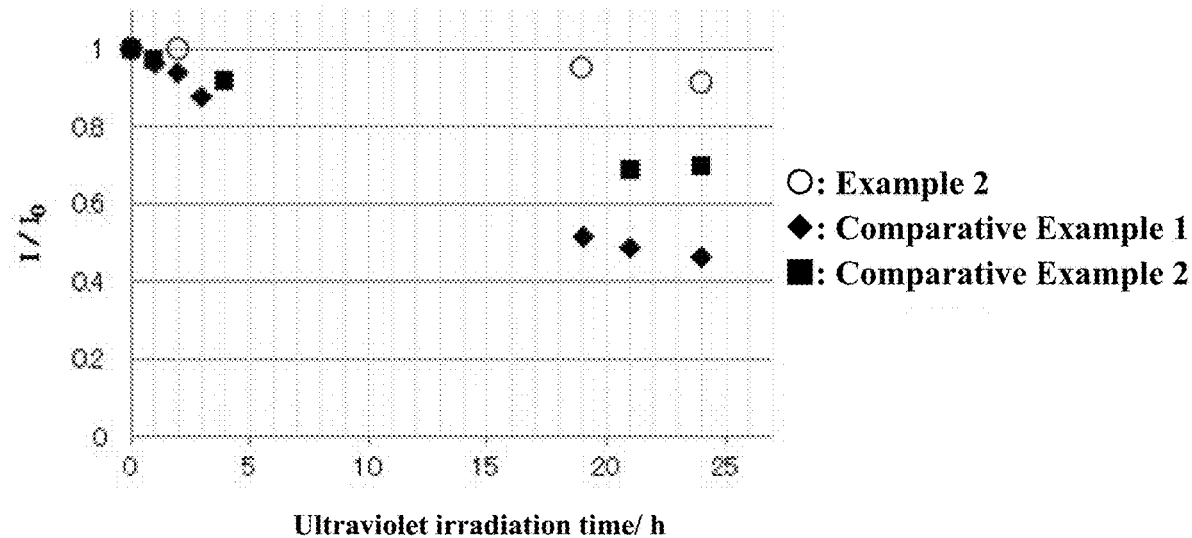
[FIG. 20]
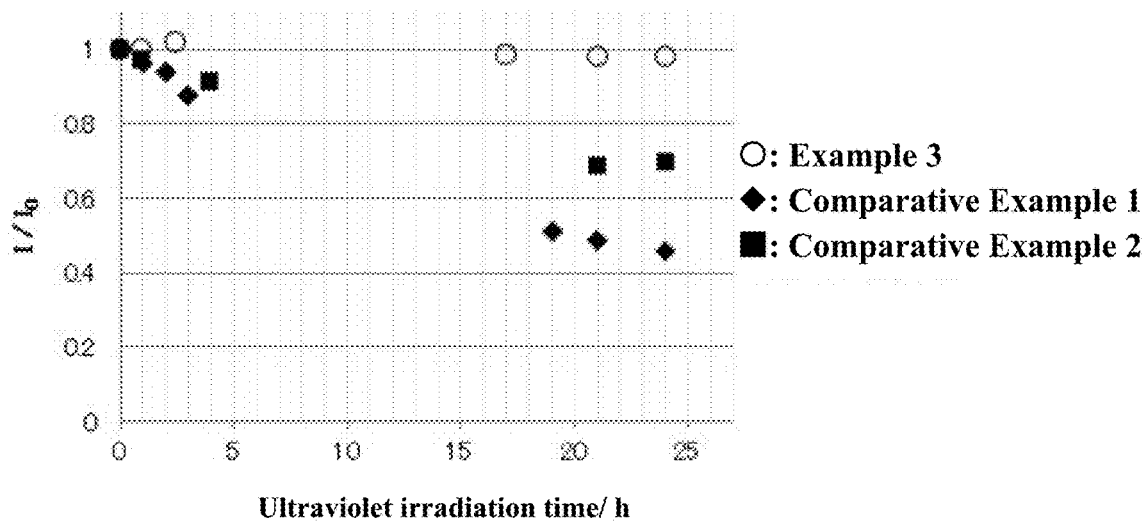

[FIG.21]
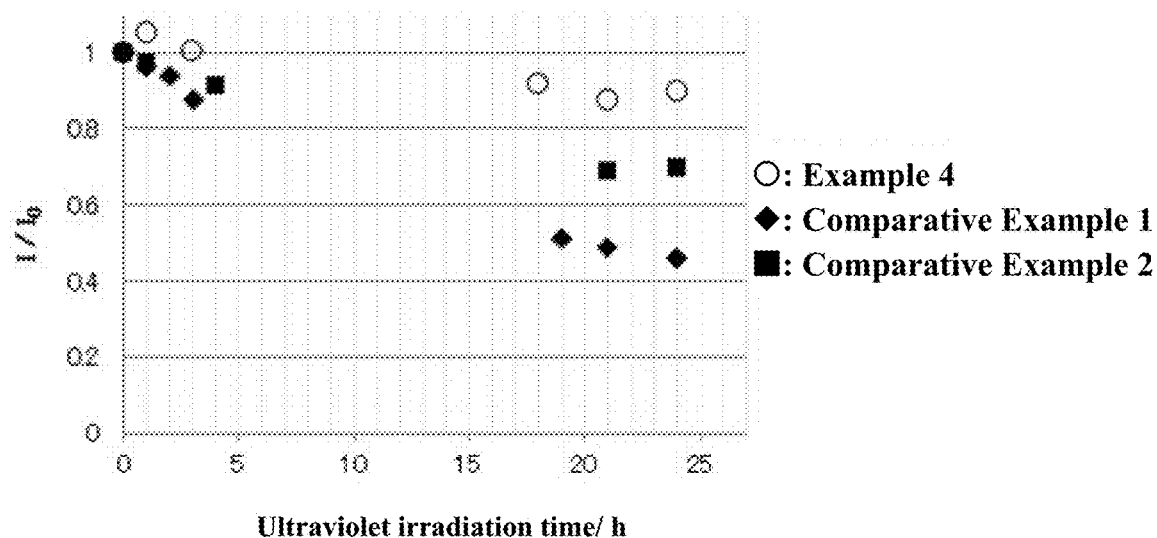
[FIG. 22]
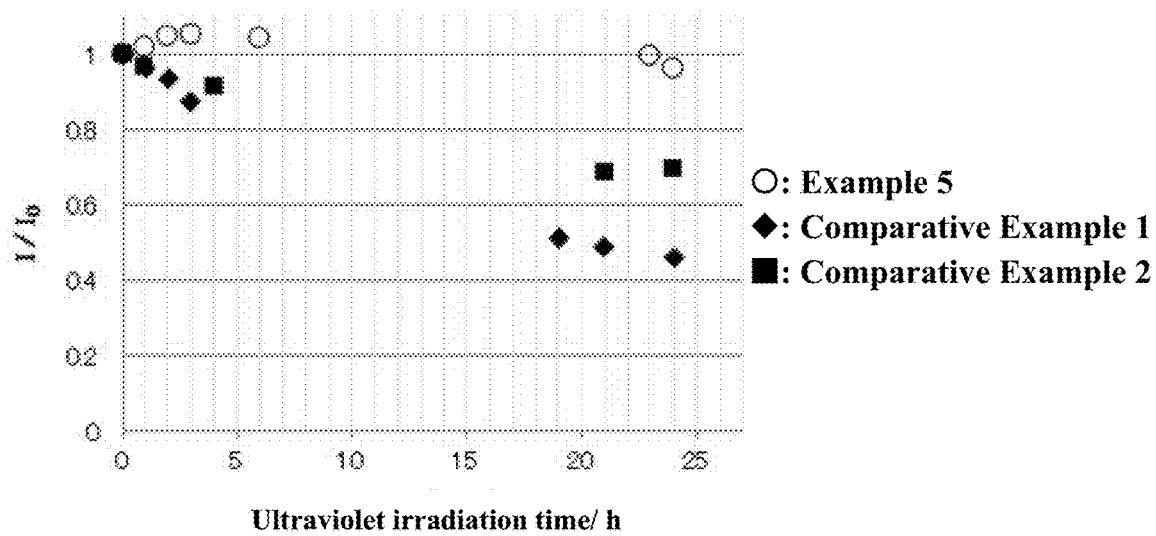

[FIG. 23]
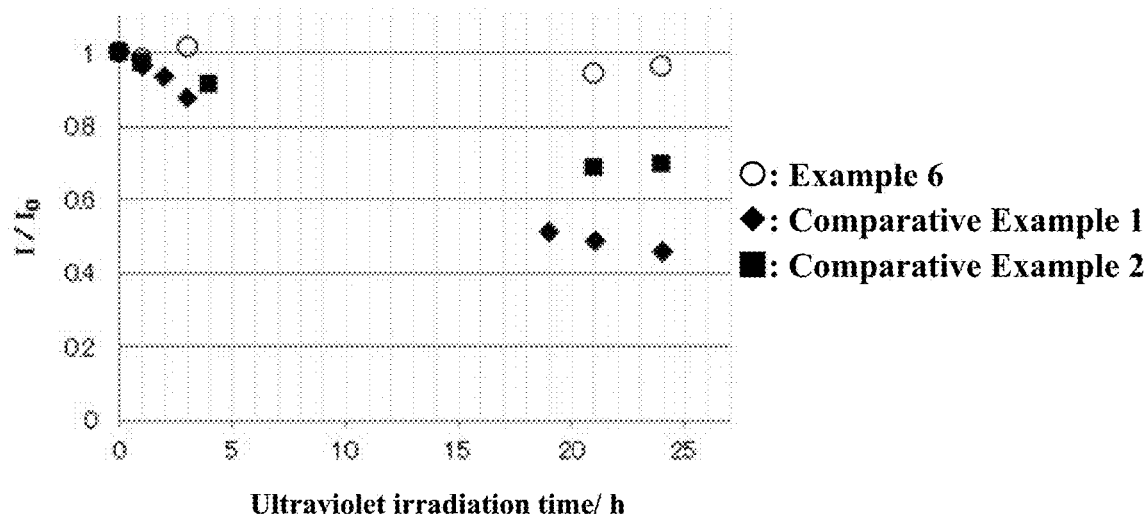
[FIG. 24]
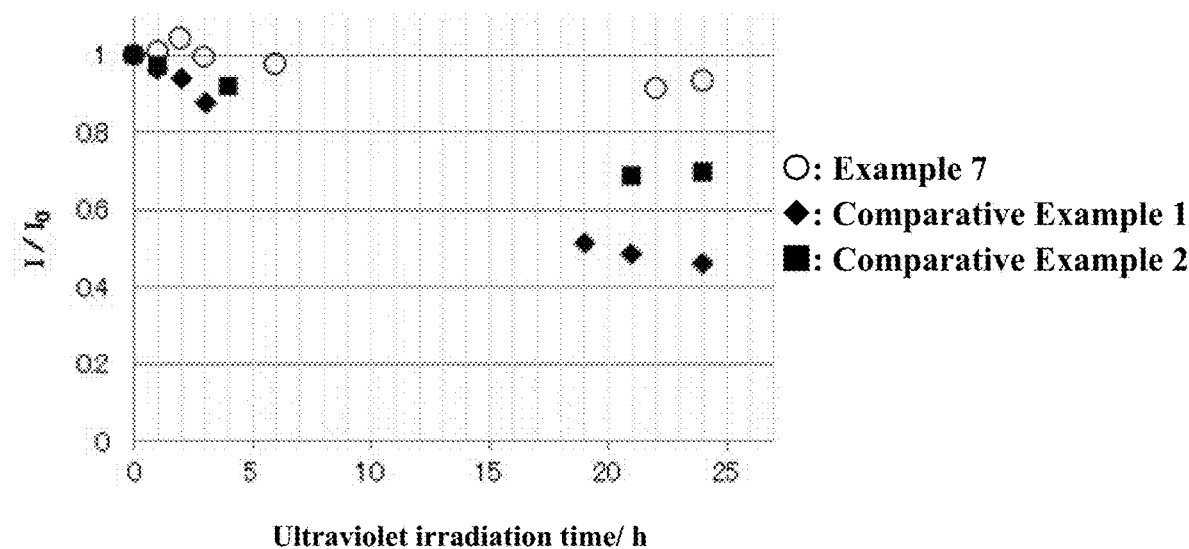

[FIG. 25]
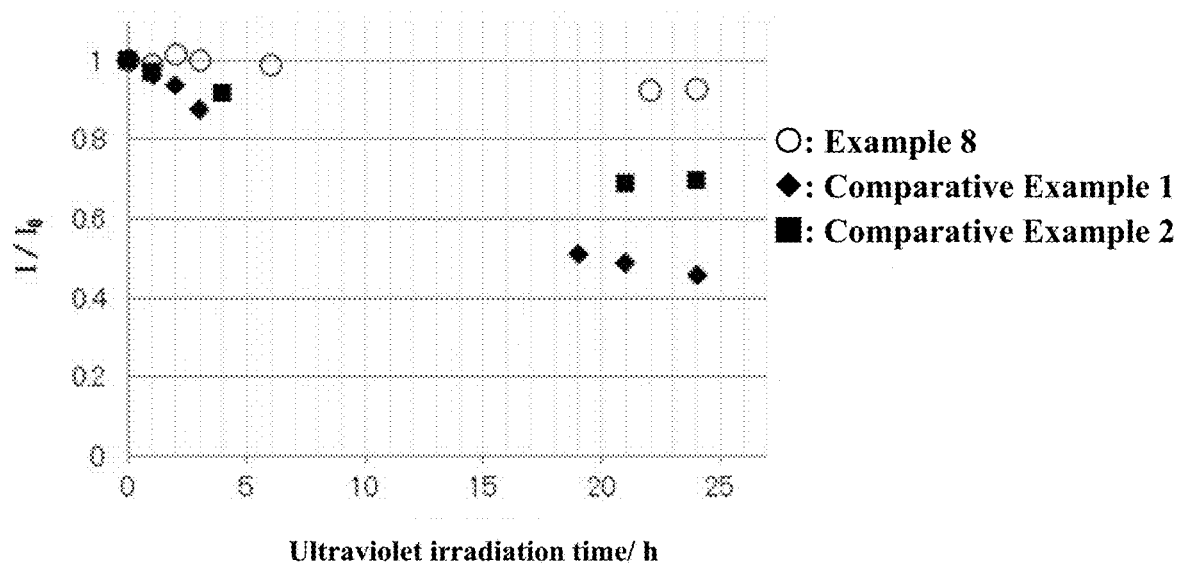
[FIG. 26]
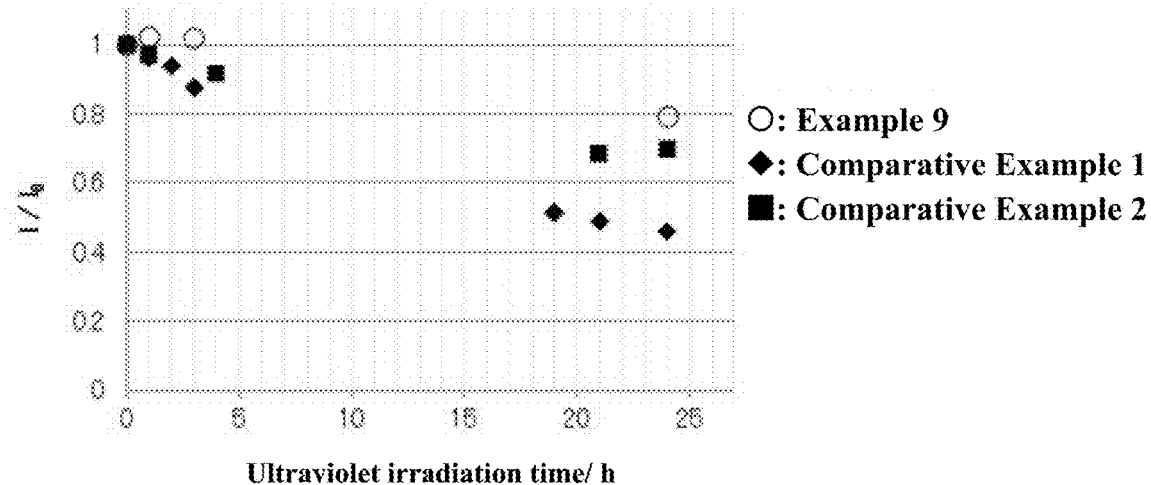

[FIG. 27]
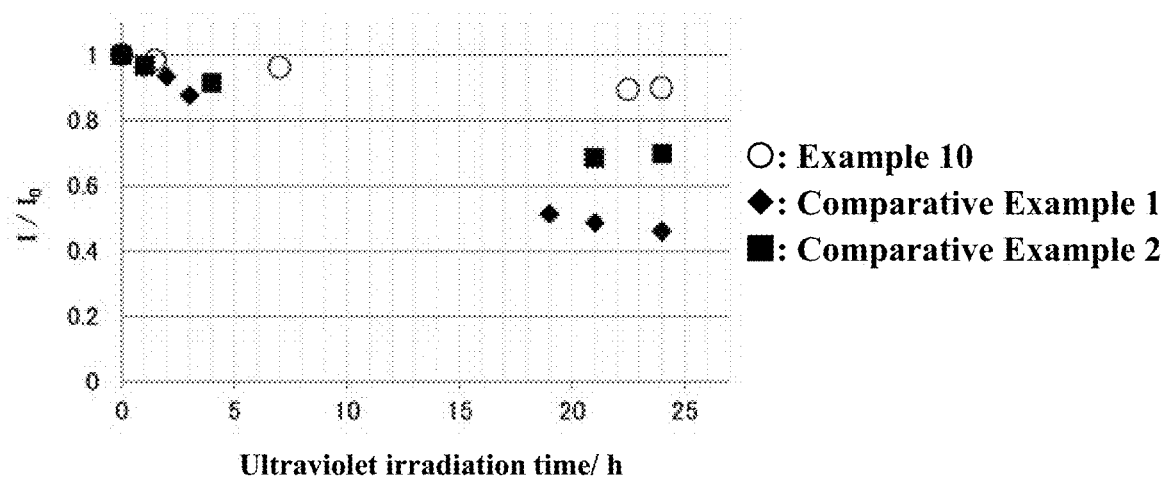
[FIG. 28]
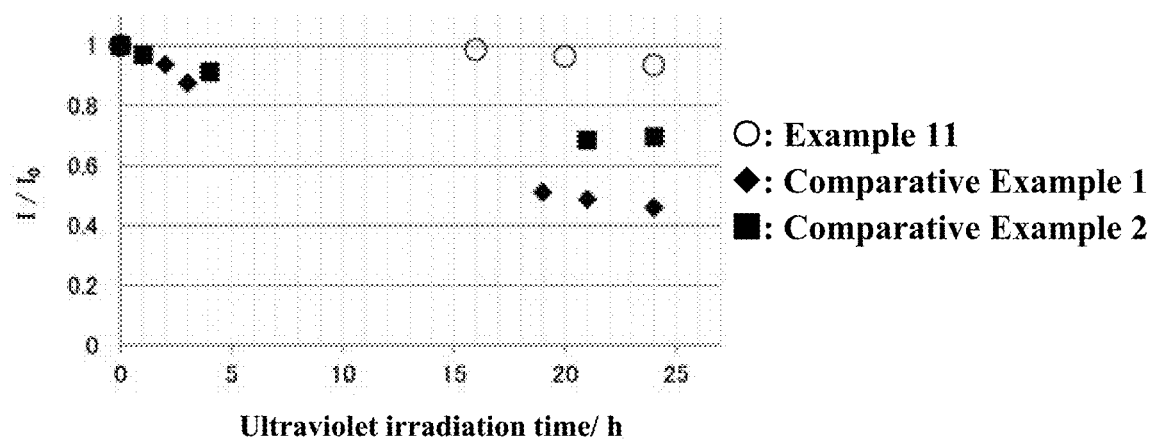

[FIG. 29]
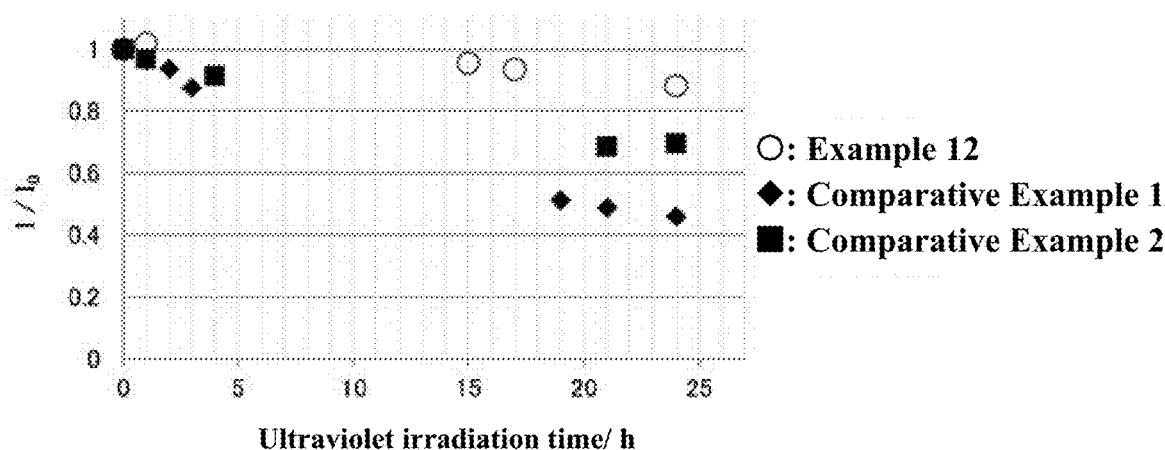
[FIG. 30]
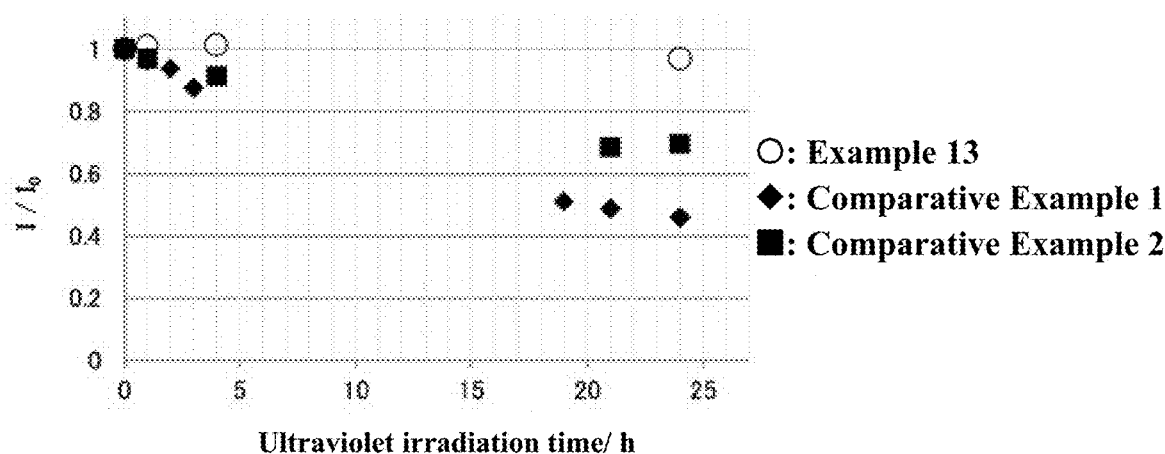

[FIG. 31]
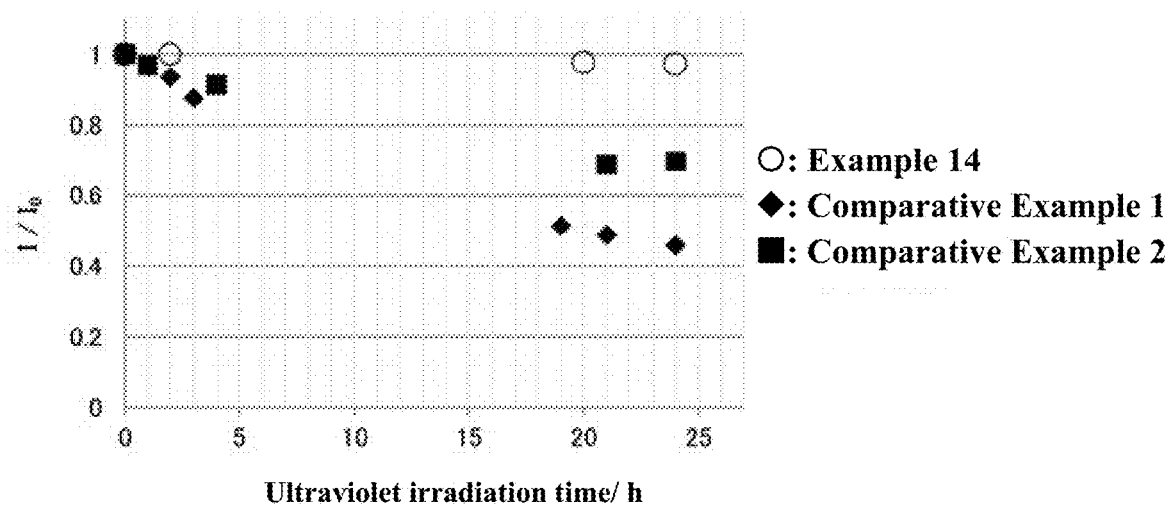
[FIG. 32]
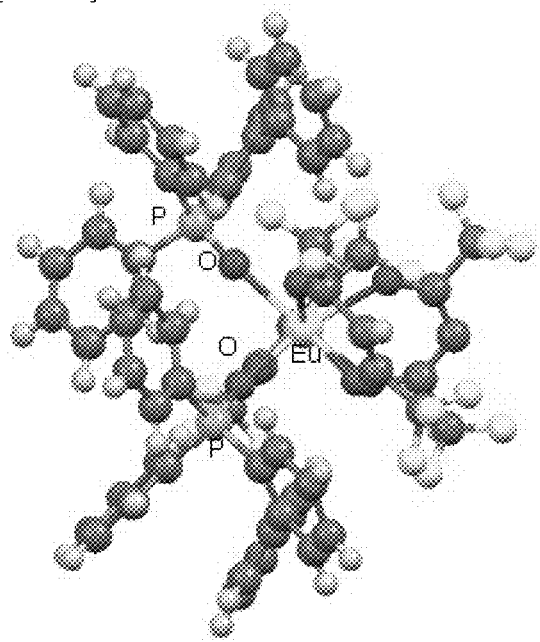

[FIG. 33]
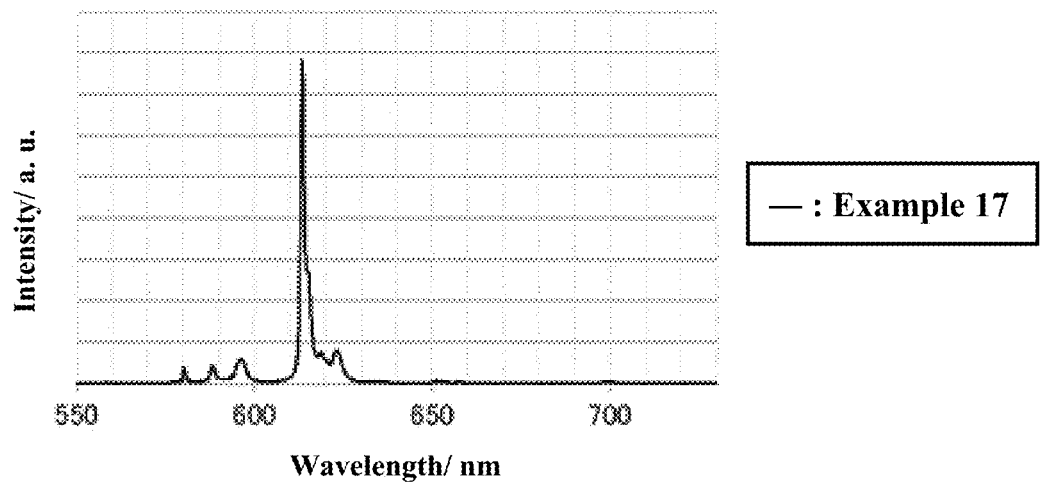
[FIG. 34]
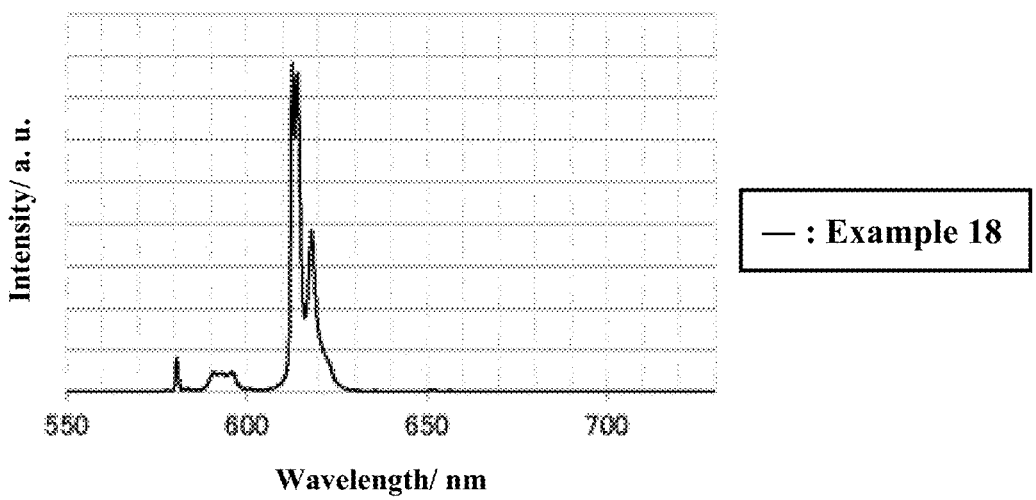
[FIG. 35]
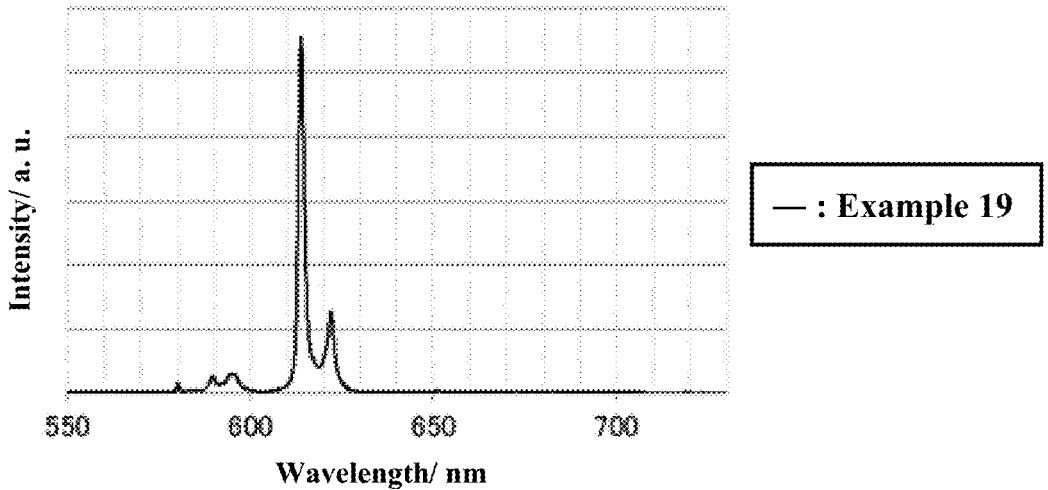

[FIG. 36]
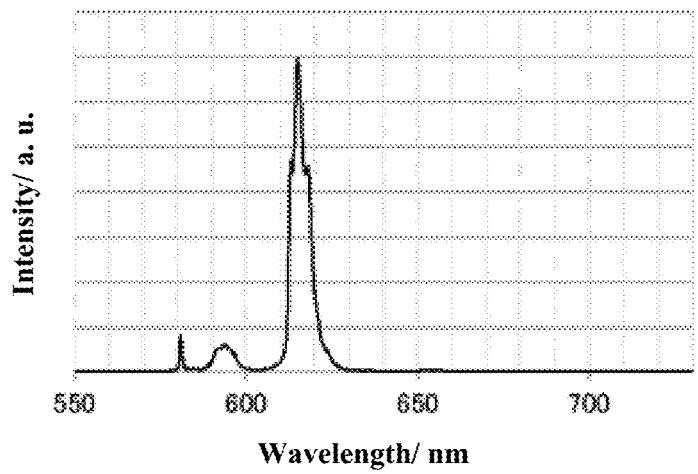
[FIG. 37]
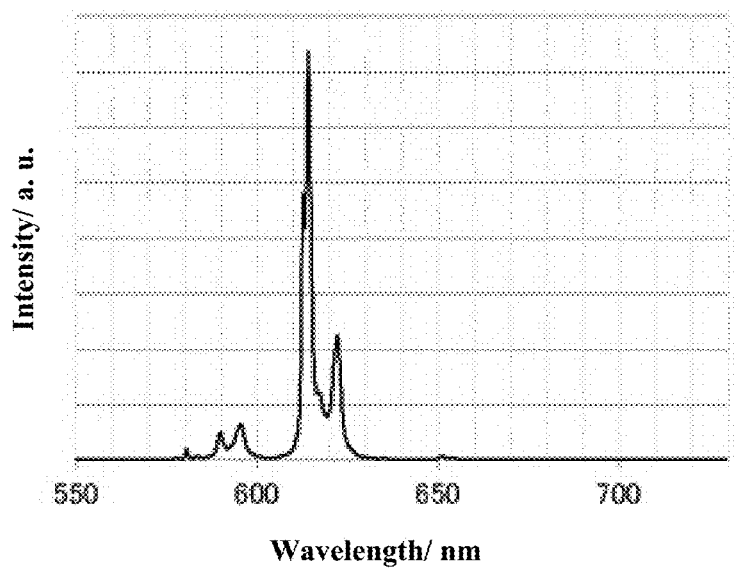

[FIG. 38]
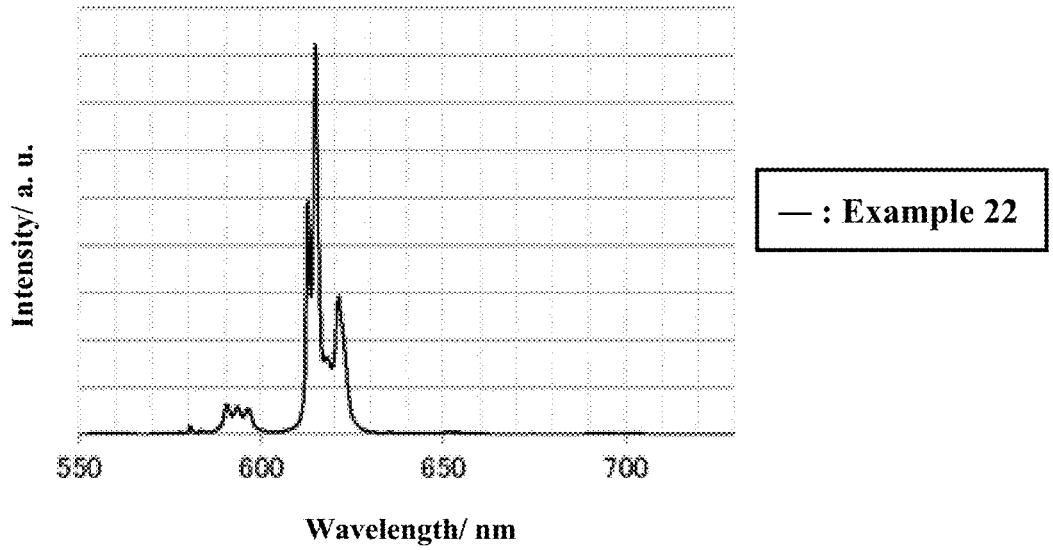
[FIG. 39]
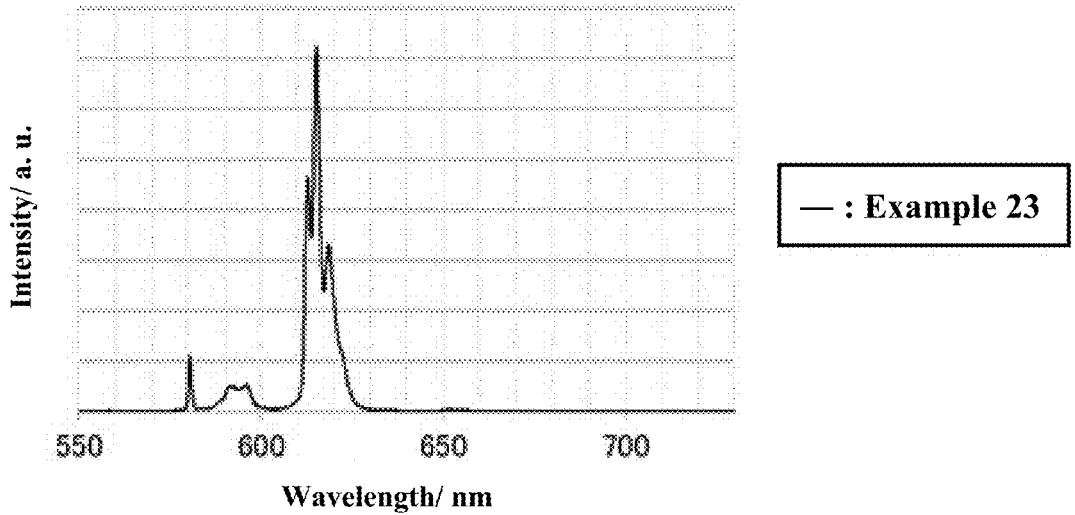

[FIG. 40]
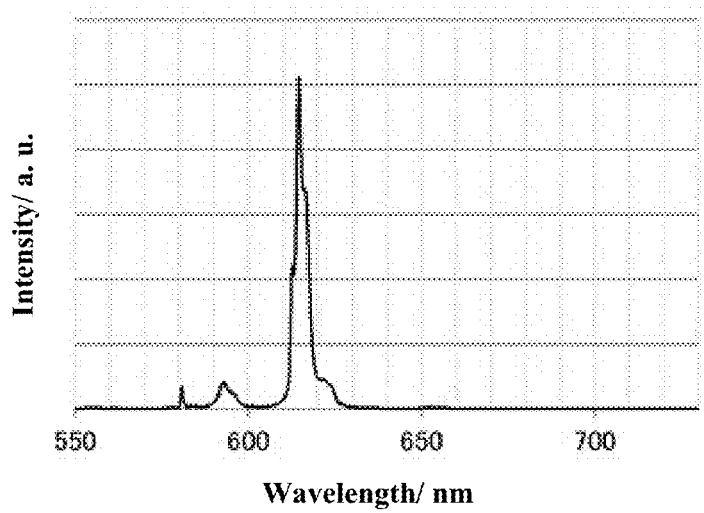
[FIG. 41]
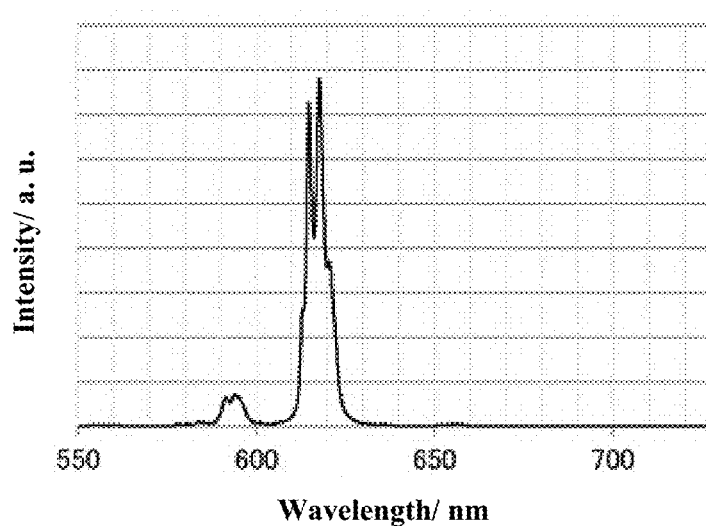

[FIG. 42]
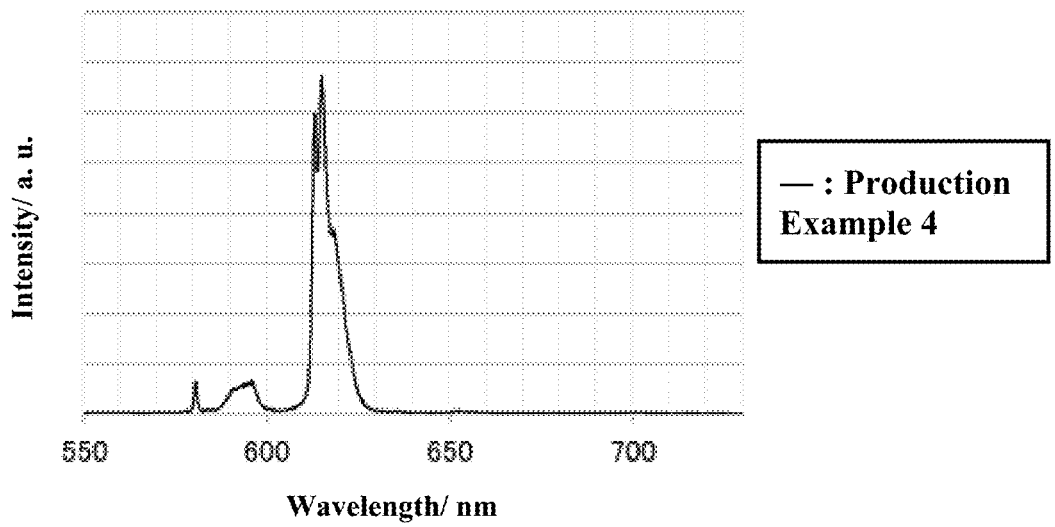
[FIG. 43]
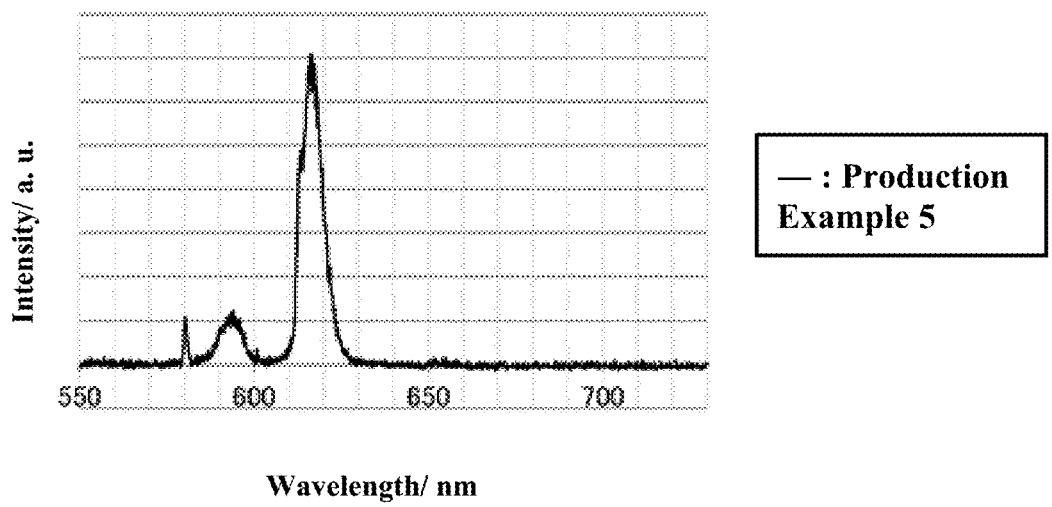

[FIG. 44]
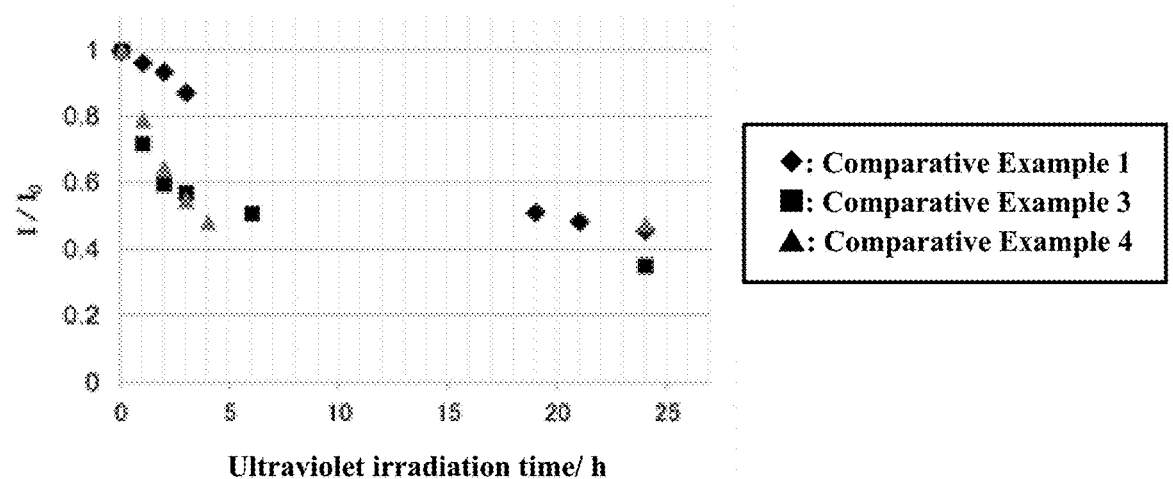
[FIG. 45]
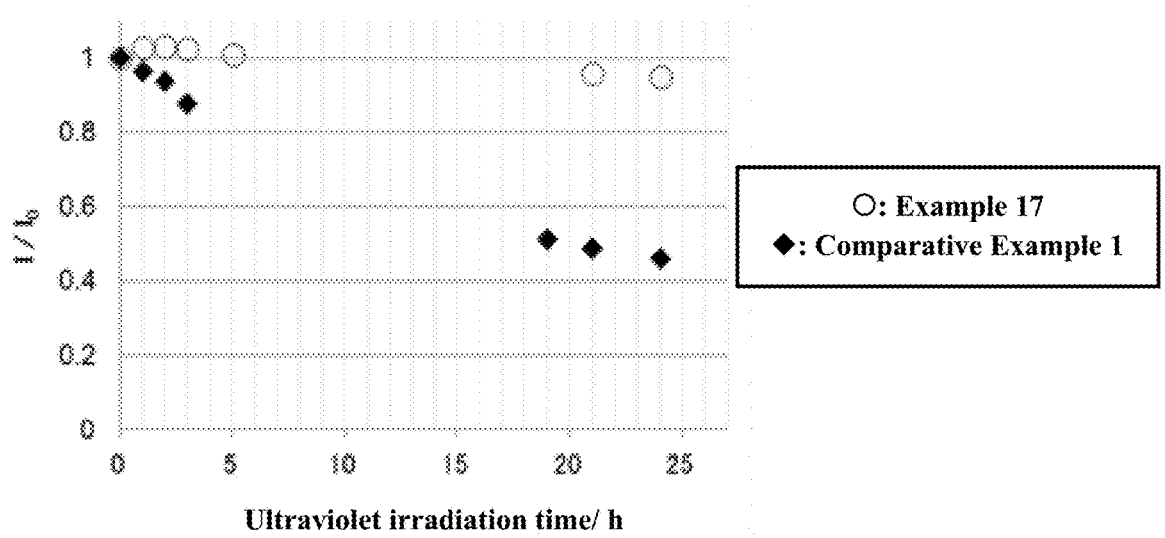

[FIG. 46]
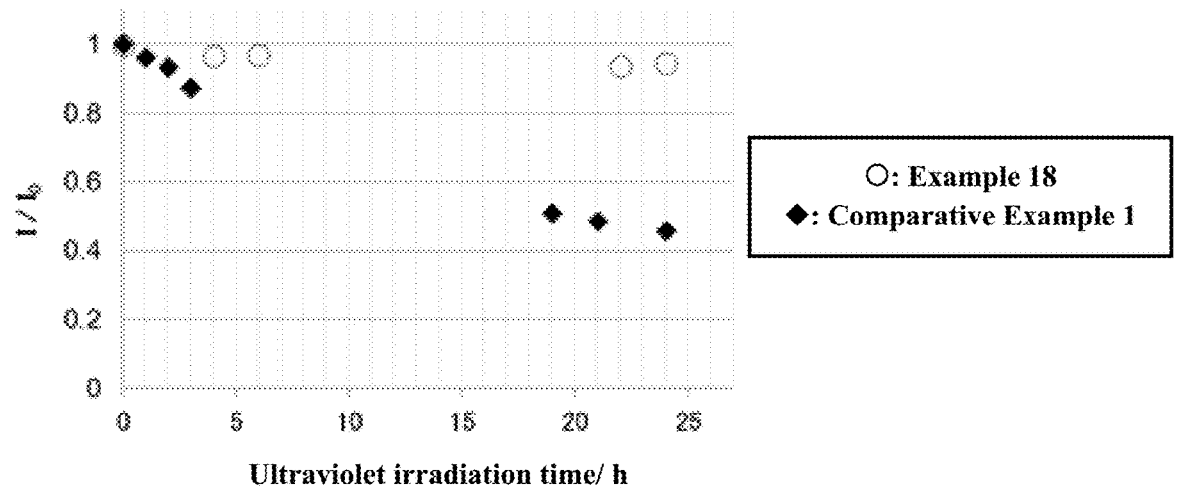
[FIG. 47]
[FIG. 48]
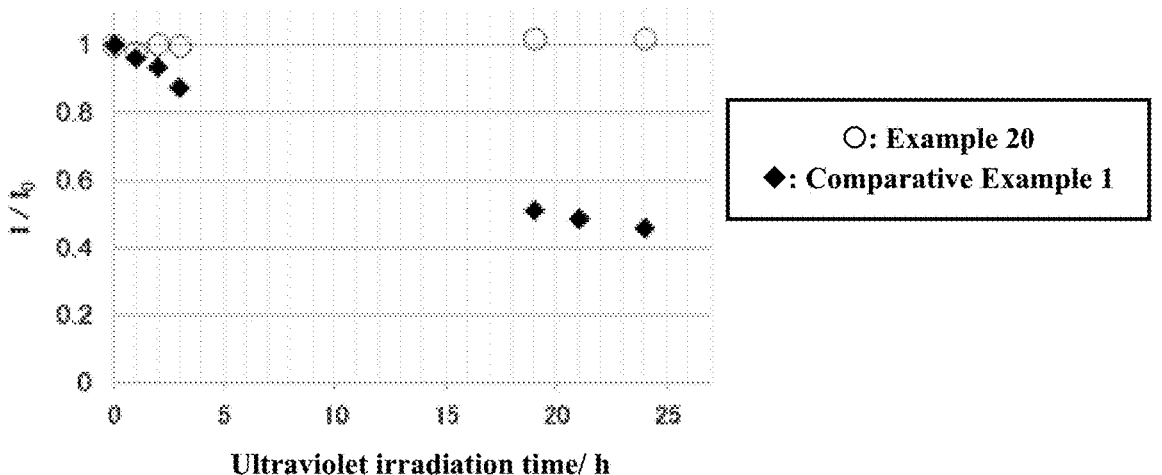

[FIG. 49]
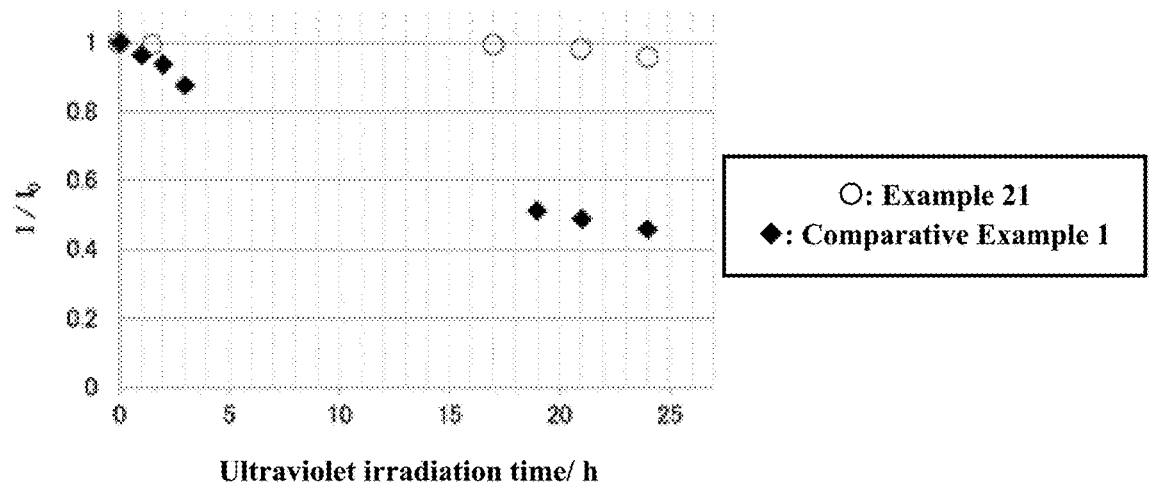
[FIG. 50]
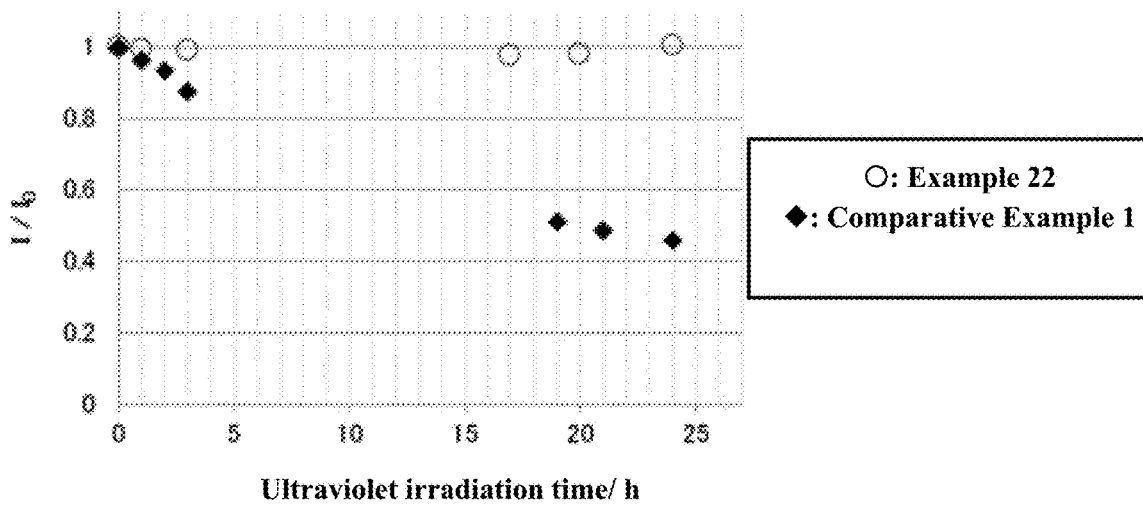
[FIG. 51]
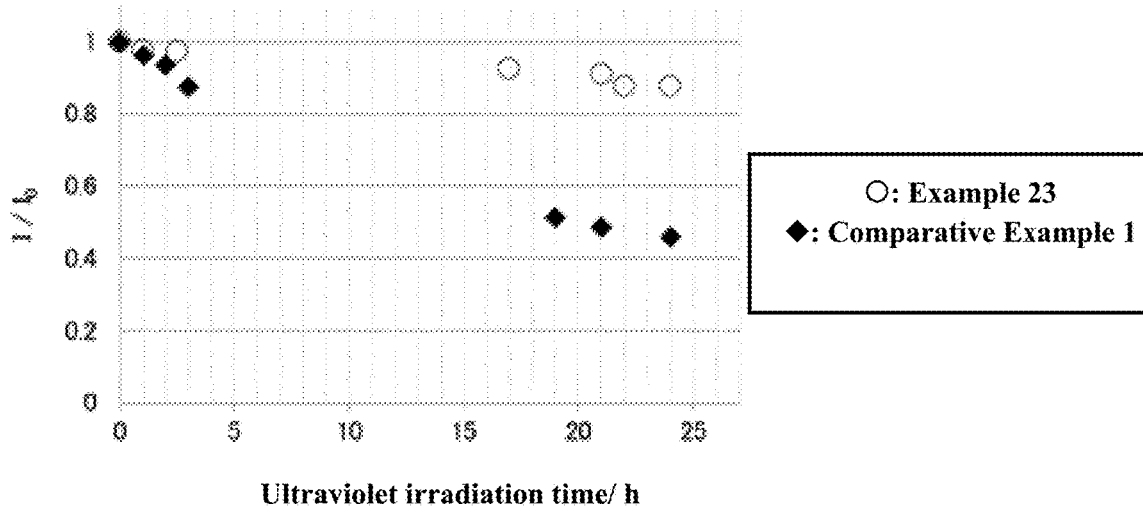

[FIG. 52]
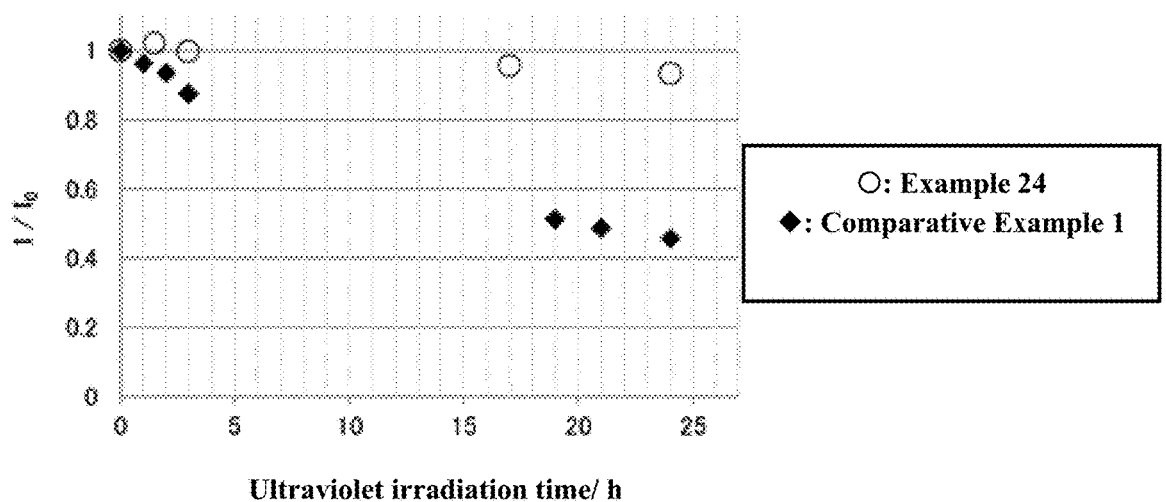
[FIG. 53]
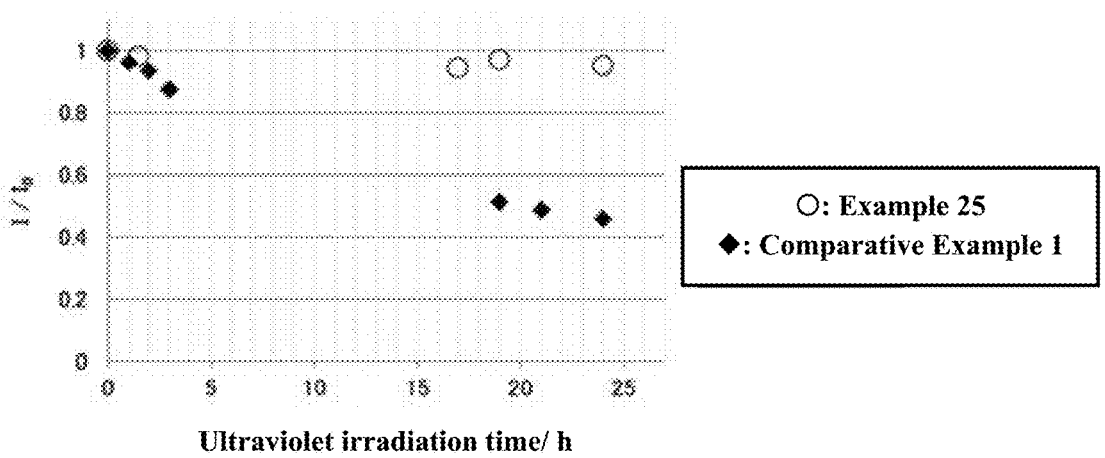

EUROPIUM COMPLEX

This application is the U.S. national phase of International Application No. PCT/JP2018/043579 filed Nov. 27, 2018 which designated the U.S. and claims priority to JP Patent Application No. 2017-227187 filed Nov. 27, 2017 and JP Patent Application No. 2018-052956 filed Mar. 20, 2018, the entire contents of each of which are hereby incorporated by reference.

TECHNICAL FIELD

The present invention relates to a europium complex having high light resistance.

BACKGROUND TECHNOLOGY

Technologies of optical materials have been actively developed as basic materials in the optoelectronics field, such as optical communications or displays, and in the energy field, such as photovoltaics, and various inorganic glass materials, ceramic materials, laser materials, organic low-molecular luminescence materials, rare-earth metal complexes and the like have been created.

The rare-earth metal complexes are characterized by absorbing a certain wavelength and becoming luminous in another wavelength, and are anticipated to be superior wavelength conversion materials. Further, the wavelength conversion materials require high light resistance in addition to having intense luminescence.

These days, europium complexes having a β-diketonato ligand and a phosphine oxide ligand (see Patent Literatures 1 and 2) have been reported as an intense light emitting rare-earth metal complex. Further, even though the europium complexes disclosed in Patent Literature 3, Patent Literature 4, Non-patent Literature 1, Non-patent Literature 2 and Non-patent Literature 3 are similar to the europium complexes mentioned in the present application, there are no descriptions about the light resistance of these complexes at all.

PRIOR ART DOCUMENTS

Patent Literature

[Patent Literature 1] RUB1453860
[Patent Literature 2] JP-A-2003-81986
[Patent Literature 3] JP-A-2005-223276
[Patent Literature 4] JP-A-2014-197144

Non-Patent Literature

[Non-patent Literature 1] Summary of Lectures at the 36th Inorganic Polymer Workshop, The Society of Polymer Science, Japan, 2017, P. 47
[Non-patent Literature 2] Proceedings of the 98th CSJ Annual Meeting (2018), The Chemical Society of Japan, 2PA-194
[Non-patent Literature 3] European Journal of Inorganic Chemistry, No. 3, P. 639 (2017)

SUMMARY OF THE INVENTION

Problem to be Solved by the Invention

The subject of the present invention is to provide europium complexes having high light resistance.

Means for Solving the Problem

The present inventors, as a result of keen examination in order to accomplish the subject above, discovered that a europium complex expressed with the formula (A), particularly a europium complex having a certain substituent at an ortho position of a phenyl group in a triphenylphosphine oxide derivative, in a europium complex having β-diketonato and phosphine oxide where a certain substituent has been introduced on a phosphorus atom as ligands or in another europium complex having β-diketonato and a triphenylphosphine oxide derivative as ligands, and completed the present invention.

The present invention has the following summary:

(1) A europium complex characterized by being expressed with the following formula (A):

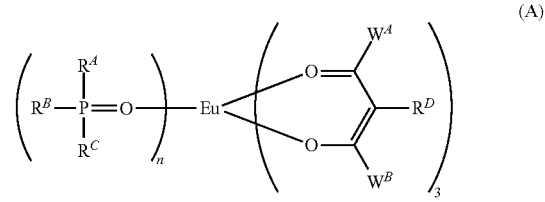

[wherein, $R^A$ and $R^B$ are independently a cyclic alkyl group with 3 to 10 carbons, respectively, and $R^C$ represents a cyclic alkyl group with 3 to 10 carbons or a phenyl group expressed with a formula (B)

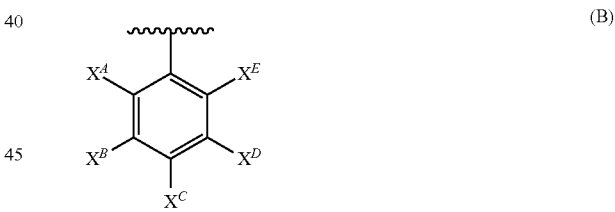

(wherein, $X^A$, $X^B$, $X^C$, $X^D$ and $X^E$ independently represent a hydrogen atom; a fluorine atom; an alkyl group with 1 to 3 carbon(s); an alkyloxy group with 1 to 3 carbon(s); an aryloxy group with 6 to 10 carbons; a fluoroalkyl group with 1 to 3 carbon(s); a fluoroalkyloxy group with 1 to 3 carbon(s); or a phenyl group that may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group or a cyano group, respectively), or $R^A$ is a cyclic alkyl group with 1 to 3 carbon(s), $R^B$ and $R^C$ are a phenyl group expressed with the formula (B), provided, however, that a case where $R^A$ is a cyclohexyl group, and, $R^B$ and $R^C$ are a phenyl group is excluded. Alternatively, $R^A$, $R^B$ and $R^C$ independently represent an ortho-substituted phenyl group expressed with a formula (Ba)

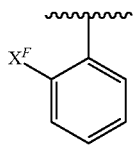

(Ba)

(wherein, $X^F$ is a hydrogen atom, an alkyl group with 1 to 3 carbon(s), alkyloxy group with 1 to 3 carbon(s), a fluoroalkyl group with 1 to 3 carbon(s), a fluoroalkyloxy group with 1 to 3 carbon(s), a naphthyl group that may be substituted with a fluorine atom or a pyridyl group that may be substituted with a fluorine atom, or a phenyl group expressed with the formula (C)

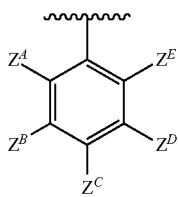

(C)

[wherein, $Z^A$, $Z^C$ and $Z^F$ independently represent a hydrogen atom, a fluorine atom, alkyl group with 1 to 3 carbon(s), a phenyl group that may be substituted with a fluorine atom, a hydroxyl group or a cyano group, respectively. $Z^B$ and $Z^D$ independently represent a hydrogen atom or a fluorine atom, respectively], provided, however, that a case where $R^A$, $R^B$ and $R^C$ are all a phenyl group is excluded).

$R^D$ represents a hydrogen atom, a deuterium atom or a fluorine atom. $W^A$ and $W^B$ independently represent an alkyl group with 1 to 6 carbon(s), a fluoroalkyl group with 1 to 6 carbon(s), a phenyl group, a 2-thienyl group or a 3-thienyl group, respectively. 'n' represents an integer of 1 to 3.]

(2) The europium complex according to (1) expressed with the following formula (1):

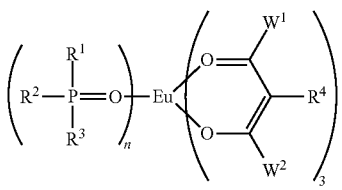

(1)

[wherein, $R^1$ and $R^2$ are independently a cyclic alkyl group with 3 to 10 carbons, respectively, and $R^3$ represents a cyclic alkyl group with 3 to 10 carbons or a phenyl group expressed with the formula (2a)

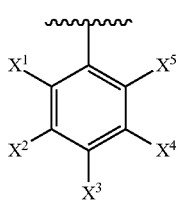

(2a)

(wherein, $X^1$, $X^2$, $X^3$, $X^4$ and $X^5$ independently represent a hydrogen atom; a fluorine atom; an alkyl group with 1 to 3 carbon(s); an alkyloxy group with 1 to 3 carbon(s); an aryloxy group with 6 to 10 carbons; a fluoroalkyl group with 1 to 3 carbon(s); a fluoroalkyloxy group with 1 to 3 carbon(s); or a phenyl group that may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group or a cyano group, respectively.) $R^4$ represents a hydrogen atom, a deuterium atom or a fluorine atom. $W^1$ and $W^2$ independently represent an alkyl group with 1 to 6 carbon(s), a fluoroalkyl group with 1 to 6 carbon(s), a phenyl group, a 2-thienyl group or a 3-thienyl group, respectively. 'n' represents an integer of 1 to 3.]

(3) The europium complex according to (1) or (2), wherein $R^3$ is a cyclic alkyl group with 3 to 10 carbons in the formula (1).

(4) The europium complex according to any of (1) to (3), wherein $R^1$, $R^2$ and $R^3$ are a cyclohexyl group in the formula (1).

(5) The europium complex according to any of (1) to (4) where 'n' is 2 in the formula (1).

(6) The europium complex according to any of (1) to (5) where $W^1$ and $W^2$ are independently a fluoroalkyl group with 1 to 6 carbon(s) in the formula (1), respectively.

(7) A europium complex according to (1) expressed with the following formula (1):

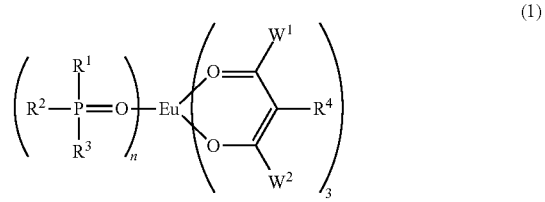

(1)

[wherein, $R^1$ is a cyclic alkyl group with 3 to 10 carbons, and $R^2$ and $R^3$ represent a phenyl group expressed with the formula (2a)

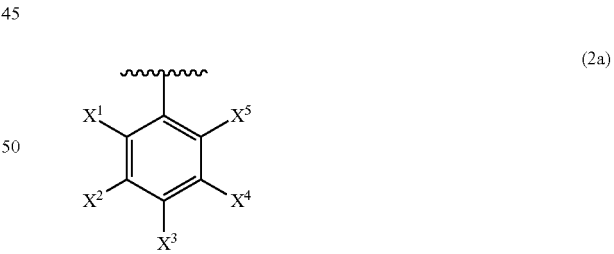

(2a)

(wherein, $X^1$, $X^2$, $X^3$, $X^4$ and $X^5$ independently represent a hydrogen atom; a fluorine atom; an alkyl group with 1 to 3 carbon(s); an alkyloxy group with 1 to 3 carbon(s); an aryloxy group with 6 to 10 carbons; a fluoroalkyl group with 1 to 3 carbon(s); a fluoroalkyloxy group with 1 to 3 carbon(s); or a phenyl group that may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group or a cyano group, respectively), provided, however, that a case where $R^1$ is a cyclohexyl group, and, $R^2$ and $R^3$ are a phenyl group is excluded. $R^4$ represents a hydrogen atom, a deuterium atom or a fluorine atom. $W^1$ and $W^2$ independently represent an alkyl group with 1 to 6 carbon(s), a fluoroalkyl group with 1 to 6 carbon(s), a phenyl group, a 2-thienyl group or a 3-thienyl group, respectively. 'n' represents an integer of 1 to 3.]

(8) The europium complex according to (1) or (7), wherein $R^1$ is a cyclohexyl group in the formula (1).
(9) The europium complex according to any of (1), (7) or (8), wherein 'n' is 2 in the formula (1).
(10) The europium complex according to any of (1), (7) to (9), wherein $W^1$ and $W^2$ are independently a fluoroalkyl group with 1 to 6 carbon(s) in the formula (1), respectively.
(11) The europium complex according to any of (1), (7) to (10), wherein $R^4$ is a hydrogen atom in the formula (1).
(12) The europium complex according to any of (1), (7) to (11), wherein $X^1$, $X^2$ and $X^3$ are independently a hydrogen atom, a methyl group or a phenyl group expressed with the following formula (2b), respectively, and $X^4$ and $X^5$ are independently a hydrogen atom or a methyl group, respectively, in the formula (2a):

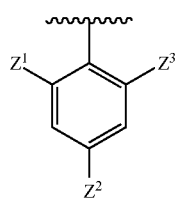

(2b)

[wherein, $Z^1$, $Z^3$ and $Z^3$ are independently a hydrogen atom, a fluorine atom, an alkyl group with 1 to 3 carbon(s), an alkyloxy group with 1 to 3 carbon(s), an aryloxy group with 6 to 10 carbons, a fluoroalkyl group with 1 to 3 carbon(s), a fluoroalkyloxy group with 1 to 3 carbon(s) or a phenyl group that may be substituted with a fluorine atom, respectively].

(13) The europium complex according to any of (1), (7) to (12), wherein $R^4$ is a hydrogen atom in the formula (1).
(14) The europium complex according to any of (1), (7) to (13), wherein $X^1$, $X^2$ and $X^3$ are independently a hydrogen atom, a methyl group or a phenyl group expressed with the following formula (2b), respectively, and $X^4$ and $X^5$ are independently a hydrogen atom or a methyl group, respectively, in the formula (2a):

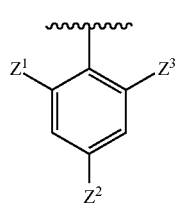

(2b)

[wherein, $Z^1$, $Z^2$ and $Z^3$ are independently a hydrogen atom, a fluorine atom, an alkyl group with 1 to 3 carbon(s), an alkyloxy group with 1 to 3 carbon(s), an aryloxy group with 6 to 10 carbons, a fluoroalkyl group with 1 to 3 carbon(s), a fluoroalkyloxy group with 1 to 3 carbon(s) or a phenyl group that may be substituted with a fluorine atom, respectively.]

(15) The europium complex according to any of (1), (7) to (14), wherein the europium complex is (1-1) to (1-11), (1-19) to (1-21).

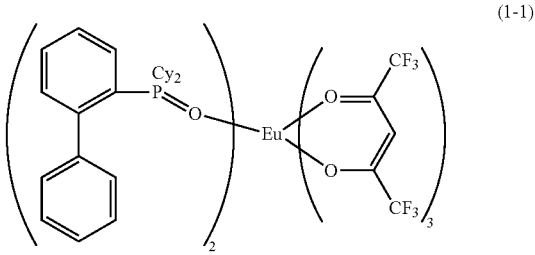

(1-1)

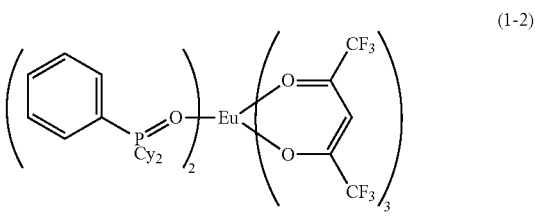

(1-2)

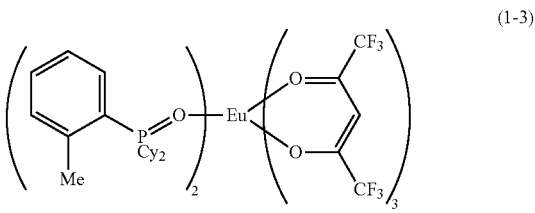

(1-3)

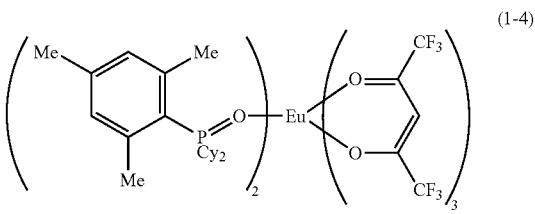

(1-4)

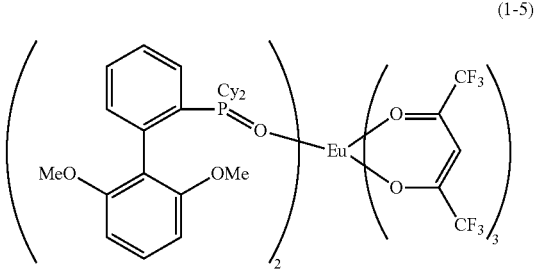

(1-5)

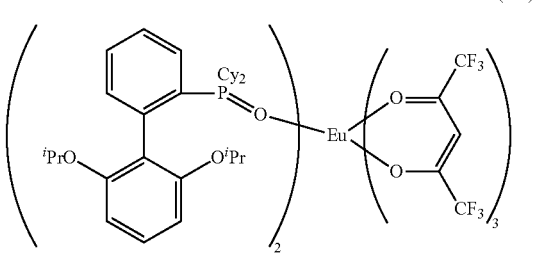

(1-6)

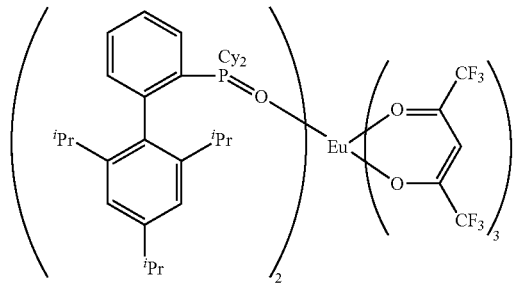
(1-7)

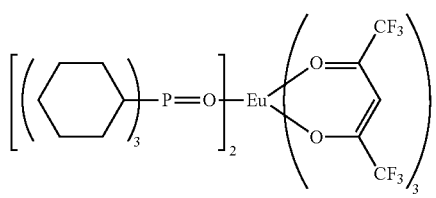
(1-8)

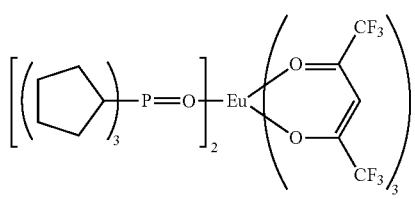
(1-9)

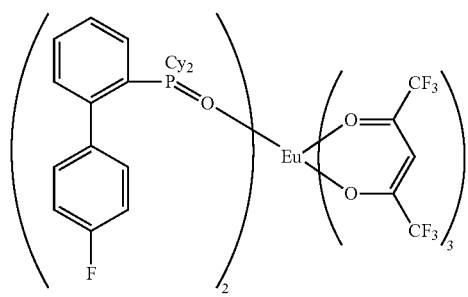
(1-10)

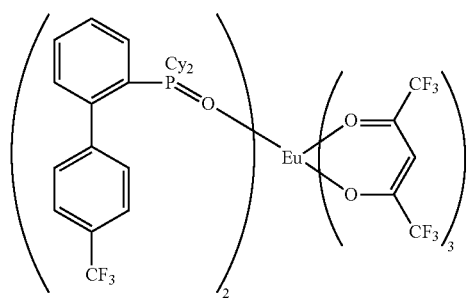
(1-11)

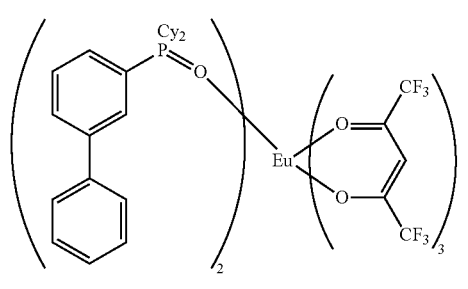
(1-19)

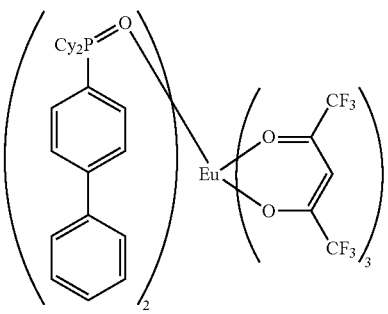
(1-20)

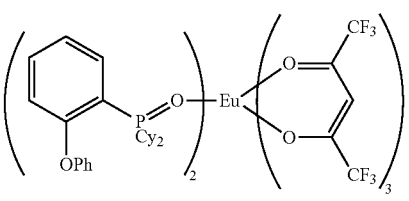
(1-21)

(16) The europium complex according to (1) expressed with the following formula (6):

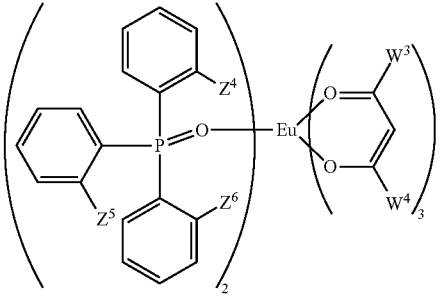
(6)

{wherein, $Z^4$, $Z^5$ and $Z^6$ independently represent a hydrogen atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a naphthyl group that may be substituted with a fluorine atom, a pyridyl group that may be substituted with a fluorine atom or a group expressed with the following formula (7), respectively,

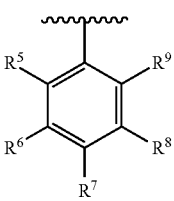
(7)

[wherein, $R^5$, $R^7$ and $R^9$ independently represent a hydrogen atom, a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a phenyl group that may be substituted with a fluorine atom, a hydroxyl group or a cyano group. $R^6$ and $R^8$ independently represent a hydrogen atom or a fluorine atom, respectively], provided, however, that $Z^4$, $Z^5$ and $Z^6$ cannot be a hydrogen atom at the same time. $W^3$ and $W^4$ independently represent an alkyl group with 1 to 6 carbon(s), a fluoroalkyl group with 1 to 6 carbon(s), a phenyl group, a 2-thienyl group or a 3-thienyl group, respectively.}

(17) The europium complex according to (1) or (16), wherein $W^3$ and $W^4$ are independently a fluoroalkyl group with 1 to 6 carbon(s), respectively.

(18) The europium complex according to (1), (16) or (17), wherein $Z^4$, $Z^5$ and $Z^6$ are independently a hydrogen atom, a methyl group, a methyloxy group or a group expressed with the formula (7) [wherein, $R^5$, $R^7$ and $R^9$ are independently a hydrogen atom, a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s) or a phenyl group, respectively, and $R^6$ and $R^8$ are a hydrogen atom], respectively.

(19) The europium complex according to any of (1), (16) to (18), wherein the formula (6) is a compound to be selected from a group consisting of (6-1) to (6-7), (6-22) and (6-23) below.

(6-1)

(6-2)

(6-3)

(6-4)

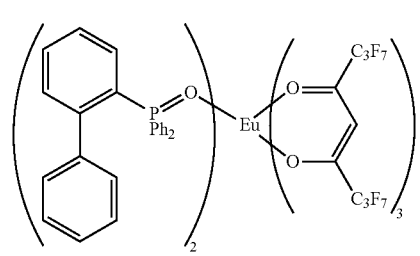

(6-5)

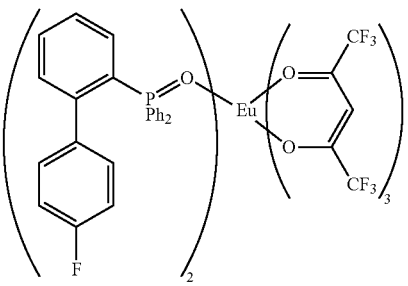

(6-6)

(6-7)

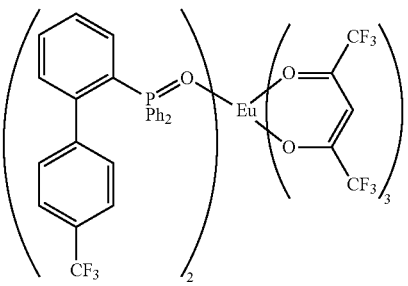

(6-22)

(6-23)

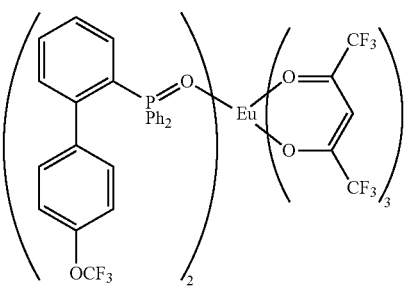

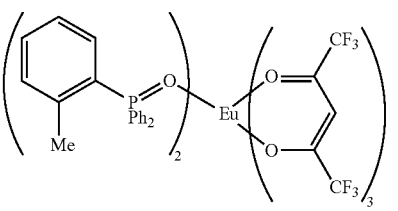

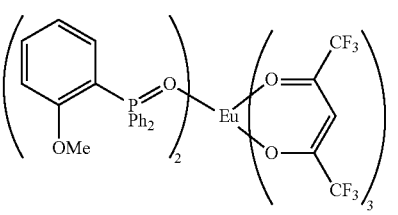

Effect of the Invention

The europium complexes of the present invention, for example, europium complexes A, B and C, are compounds having superior light resistance, and because these are less prone to degradation even if being irradiated with sunlight, an ultraviolet light or the like for a long time and these have high light resistance, they can be superior wavelength conversion materials that can be used for a long time.

BRIEF DESCRIPTION OF DRAWINGS

FIG. 1 is an emission spectrum of a europium complex obtained in Example 1.

FIG. 2 is an emission spectrum of a europium complex obtained in Example 2.

FIG. 3 is an emission spectrum of a europium complex obtained in Example 3.

FIG. 4 is an emission spectrum of a europium complex obtained in Example 4.

FIG. 5 is an emission spectrum of a europium complex obtained in Example 5.

FIG. 6 is an emission spectrum of a europium complex obtained in Example 6.

FIG. 7 is an emission spectrum of a europium complex obtained in Example 7.

FIG. 8 is an emission spectrum of a europium complex obtained in Example 8.

FIG. 9 is an emission spectrum of a europium complex obtained in Example 9.

FIG. 10 is an emission spectrum of a europium complex obtained in Example 10.

FIG. 11 is an emission spectrum of a europium complex obtained in Example 11.

FIG. 12 is an emission spectrum of a europium complex obtained in Example 12.

FIG. 13 is an emission spectrum of a europium complex obtained in Example 13.

FIG. 14 is an emission spectrum of a europium complex obtained in Example 14.

FIG. 15 is an emission spectrum of an optical material containing a europium complex obtained in Production Example 1.

FIG. 16 is an emission spectrum of an optical material containing a europium complex obtained in Production Example 2.

FIG. 17 is an emission spectrum of an optical material containing a europium complex obtained in Production Example 3.

FIG. 18 is an evaluation result of a light resistance test of the europium complex obtained in Example 1.

FIG. 19 is an evaluation result of a light resistance test of the europium complex obtained in Example 2.

FIG. 20 is an evaluation result of a light resistance test of the europium complex obtained in Example 3.

FIG. 21 is an evaluation result of a light resistance test of the europium complex obtained in Example 4.

FIG. 22 is an evaluation result of a light resistance test of the europium complex obtained in Example 5.

FIG. 23 is an evaluation result of a light resistance test of the europium complex obtained in Example 6.

FIG. 24 is an evaluation result of a light resistance test of the europium complex obtained in Example 7.

FIG. 25 is an evaluation result of a light resistance test of the europium complex obtained in Example 8.

FIG. 26 is an evaluation result of a light resistance test of the europium complex obtained in Example 9.

FIG. 27 is an evaluation result of a light resistance test of the europium complex obtained in Example 10.

FIG. 28 is an evaluation result of a light resistance test of the europium complex obtained in Example 11.

FIG. 29 is an evaluation result of a light resistance test of the europium complex obtained in Example 12.

FIG. 30 is an evaluation result of a light resistance test of the europium complex obtained in Example 13.

FIG. 31 is an evaluation result of a light resistance test of the europium complex obtained in Example 14.

FIG. 32 is a crystal structure of bis [(2-biphenylyl) diphenylphosphine oxide] tris (hexafluoroacetylacetonato) europium (III) obtained in Example 17.

FIG. 33 is an emission spectrum of the europium complex obtained in Example 17.

FIG. 34 is an emission spectrum of the europium complex obtained in Example 18.

FIG. 35 is an emission spectrum of the europium complex obtained in Example 19.

FIG. 36 is an emission spectrum of the europium complex obtained in Example 20.

FIG. 37 is an emission spectrum of the europium complex obtained in Example 21.

FIG. 38 is an emission spectrum of the europium complex obtained in Example 22.

FIG. 39 is an emission spectrum of the europium complex obtained in Example 23.

FIG. 40 is an emission spectrum of the europium complex obtained in Example 24.

FIG. 41 is an emission spectrum of the europium complex obtained in Example 25.

FIG. 42 is an emission spectrum of an optical material containing the europium complex obtained in Production Example 4.

FIG. 43 is an emission spectrum of an optical material containing the europium complex obtained in Production Example 5.

FIG. 44 is an evaluation result of a light resistance test of the europium complexes obtained in Comparative Examples 1, 3 and 4.

FIG. 45 is an evaluation result of a light resistance test of the europium complex obtained in Example 17.

FIG. 46 is an evaluation result of a light resistance test of the europium complex obtained in Example 18.

FIG. 47 is an evaluation result of a light resistance test of the europium complex obtained in Example 19.

FIG. 48 is an evaluation result of a light resistance test of the europium complex obtained in Example 20.

FIG. 49 is an evaluation result of a light resistance test of the europium complex obtained in Example 21.

FIG. 50 is an evaluation result of a light resistance test of the europium complex obtained in Example 22.

FIG. 51 is an evaluation result of a light resistance test of the europium complex obtained in Example 23.

FIG. 52 is an evaluation result of a light resistance test of the europium complex obtained in Example 24.

FIG. 53 is an evaluation result of a light resistance test of the europium complex obtained in Example 25.

MODE FOR CARRYING OUT THE INVENTION (Europium Complex)

Definitions of $R^A$, $R^B$, $R^C$, $R^D$, $X^A$, $X^B$, $X^C$, $X^D$, $X^E$, $X^F$, $Z^A$, $Z^B$, $Z^C$, $Z^D$, $Z^E$, n, $W^A$ and $W^B$ in the europium complex expressed with the formula (A) of the present invention are explained.

As the cyclic alkyl group with 3 to 10 carbons represented by $R^A$, $R^B$ and $R^C$, specifically, a cyclohexylmethyl group; a cyclopropyl group; a 2,3-dimethylcyclopropyl group; a cyclobutyl group; a cyclopentyl group; a 2,5-dimethylcyclopentyl group; a 3-ethylcyclopentyl group; a cyclohexyl group; a 4-ethylcyclohexyl group; a 4-propylcyclohexyl group; a 4,4-dimethylcyclohexyl group; a 2,6-dimethylcyclohexyl group; a 3,5-dimethylcyclohexyl group; a cycloheptyl group; a cyclooctyl group; a cyclononyl group; a cyclodecanyl group; a bicyclo [2,2,1] heptane-2-yl group; a bicyclo [2,2,2] octane-2-yl group; a cyclic secondary alkyl group; such as an adamantane-2-yl group; a bicyclo [2,2,1] heptane-2-yl group; an adamantane-1-yl group and the like can be exemplified.

As the alkyl group with 1 to 3 carbon(s) represented by $X^A$, $X^B$, $X^C$, $X^D$ and $X^E$ of the formula (B), either linear or branched ones are acceptable, and specifically, a methyl group, an ethyl group, a propyl group and an isopropyl group can be exemplified.

As the alkyloxy group with 1 to 3 carbon(s) represented by $X^A$, $X^B$, $X^C$, $X^D$ and $X^E$ of the formula (B), either linear or branched ones are acceptable, and specifically, a methoxy group, an ethoxy group, a propoxy group and a 1-methylethyloxy group can be exemplified.

As the aryloxy group with 6 to 10 carbons represented by $X^A$, $X^B$, $X^C$, $X^D$ and $X^E$ of the formula (B), specifically, a phenyloxy group, a 2-methylphenyloxy group, a 3-methylphenyloxy group, a 4-methylphenyloxy group, a 2,3-dimethylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group, a 2,3,4,5-tetramethylphenyloxy group, a 2,3,4,6-tetramethylphenyloxy group, a 2,3,5,6-tetramethylphenyloxy group, a 2-ethylphenyloxy group, a 3-ethylphenyloxy group, a 4-ethylphenyloxy group, a 2,3-diethylphenyloxy group, a 2,4-diethylphenyloxy group, a 2,5-diethylphenyloxy group, a 2,6-diethylphenyloxy group, a 3,4-diethylphenyloxy group, a 3,5-diethylphenyloxy group, a 2-propylphenyloxy group, a 3-propylphenyloxy group, a 4-propylphenyloxy group, a 2-isopropylphenyloxy group, a 3-isopropylphenyloxy group, a 4-isopropylphenyloxy group, a 2-cyclopropylphenyloxy group, a 3-cyclopropylphenyloxy group, a 4-cyclopropylphenyloxy group, a 2-butylphenyloxy group, a 3-butylphenyloxy group, a 4-butylphenyloxy group, a 2-(1-methylpropyl) phenyloxy group, a 3-(1-methylpropyl) phenyloxy group, a 4-(1-methylpropyl) phenyloxy group, a 2-(2-methylpropyl) phenyloxy group, a 3-(2-methylpropyl) phenyloxy group, a 4-(2-methylpropyl) phenyloxy group, a 2-cyclobutylphenyloxy group, a 3-cyclobutylphenyloxy group, a 4-cyclobutylphenyloxy group and the like can be exemplified.

As the fluoroalkyl group with 1 to 3 carbon(s) represented by $X^A$, $X^B$, $X^C$, $X^D$ and $X^E$ of the formula (B), either linear or branched ones are acceptable, and a trifluoromethyl group, a difluoromethyl group, a perfluoroethyl group, a 2,2,2-trifluoroethyl group, a 1,1-difluoroethyl group, a 2,2-difluoroethyl group, a perfluoropropyl group, a 2,2,3,3,3-pentafluoropropyl group, a 2,2,3,3-tetrafluoropropyl group, a 3,3,3-trifluoropropyl group, a 1,1-difluoropropyl group, a 1,1,1,2,3,3,3-hexafluoropropane-2-yl group, a 2,2,2-trifluoro-1-(trifluoromethyl) ethyl group and the like can be exemplified.

As the fluoroalkyloxy group with 1 to 3 carbon(s) represented by $X^A$, $X^B$, A $X^D$ and $X^E$ of the formula (B), either linear or branched ones are acceptable, and a trifluoromethyloxy group, a difluoromethyloxy group, a perfluoromethyloxy group, a 2,2,2-trifluoroethyloxy group, a 1,1-diifluoroethyloxy group, a 2,2-diifluoroethyloxy group, a perfluoropropyloxy group, a 2,2,3,3,3-pentafluoropropyloxy group, a 2,2,3,3-tetrafluoropropyloxy group, a 3,3,3-trifluoropropyloxy group, a 1,1-difluoropropyloxy group, a 1,1,1,2,3,3,3-hexafluoropropane-2-yloxy group, a 2,2,2-trifluoro-1-(trifluoromethyl) ethyl oxy group and the like can be exemplified.

If one or more of $X^A$, $X^B$, $X^C$, $X^D$ and $X^E$ in the formula (B) are a phenyl group, the phenyl group may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), an aryloxy group with 6 to 10 carbons, a fluorophenyl group, a hydroxyl group or a cyano group, and in the case of a phenyl group substituted with at least one or more in a group consisting of a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group and a cyano group (hereafter, referred to as "substituted phenyl group"), as the substituted phenyl group, a 2-fluorophenyl group, a 3-fluorophenyl group, a 4-fluorophenyl group, a 2-methylphenyl group, a 4-methylphenyl group, a 2,5-dimethylphenyl group, a 2,4,6-trimethylphenyl group, a 4-ethylphenyl group, 4-propylphenyl group, a 2,4,6-triisopropylphenyl, a 2-methoxyphenyl group, a 3-methoxyphenyl group, a 4-methoxyphenyl group, a 2,6-dimethoxyphenyl group, a 3,4-dimethoxyphenyl group, a 4-(isopropyloxy) phenyl group, a 2,6-di (isopropyloxy) phenyl group, a 2-phenoxyphenyl group, a 3-phenoxyphenyl group, a 4-phenoxyphenyl group, a 2-(trifluoromethyl) phenyl group, a 3-(trifluoromethyl) phenyl group, a 4-(trifluoromethyl) phenyl group, a 3,5-bis (trifluoromethyl) phenyl group, a 2-(trifluoromethyloxy) phenyl group, a 4-(trifluoromethyloxy) phenyl group, a 2'-fluorobiphenyl-2-yl group, a 4'-fluorobiphenyl-2-yl group, a 4'-fluorobiphenyl-4-yl group, a 3',5'-difluorobiphenyl-2-yl group, a 2-hydroxyphenyl group, a 3-hydroxyphenyl group and 4-hydroxyphenyl group, a 2-cyanophenyl group, a 3-cyanophenyl group, a 4-cyanophenyl group and the like can be exemplified.

$R^D$ represents a hydrogen atom, a deuterium atom or a fluorine atom.

'n' represents an integer of 1 to 3.

As the alkyl group with 1 to 6 carbon(s) represented by $W^A$ and $W^B$ in the formula (A), any of linear, branched and circular ones is acceptable, and specifically, a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-ethylpropyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, a 2-cyclobutylethyl group and the like can be exemplified.

As the fluoroalkyl group with 1 to 6 carbon(s) represented by $W^A$ and $W^B$ in the formula (A), any of linear, branched and circular ones is acceptable, and a trifluoromethyl group, a difluoromethyl group, a perfluoroethyl group, a 2,2,2-trifluoroethyl group, a 1,1-difluoroethyl group, a 2,2-difluoroethyl group, a perfluoropropyl group, a 2,2,3,3,3-pentafluoropropyl group, a 2,2,3,3-tetrafluoropropyl group, a 3,3,3-trifluoropropyl group, a 1,1-difluoropropyl group, a 1,1,1,2,3,3,3-hexafluoro-2-propyl group, a 2,2,2-trifluoro-1-(trifluoromethyl) ethyl group, a perfluorobutyl group, a 2,2,3,3,4,4,4-heptafluorobutyl group, a 3,3,4,4,4-pentafluorobutyl group, a 4,4,4-trifluorobutyl group, a 1,2,2,3,3,3-hexafluoro-1-(trifluoromethyl) propyl group, a 1-(trifluoromethyl) propyl group, a 1-methyl-3,3,3-trifluoropropyl group, a perfluoropentyl group, a 2,2,3,3,4,4,5,5,5-nonafluoropentyl group, a 3,3,4,4,5,5,5-heptafluoropentyl group, a 4,4,5,5,5-pentafluoropentyl group, a 5,5,5-trifluoropentyl group, a 1,2,2,3,3,3-hexafluoro-1-(1,1,2,2,2-pentafluoroethyl) propyl group, a 1,2,2,3,3,4,4,4-octafluoro-1-(trifluoromethyl) butyl group, a 1,1,2,3,3,4,4,4-octafluoro-2-(trifluoromethyl) butyl group, a 1,1,2,2,3,4,4,4-octafluoro-3-(trifluoromethyl) butyl group, a 1,1,3,3,3-pentafluoro-2,2-bis (trifluoromethyl) propyl group, a 2,2,3,3,3-pentafluoro-1,1-bis (trifluoromethyl) propyl group, a perfluorocyclopentyl group, a perfluorohexyl group, a 1,2,2,3,3,4.4.5.5.5-decafluoro-1-(trifluoromethyl) pentyl group, a 1,1,2,3,3,4.4.5.5.5-decafluoro-2-(trifluoromethyl) pentyl group, a 1,1,2,2,3,4,4,5,5,5-decafluoro-3-(trifluoromethyl) pentyl group, a 1,1,2,2,3,3,4,5,5,5-decafluoro-4-(trifluoromethyl) pentyl group, a 2,2,3,3,4,4,4-heptafluoro-1,1-bis (trifluoromethyl) butyl group, a 1,2,3,3,4,4,4-heptafluoro-1,2-bis (trifluoromethyl) butyl group, a 1,2,2,3,4,4,4-heptafluoro-1,3-bis (trifluoromethyl) butyl group, a 1,1,3,3,4,4,4-heptafluoro-2,2-bis (trifluoromethyl) butyl group, a 1,2,2,3,4,4,4-heptafluoro-2,3-bis (trifluoromethyl) butyl group, a 1,1,2,2.4,4,4-heptafluoro-3,3-bis (trifluoromethyl) butyl group, a perfluorocyclohexyl group, perfluorocyclopentylmethyl group and the like can be exemplified.

As the alkyl group with 1 to 3 carbon(s) represented by $X^F$ in the formula (B), either linear or branched ones are acceptable, and a methyl group, an ethyl group, a propyl group and an isopropyl group can be exemplified.

As the alkyloxy group with 1 to 3 carbon(s) represented by $X^F$, either linear or branched ones are acceptable, and a methyloxy group, an ethyloxy group, a propyloxy group and a 1-methylethyloxy group can be exemplified.

As the fluoroalkyl group with 1 to 3 carbon(s) represented by $X^F$, either linear or branched ones are acceptable, a trifluoromethyl group, a difluoromethyl group, a perfluoroethyl group, a 2,2,2-trifluoroethyl group, a 1,1-difluoroethyl group, a 2,2-difluoroethyl group, a perfluoropropyl group, a 2,2,3,3,3-pentafluoropropyl group, a 2,2,3,3-tetrafluoropropyl group, a 3,3,3-trifluoropropyl group, a 1,1-difluoropropyl group, a 1,1,1,2,3,3,3-hexafluoro-2-propyl group, a 2,2,2-trifluoro-1-(trifluoromethyl) ethyl group and the like can be exemplified.

As the fluoroalkyloxy group with 1 to 3 carbon(s) represented by $X^F$, either linear or branched ones are acceptable, and a trifluoromethyloxy group, a difluoromethyloxy group, a perfluoroethyloxy group, a 2,2,2-trifluoroethyloxy group, a 1,1-difluoroethyloxy group, a 2,2-difluoroethyloxy group, a perfluoropropyloxy group, a 2,2,3,3,3-pentafluoropropyloxy group, a 2,2,3,3-tetrafluoropropyloxy group, a 3,3,3-trifluoropropyloxy group, a 1,1-difluoropropyloxy group, a 1,1,1,2,3,3,3-hexafluoro-2-propyloxy group, a 2,2,2-trifluoro-1-(trifluoromethyl) ethyloxy group and the like can be exemplified.

As the naphthyl group that may be substituted with a fluorine atom represented by $X^F$, a 1-naphthyl group, a 2-naphthyl group, a 2-fluoronaphthalene-1-yl group, a 4-fluoronaphthalene-1-yl group, a 5-fluoronaphthalene-1-yl group, a 1-fluoronaphthalene-2-yl group, a 4-fluoronaphthalene-2-yl group, a 6-fluoronaphthalene-2-yl group, a 1,3,4,5,6,7,8-heptafluoronaphthalene-2-yl group and the like can be exemplified.

As the pyridyl group that may be substituted with a fluorine atom represented by $X^F$, a 2-pyridyl group, a 3-pyridyl group, a 4-pyridyl group, a 2-fluoropyridine-6-yl group, a 3,5-difluoropyridine-6-yl group, a 5-fluoropyridine-6-yl group, a 4-fluoropyridine-6-yl group, a 3-fluoropyridine-6-yl group, a 2-fluoropyridine-5-yl group, a 2,3-difluoropyridine-5-yl group, a 3-fluoropyridine-5-yl group, a 4-fluoropyridine-5-yl group, a 2-fluoropyridine-3-yl group, a 2-fluoropyridine-4-yl group, a 2,3,5,6-tetrafluoropyridine-4-yl group, a 3-fluoropyridine-4-yl group, a 3,5-difluoropyridine-4-yl group, a 2,6-difluoropyridine-3-yl group, a 2,5-difluoropyridine-3-yl group, a 2,5-difluoropyridine-4-yl group and the like can be exemplified.

As the alkyl group with 1 to 3 carbon(s) represented by $Z^A$, $Z^B$, $Z^C$, $Z^D$ and $Z^E$ in the formula (C), the similar ones to the alkyl group with 1 to 3 carbon(s) exemplified as $X^F$ can be exemplified.

As the alkyloxy group with 1 to 3 carbon(s) represented by $Z^A$, $Z^B$, $Z^C$, $Z^D$ and $Z^E$, the similar ones to the alkyloxy group with 1 to 3 carbon(s) exemplified as $X^F$ can be exemplified.

As the fluoroalkyl group with 1 to 3 carbon(s) represented by $Z^A$, $Z^B$, $Z^C$, $Z^D$ and $Z^E$, the similar ones to the fluoroalkyl group with 1 to 3 carbon(s) exemplified as $X^F$ can be exemplified.

As the fluoroalkyloxy group with 1 to 3 carbon(s) represented by $Z^A$, $Z^B$, $Z^C$, $Z^D$ and $Z^E$, the similar ones to the fluoroalkyloxy group with 1 to 3 carbon(s) exemplified as $X^F$ can be exemplified.

As the phenyl group that may be substituted with a fluorine atom represented by $Z^A$, $Z^B$, $Z^C$, $Z^D$ and $Z^E$, a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 2,4,6-trifluorophenyl group, a 3,4,5-trifluorophenyl group, a perorophenyl group and the like can be exemplified.

(Specific Examples of Europium Complexes)

Even among europium complexes expressed with the formula (A), a europium complex having β-diketonato and phosphine oxide where a specific substituent has been introduced onto a phosphorus atom as ligands or another europium complex (europium complex C) having β-diketonato and a triphenylphosphine oxide derivative as ligands is preferable.

Furthermore, the europium complex having β-diketonato and phosphine oxide where a specific substituent has been introduced onto a phosphorus atom as ligands is a europium complex where $R^1$ and $R^2$ have a cyclic alkyl group (europium complex A) and a europium complex where only R' has a cyclic alkyl group (europium complex B).

The europium complex A is a europium complex expressed with the following formula (1):

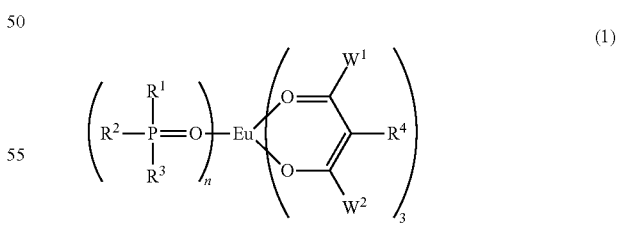

[wherein, $R^1$ and $R^2$ are independently a cyclic alkyl group with 3 to 10 carbons, respectively, and $R^3$ represents a cyclic alkyl group with 3 to 10 carbons or a phenyl group expressed with the formula (2a)

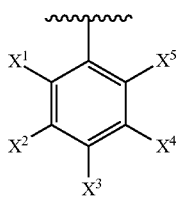

(2a)

(wherein, $X^1$, $X^2$, $X^3$, $X^4$ and $X^5$ independently represent a hydrogen atom; fluorine atom; an alkyl group with 1 to 3 carbon(s); an alkyloxy group with 1 to 3 carbon(s); an aryloxy group with 6 to 10 carbons; a fluoroalkyl group with 1 to 3 carbon(s); a fluoroalkyloxy group with 1 to 3 carbon(s); or a phenyl group that may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group or a cyano group, respectively). $R^4$ represents a hydrogen atom, a deuterium atom or a fluorine atom. $W^1$ and $W^2$ independently represent an alkyl group with 1 to 6 carbon(s), a fluoroalkyl group with 1 to 6 carbon(s), a phenyl group, a 2-thienyl group or a 3-thienyl group, respectively. 'n' represents an integer of 1 to 3.]

The europium complex B is a europium complex expressed with the following formula (1):

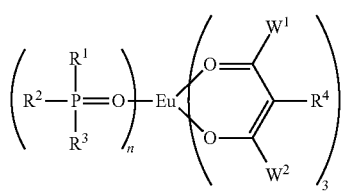

(1)

[wherein, $R^1$ is a cyclic alkyl group with 3 to 10 carbons, and $R^2$ and $R^3$ represent a phenyl group expressed with the formula (2a)

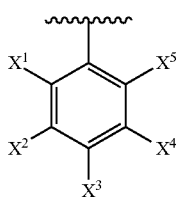

(2a)

(wherein, $X^1$, $X^2$, $X^3$, $X^4$ and $X^5$ independently represent a hydrogen atom; a fluorine atom; an alkyl group with 1 to 3 carbon(s); an alkyloxy group with 1 to 3 carbon(s); an aryloxy group with 6 to 10 carbons; a fluoroalkyl group with 1 to 3 carbon(s); a fluoroalkyloxy group with 1 to 3 carbon(s); or a phenyl group that may be substituted with a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a fluorophenyl group, a hydroxyl group or a cyano group), provided, however, that it excludes a case where R' is a cyclohexyl group, and, $R^2$ and $R^3$ are a phenyl group. $R^4$ represents a hydrogen atom, a deuterium atom or a fluorine atom. $W^1$ and $W^2$ independently an alkyl group with 1 to 6 carbon(s), a fluoroalkyl group with 1 to 6 carbon(s), a phenyl group, a 2-thienyl group or a 3-thienyl group, respectively. 'n' represents an integer of 1 to 3.]

The europium complex C is a europium complex expressed with the following formula (2):

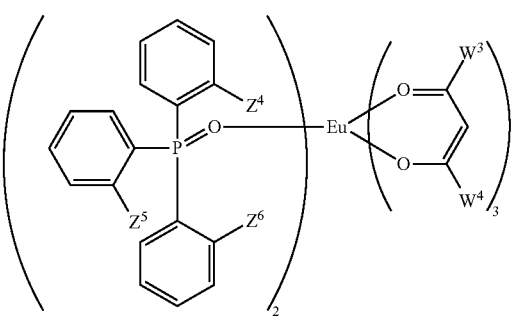

(6)

{wherein, $Z^4$, $Z^5$ and $Z^6$ independently represent a hydrogen atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a naphthyl group that may be substituted with a fluorine atom, a pyridyl group that may be substituted with a fluorine atom, or a group expressed with a formula (7)

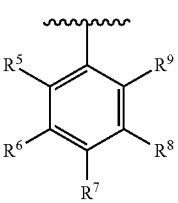

(7)

[wherein, $R^5$, $R^7$ and $R^9$ independently a hydrogen atom, a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s), a phenyl group that may be substituted with a fluorine atom, a hydroxyl group or a cyano group, respectively. $R^6$ and $R^8$ independently represent a hydrogen atom or a fluorine atom, respectively], respectively, provided, however, that $Z^4$, $Z^5$ and $Z^6$ cannot be a hydrogen atom at the same time. $W^3$ and $W^4$ independently represents an alkyl group with 1 to 6 carbon(s), a fluoroalkyl group with 1 to 6 carbon(s), a phenyl group, a 2-thienyl group or a 3-thienyl group, respectively.}

(Europium Complexes A and B)

The europium complexes A and B are explained.

Definitions of $R^1$, $R^2$, $R^3$, $R^4$, $X^1$, $X^2$, $X^3$, $X^4$, $X^5$, $Z^1$, $Z^2$, $Z^3$, n, $W^1$ and $W^2$ in the europium complexes A and B are as mentioned below.

As a cyclic alkyl group with 3 to 10 carbons represented by R' of the formula (1) in the europium complexes A and B and a cyclic alkyl group with 3 to 10 carbons represented by $R^2$ and $R^3$ of the formula (1) in the europium complex B, the cyclic alkyl group with 3 to 10 carbons that is similar to $R^A$, $R^B$ and $R^C$ of the formula (A) can be exemplified. A cyclopropyl group, a cyclobutyl group, a cyclopentyl group, a cyclohexyl group, a cycloheptyl group, a cyclooctyl group, a cyclononyl group, cyclodecanyl group and the like are preferable in terms of better light resistance in the europium complexes A and B, and a cyclopentyl group and a cyclohexyl group are preferable especially in terms of inexpensive cost.

As the alkyl group with 1 to 3 carbon(s) represented by $X^1$, $X^2$, $X^3$, $X^4$ and $X^5$ of the formula (2a) in the europium complexes A and B, the alkyl group with 1 to 3 carbon(s) that is similar to $X^A$, $X^B$, $X^C$, $X^D$ and $X^E$ of the formula (B) can be exemplified.

As the alkyloxy group with 1 to 3 carbon(s) represented by $X^1$, $X^2$, $X^3$, $X^4$ and $X^5$ of the formula (2a) in the europium complexes A and B, the alkyloxy group with 1 to 3 carbon(s) that is similar to $X^A$, $X^B$, $X^C$, $X^D$ and $X^E$ of the formula (B) can be exemplified.

As the aryloxy group with 6 to 10 carbons represented by $X^1$, $X^2$, $X^3$, $X^4$ and $X^5$ of the formula (2a) in the europium complexes A and B, the aryloxy group with 6 to 10 carbons that is similar to $X^A$, $X^B$, $X^C$, $X^D$ and $X^E$ of the formula (B) can be exemplified.

As the fluoroalkyl group with 1 to 3 carbon(s) represented by $X^1$, $X^2$, $X^3$, $X^4$ and $X^5$ of the formula (2a) in the europium complexes A and B, the fluoroalkyl group with 1 to 3 carbon(s) that is similar to $X^A$, $X^B$, $X^C$, $X^D$ and $X^E$ of the formula (B) can be exemplified.

As the fluoroalkyloxy group with 1 to 3 carbon(s) represented by $X^1$, $X^2$, $X^3$, $X^4$ and $X^5$ of the formula (2a) in the europium complexes A and B, the fluoroalkyloxy group with 1 to 3 carbon(s) that is similar to $X^A$, $X^B$, $X^C$, $X^D$ and $X^E$ of the formula (B) can be exemplified.

When one or more of $X^1$, $X^2$, $X^3$, $X^4$ and $X^5$ of the formula (2a) in the europium complexes A and B are a phenyl group, a substituted phenyl group that is similar to $X^A$, $X^B$, $X^C$, $X^D$ and $X^E$ of the formula (B) can be exemplified.

Among phenyl groups expressed with the formula (2a) in $R^3$ of the europium complexes A and B, it is preferable that $X^1$, $X^2$ and $X^3$ are independently a hydrogen atom, a methyl group or the formula (2b), respectively.

The phenyl group expressed with [the following formula (2b) is as follows]:

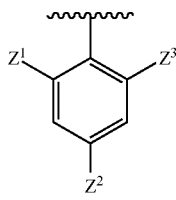

(2b)

[wherein, $Z^1$, $Z^2$ and $Z^3$ are independently a hydrogen atom, fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s) or phenyl group that may be substituted with a fluorine atom $X^4$ and $X^5$ are independently a hydrogen atom or a methyl group, respectively], and $X^4$ and $X^5$ are independently a hydrogen atom or a methyl group, respectively.]

As the alkyl group with 1 to 3 carbon(s) represented by $Z^1$, $Z^2$ and $Z^3$ of the formula (2b) in the europium complexes A and B, the alkyl group with 1 to 3 carbon(s) that is similar to $X^1$, $X^2$, $X^3$, $X^4$ and $X^5$ can be exemplified.

As the alkyloxy group with 1 to 3 carbon(s) represented by $Z^1$, $Z^2$ and $Z^3$ of the formula (2b) in the europium complexes A and B, the alkyloxy group with 1 to 3 carbon(s) that is similar to $X^1$, $X^2$, $X^3$, $X^4$ and $X^5$ can be exemplified.

As the aryloxy group with 6 to 10 carbons represented by $Z^1$, $Z^2$ and $Z^3$ of the formula (2b) in the europium complexes A and B, the aryloxy group with 6 to 10 carbons that is similar to $X^1$, $X^2$, $X^3$, $X^4$ and $X^5$ can be exemplified.

As the fluoroalkyl group with 1 to 3 carbon(s) represented by $Z^1$, $Z^2$ and $Z^3$ of the formula (2b) in the europium complexes A and B, the fluoroalkyl group with 1 to 3 carbon(s) that is similar to $X^1$, $X^2$, $X^3$, $X^4$ and $X^5$ can be exemplified.

As the fluoroalkyloxy group with 1 to 3 carbon(s) represented by $Z^1$, $Z^2$ and $Z^3$ of the formula (2b) in the europium complexes A and B, the fluoroalkyloxy group with 1 to 3 carbon(s) that is similar to $X^1$, $X^2$, $X^3$, $X^4$ and $X^5$ can be exemplified.

As the phenyl group that may be substituted with a fluorine atom represented by $Z^1$, $Z^2$ and $Z^3$ of the formula (2b) in the europium complexes A and B, a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 2,4,6-trifluorophenyl group, a 3,4,5-trifluorophenyl group, a perorophenyl group and the like can be exemplified.

As a substituent represented by $Z^1$, $Z^2$ and $Z^3$ of the formula (2b) in the europium complexes A and B, a hydrogen atom, a fluorine atom, a methyl group, a methoxy group, an isopropyloxy group, a trifluoromethyl group and a trifluoromethyloxy group are preferable in terms of good light resistance.

As a substituent represented by $X^1$, $X^2$, $X^3$, $X^4$ and $X^5$ of the formula (2b) in the europium complexes A and B, in terms of good light resistance, a hydrogen atom, a fluorine atom, an alkyl group with 1 to 3 carbon(s), a methoxy group, an isopropyloxy group, a phenyl group that may be substituted with an alkyl group with 1 to 3 carbon(s), a phenyl group that may be substituted with an alkyloxy group with 1 to 3 carbon(s), a phenyl group that may be substituted with a fluorine atom, a phenyl group that may be substituted with a linear fluoroalkyl group and a phenyl group that may be substituted with a linear fluoroalkyloxy group are preferable, and a hydrogen atom, a methyl group, an isopropyl group, a methoxy group, an isopropyloxy group, a 2,6-dimethoxyphenyl group, a 2,6-bis (isopropoxy) phenyl group, a 4-fluorophenyl group, a 4-trifluoromethylphenyl group, a 4-trifluoromethyloxyphenyl group and a phenyl group are further preferable.

As the substituent represented with $R^3$ of the formula (1) in the europium complex A, in terms of good light resistance, a cyclic secondary alkyl group with 3 to 10 carbons, a biphenyl group that may be substituted with a fluorine atom, a biphenyl group that may be substituted with a fluoroalkyl group with 1 to 3 carbon(s), a biphenyl group that may be substituted with a fluoroalkyloxy group with 1 to 3 carbon(s), phenyl group that may be substituted with a fluorine atom, a phenyl group that may be substituted with a linear fluoroalkyl group and a phenyl group that may be substituted with a fluoroalkyloxy group with 1 to 3 carbon(s) are preferable, and a cyclohexyl group, a phenyl group, a 2-methylphenyl group, a 2-biphenyl group, a 2',6'-dimethoxybiphenyl-2-yl group, a 2',6'-bis (isopropoxy) biphenyl-2-yl group, a 2',4',6'-triisopropylbiphenyl-2-yl group, a 4'-fluorobiphenyl-2-yl group, a 4'-(trifluoromethyl) biphenyl-2-yl group, and a 4'-(trifluoromethyloxy) biphenyl-2-yl group are further preferable.

As the substituent represented with $R^2$ and $R^3$ of the formula (1) in the europium complex B, in terms of good light resistance, a biphenyl group that may be substituted with a fluorine atom, a biphenyl group that may be substituted with a fluoroalkyl group with 1 to 3 carbon(s), a biphenyl group that may be substituted with a fluoroalkyloxy group with 1 to 3 carbon(s), a phenyl group that may be substituted with a fluorine atom, a phenyl group that may be substituted with a linear fluoroalkyl group and a phenyl group that may be substituted with a fluoroalkyloxy group with 1 to 3 carbon(s) are preferable, and a phenyl group, a 2-methylphenyl group, a 2-biphenyl group, a 2',6'-dimethoxybiphenyl-2-yl group, a 2',6'-bis (isopropoxy) biphenyl-2-yl group, a 2',4',6'-triisopropylbiphenyl-2-yl group, a 4'-fluorobiphenyl-2-yl group, a 4'-(trifluoromethyl) biphenyl-2-yl group and a 4'-(trifluoromethyloxy) biphenyl-2-yl group are further preferable.

$R^4$ of the formula (1) in the europium complexes A and B represent a hydrogen atom, a deuterium atom or a fluorine atom, and a hydrogen atom is preferable in terms of availability.

'n' of the formula (1) in the europium complexes A and B represents an integer of 1 to 3, and it is preferable that 'n' is 2 in terms of good light resistance in the europium complexes A and B.

As the alkyl group with 1 to 6 carbon(s) represented by $W^1$ and $W^2$ of the formula (1) in the europium complexes A and B, any of linear, branched and cyclic ones are acceptable, and specifically, a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-ethylpropyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, a 2-cyclobutylethyl group and the like can be exemplified.

As the fluoroalkyl group with 1 to 6 carbon(s) represented by $W^1$ and $W^2$ of the formula (1) in the europium complexes A and B, any of linear, branched and cyclic ones are acceptable, a trifluoromethyl group, a difluoromethyl group, a perfluoroethyl group, a 2,2,2-trifluoroethyl group, a 1,1-difluoroethyl group, a 2,2-difluoroethyl group, a perfluoropropyl group, a 2,2,3,3,3-pentafluoropropyl group, a 2,2,3,3-tetrafluoropropyl group, a 3,3,3-trifluoropropyl group, a 1,1-difluoropropyl group, a 1,1,1,2,3,3,3-hexafluoro-2-propyl group, a 2,2,2-trifluoro-1-(trifluoromethyl) ethyl group, a perfluorobutyl group, a 2,2,3,3,4,4,4-heptafluorobutyl group, a 3,3,4,4,4-pentafluorobutyl group, a 4,4,4-trifluorobutyl group, a 1,2,2,3,3,3-hexafluoro-1-(trifluoromethyl) propyl group, a 1-(trifluoromethyl) propyl group, a 1-methyl-3,3,3-trifluoropropyl group, a perfluoropentyl group, a 2,2,3,3,4.4.5.5.5-nonafluoropentyl group, a 3,3,4.4.5.5.5-heptafluoropentyl group, a 4.4.5.5.5-pentafluoropentyl group, a 5,5,5-trifluoropentyl group, a 1,2,2,3,3,3-hexafluoro-1-(1,1,2,2,2-pentafluoroethyl) propyl group, a 1,2,2,3,3,4,4,4-octafluoro-1-(trifluoromethyl) butyl group, a 1,1,2,3,3,4,4,4-octafluoro-2-(trifluoromethyl) butyl group, a 1,1,2,2,3,4,4,4-octafluoro-3-(trifluoromethyl) butyl group, a 1,1,3,3,3-pentafluoro-2,2-bis (trifluoromethyl) propyl group, a 2,2,3,3,3-pentafluoro-1,1-bis (trifluoromethyl) propyl group, a perfluorocyclopentyl group, a perfluorohexyl group, a 1,2,2,3,3,4.4.5.5.5-decafluoro-1-(trifluoromethyl) pentyl group, a 1,1,2,3,3,4.4.5.5.5-decafluoro-2-(trifluoromethyl) pentyl group, a 1,1,2,2,3,4,4,5,5,5-decafluoro-3-(trifluoromethyl) pentyl group, a 1,1,2,2,3,3,4,5,5,5-decafluoro-4-(trifluoromethyl) pentyl group, a 2,2,3,3,4,4,4-heptafluoro-1,1-bis (trifluoromethyl) butyl group, a 1,2,3,3,4,4,4-heptafluoro-1,2-bis (trifluoromethyl) butyl group, a 1,2,2,3,4,4,4-heptafluoro-1,3-bis (trifluoromethyl) butyl group, a 1,1,3,3,4,4,4-heptafluoro-2,2-bis (trifluoromethyl) butyl group, a 1,2,2,3,4,4,4-heptafluoro-2,3-bis (trifluoromethyl) butyl group, a 1,1,2,2.4,4,4-heptafluoro-3,3-bis (trifluoromethyl) butyl group, a perfluorocyclohexyl group, a perfluorocyclopentylmethyl group and the like can be exemplified.

As the substituent represented by $W^1$ and $W^2$ of the formula (1) in the europium complexes A and B, in terms of good light resistance, a perfluoroalkyl group with 1 to 6 carbon(s) is preferable, and a trifluoromethyl group, a perfluoroethyl group and a perfluoropropyl group are further preferable.

In the europium complexes A and B, the europium complex A is preferable in terms of manufacturing at low cost.

As the europium complex A, it is preferable that both $R^1$ and $R^2$ are a cyclopentyl group or a cyclohexyl group, and it is particularly preferable that $R^1$, $R^2$ and $R^3$ are all a cyclopentyl group or a cyclohexyl group.

As the europium complex A, specifically structures expressed with the following (1-1) to (1-21) can be exemplified:

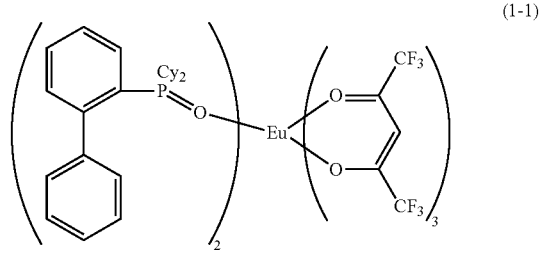

(1-1)

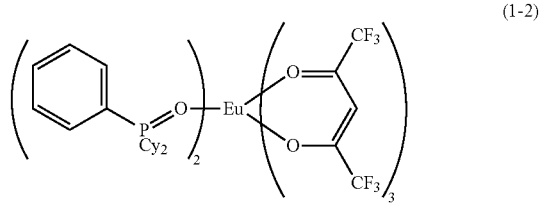

(1-2)

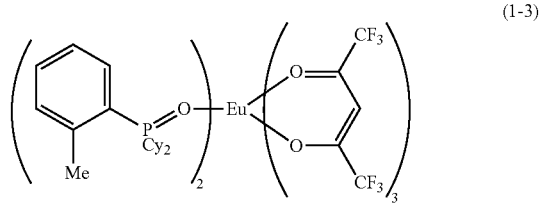

(1-3)

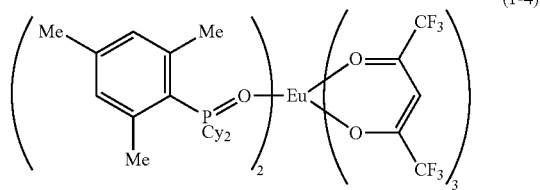

(1-4)

(1-5)
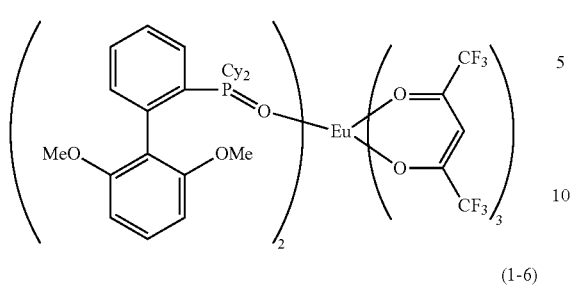
(1-6)
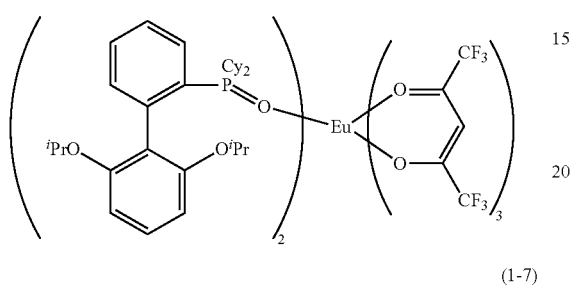
(1-7)
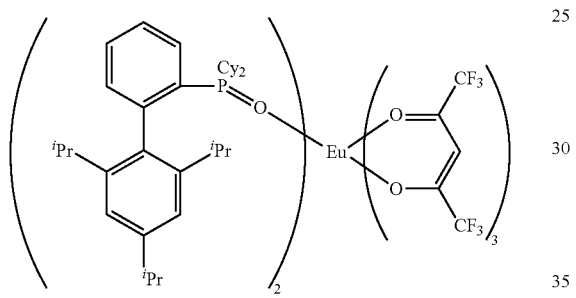
(1-8)
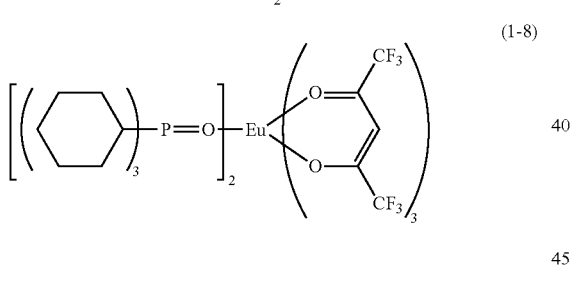
(1-9)
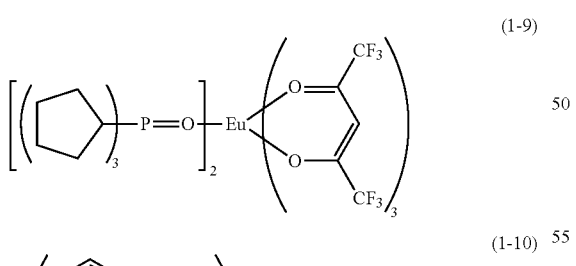
(1-10)
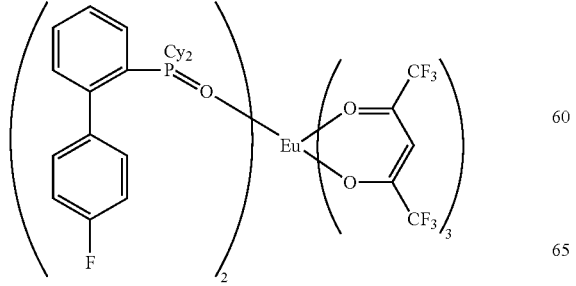
(1-11)
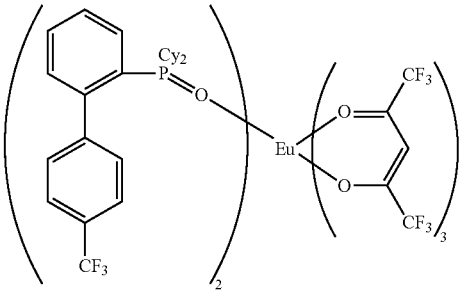
(1-12)
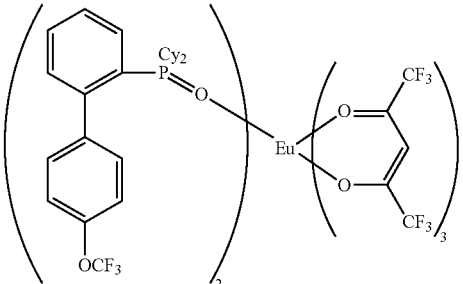
(1-13)
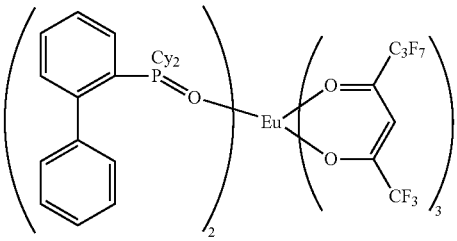
(1-14)
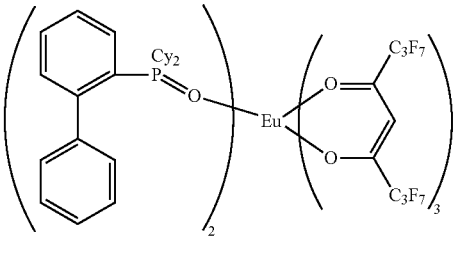
(1-15)
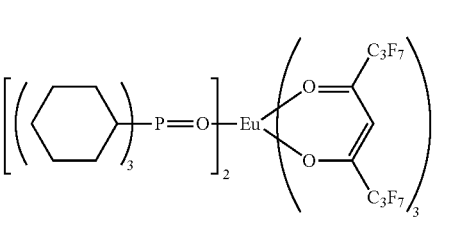
(1-16)
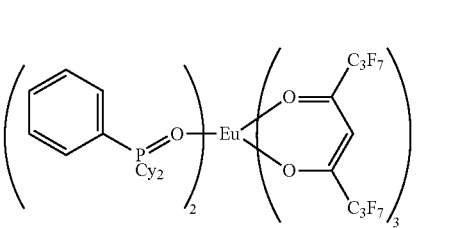

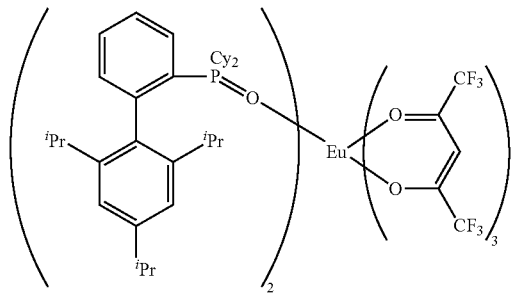
(1-17)

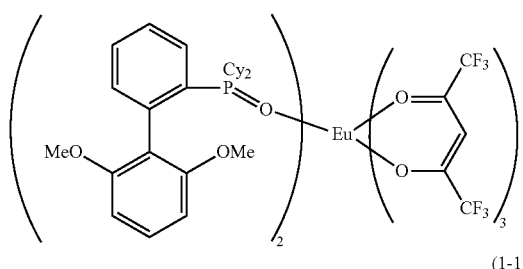
(1-18)

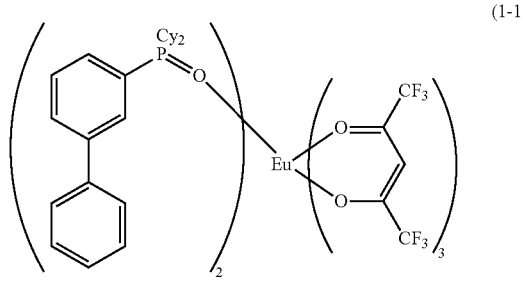
(1-19)

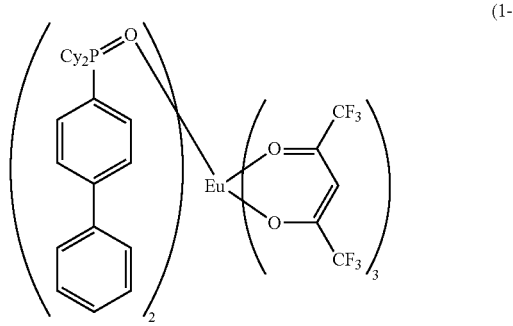
(1-20)

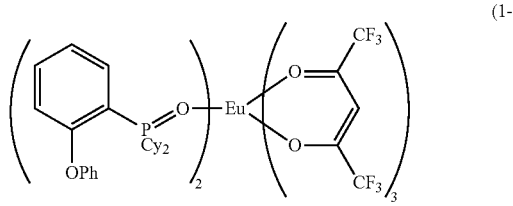
(1-21)

Among the compounds expressed with (1-1) to (1-21), (1-1) to (1-8) are preferable as the europium complex B in terms of good light resistance, and (1-8) is further preferable because it can be easily synthesized from phosphorus trichloride, which is an inexpensive raw material, via phosphine oxide (4-8), and, the manufacturing cost is low.

Next, a manufacturing method for the europium complexes A and B is explained.

As the manufacturing method for the europium complexes A and B, Method 1, which is characterized by reacting phosphine oxide expressed with the formula (4) (hereafter, referred to as phosphine oxide (4)), β-diketone expressed with the formula (3) (hereafter, referred to as β-diketone (3)) and europium salt, can be exemplified.

(Method 1)

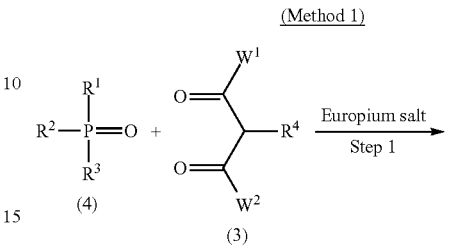

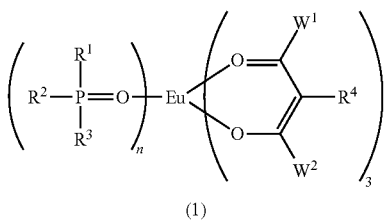
(1)

(wherein, $R^1$, $R^2$, $R^3$, $R^4$, n, $W^1$ and $W^2$ have the same meanings as those of $R^1$, $R^2$, $R^3$, $R^4$, n, $W^1$ and $W^2$ of the formula (1), respectively.)

The phosphine oxide (4) that is used for Method 1 can be obtained with a method described in Chemical Reviews, Vol. 60, pp. 243-260, 1960 or the like.

As the phosphine oxide (4) that is used for Method 1, specifically, structures expressed with the following (4-1) to (4-21) can be exemplified.

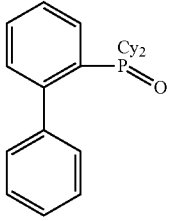
(4-1)

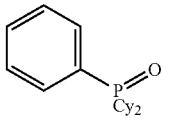
(4-2)

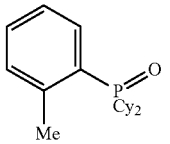
(4-3)

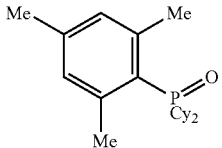
(4-4)

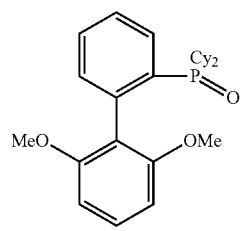
(4-5)
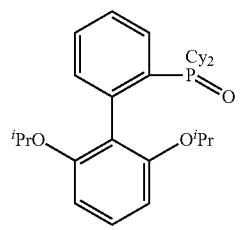
(4-6)
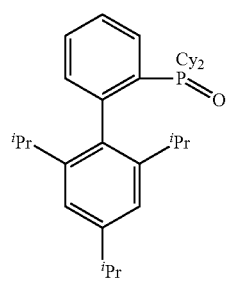
(4-7)
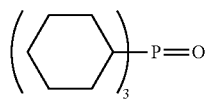
(4-8)
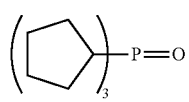
(4-9)
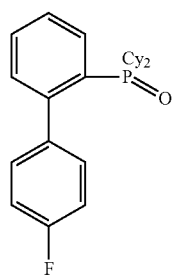
(4-10)
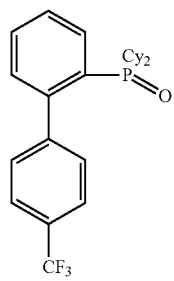
(4-11)
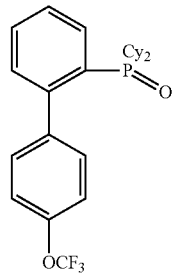
(4-12)
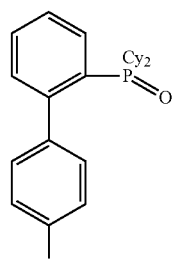
(4-13)
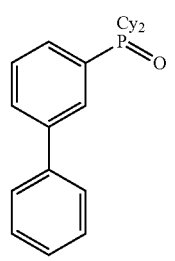
(4-14)
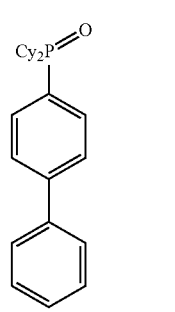
(4-15)
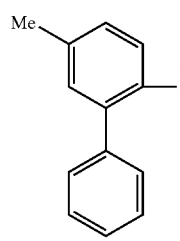
(4-16)
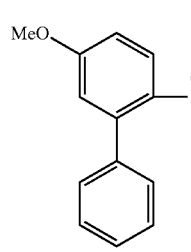
(4-17)

-continued (4-19)
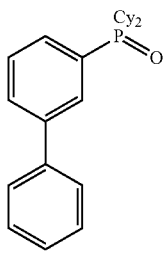

(4-20)
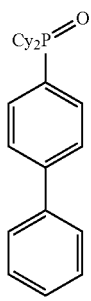

(4-21)
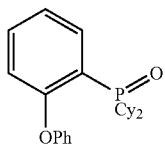

Among the compounds expressed with (4-1) to (4-21), as the phosphine oxide (4), the compounds expressed with (4-1) to (4-3) or (4-5) to (4-9) are preferred in terms of good reaction yield.

As the β-diketone (3) that is used for Method 1, specifically, hexafluoroacetylacetone (Hhfa), 1,1,1,5,5,6,6,6-octafluoro-2,4-hexanedione, 1,1,5,5-tetrafluoro-2,4-pentanedione, 1,1,1,2,2,3,3,7,7,8,8,9,9,9-tetradeca-fluoro-4,6-nonanedione (Htdfn), 8H,8H-perfluoropentadecane-7,9-dione, trifluoroacetylacetone, 2,2-dimethyl-6,6,7,7,8,8,8-heptafluoro-3,5-octanedione, acetyl acetone, 4,4,4-trifluoro-1-(2-thienyl)-1,3-butanedione, 4,4,4-trifluoro-1-phenyl-1,3-butanedione, 1,3-diphenyl-1,3-propanedione and the like can be exemplified.

The β-diketone (3) that is used for Method 1 can be obtained, for example, with the method described in Journal of the American Chemical Society, Vol. 66, pp. 1220-1222, 1994 or the like. Further, commercially available products can be used. The β-diketone (3) has an active hydrogen atom, and will become an anionic ligand after losing a hydrogen ion. For example, hfa represents an anionic ligand where a hydrogen ion has been lost from Hhfa, and tdfn represents an anionic ligand where a hydrogen ion has been lost from Htdfn.

The β-diketone (3) causes an intramolecular hydrogen transfer to enable formation of enol (3a) or enol (3b), but the β-diketone (3) contains both enols. Herein, the β-diketone (3) is described as the formula (3).

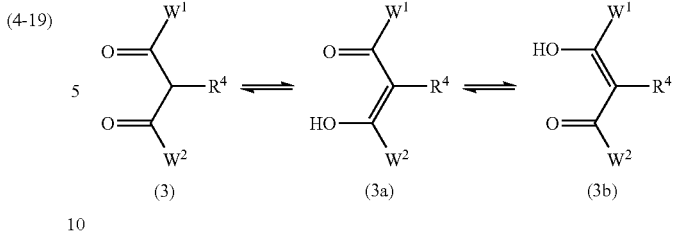

As the europium salt that is used in Method 1, for example, halide salts, such as europium (III) fluoride, europium (III) chloride, europium (III) bromide or europium (III) iodide, or their hydrates; organic acid salts, such as europium (III) oxalate, europium (III) acetate, europium (III) trifluoro acetate or europium (III) trifluoromethanesulfonate, or their hydrates; metallic alkoxides, such as tris [N,N-bis (trimethylsilyl) amide] europium (III), europium (III) trimethoxide, europium (III) triethoxide or europium (III) tri (2-propoxide); and inorganic acid salts, such as europium (III) phosphate, europium (III) sulfate or europium (III) nitrate, or their hydrates can be exemplified. Among these, organic acid salts, such as europium chloride (III), europium (III) nitrate, europium (III) oxalate, europium (III) acetate, europium (III) trifluoro acetate or europium (III) trifluoromethanesulfonate, are preferable in terms of good reaction yield, and europium (III) acetate, europium chloride (III) and europium (III) nitrate are further preferable.

In Method 1, it is preferable to implement [such process] in a solvent in terms of the good reaction yield of the europium complexes A and B. Types of usable solvents are not particularly limited as long such solvents do not interfere with a reaction. As examples of the usable solvents, halogenated hydrocarbons, such as dichloromethane, chloroform or chlorobenzene; alcohols, such as methanol, ethanol, propanol or isopropyl alcohol; esters, such as methyl acetate, ethyl acetate, butyl acetate or isoamyl acetate; glycol ethers, such as ethylene glycol monoethyl ether, ethylene glycol monomethyl ether or ethylene glycol monobutyl ether; ethers, such as diethyl ether, tert-butyl methyl ether, glyme, diglyme, triglyme, tetrahydrofuran or cyclopentyl methyl ether; ketones, such as tert-butyl methyl ketone, isobutyl methyl ketone, ethyl butyl ketone, dipropyl ketone, diisobutyl ketone, cyclohexanone or acetone; hydrocarbons, such as hexane, cyclohexane, ethylcyclohexane, heptane, octane, benzene, toluene or xylene; and water can be exemplified. These solvents can be used singularly or by mixing two types or more at an arbitrary ratio. For the europium complexes A and B, in terms of good reaction yield of these, dichloromethane, chloroform, methanol or ethanol is preferable.

Next, in Method 1, as usages of the europium salt and the phosphine oxide (4), it is preferable to use 0.5 to 5.0 moles of the phosphine oxide (4), and it is further preferable to use 1.0 to 3.0 moles, with respect to 1 mole of the europium salt.

Further, in Method 1, as usages of the europium salt and the β-diketone (3), it is preferable to use 1.0 to 10 moles of the β-diketone (3), and it is further preferable to use 2.0 to 8.0 moles, with respect to 1 mole of the europium salt.

In Method 1, a reaction temperature and a reaction time are not particularly limited, and ordinary conditions at the time of manufacturing metal complexes can be used. As a specific example, the europium complexes A and B can be manufactured with a good yield at a reaction temperature that is appropriately selected from a range of temperature from −80° C. to 120° C., by selecting a reaction time that is appropriately selected from a range of time period from 1 minute to 120 hours.

The europium complexes A and B manufactured with Method 1 can be refined by using an appropriately selected ordinary refining method at the time of refining metal complexes. As a specific refining method, filtration, extraction, centrifugal separation, decantation, distillation, sublimation, crystallization, column chromatography and the like can be exemplified.

(Method 2)

Further, as a manufacturing method for the europium complexes A and B, Method 2, which is characterized by reacting a diketonato complex (5) and phosphine oxide (4), can be exemplified, as well.

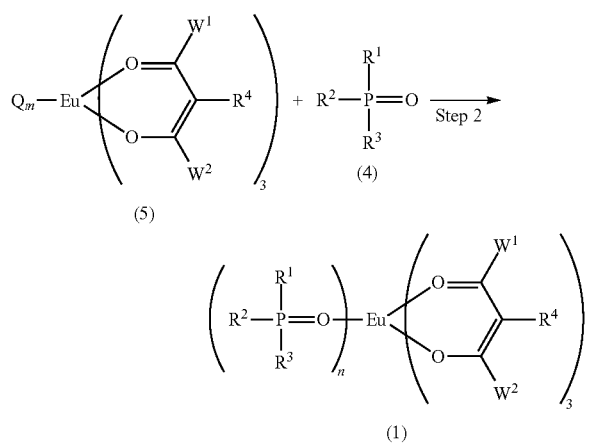

(wherein, $R^1$, $R^2$, $R^3$, $R^4$, n, $W^1$ and $W^2$ have the same meanings as those of $R^1$, $R^2$, $R^3$, $R^4$, n, $W^1$ and $W^2$ of the formula (1), respectively. Q represents a coordinated molecule. 'm' represents a number of 0 to 3.)

In Method 2, the coordinated molecule represented by Q is not limited as long as it would not interfere with reactions, and specifically, water, heavy water, tetrahydrofuran, pyridine, imidazole, acetone, methanol, ethanol, propanol, isopropyl alcohol, nitrile, such as acetonitrile or propionitrile, ammonia, amine, such as diethylamine or triethylamine, ether, such as dimethyl ether, diethyl ether or tetrahydrofuran, and the like can be exemplified, and water is preferable in terms of easy synthesis of the diketonato complex (5).

'm' in the formula (5) represents an integer of 0 to 3 and is preferably 2 in terms of easy synthesis.

The diketonato complex (5) that is used for Method 2 can be obtained using a method described in Reference Example 1 herein, or another method described in Journal of the American Chemical Society, Vol. 87, pp. 5254-5256, 1965, or the like.

As the specific examples of the diketonato complex (5) that is used in Method 2, tris (hexafluoroacetylacetonato) europium (III), tris (1,1,1,5,5,6,6,6-octafluoro-2,4-dioxohexane-3-ido) europium (III), tris (1,1,5,5-tetrafluoro-2,4-dioxopentane-3-ido) europium (III), tris (1,1,1,2,2,3,3,7,7,8,8,9,9,9-tetradeca-fluoro-4,6-dioxononane-5-ido) europium (III), tris (1,1,1,2,2,3,3,4,4,5,5,6,6,10,10,11,11,12,12,13,13,14,14,15,15,15-hexacosafluoro-7,9-dioxopentadecane-8-ido) europium (III), tris (trifluoroacetylacetonato) europium (III), tris [4,4,4-trifluoro-1-(2-thienyl)-1,3-dioxobutane-2-ido] europium (III), tris (4,4,4-trifluoro-1-phenyl-1,3-dioxobutane-2-ido) europium (III), tris (1,3-diphenyl-1,3-dioxopropane-2-ido) europium (III) and their hydrates and the like can be exemplified.

The phosphine oxide (4) that is used for Method 2 can be obtained using a method described in Reference Example 3 herein, another method described in Chemical Reviews, Vol. 60, pp. 243-260, 1960, another method described in Organic Letters, Vol. 13, pp. 3478-3481, 2011 or the like.

As phosphine oxide (4) that is used for Method 2, the same one exemplified in the description for Method 1 can be exemplified. In Method 2, it is preferable that R', $R^2$ and $R^3$ are a cyclohexyl group in terms of good yield.

It is preferable that Method 2 is implemented in a solvent in terms of good reaction yield of the europium complexes A and B. Types of usable solvents are not particularly limited as long as these do not interfere with reactions. As examples of the usable solvents, halogenated hydrocarbons, such as dichloromethane, chloroform or chlorobenzene; alcohols, such as methanol, ethanol, propanol or isopropyl alcohol; esters, such as ethyl acetate, butyl acetate or isoamyl acetate; glycol ethers, such as ethylene glycol monoethyl ether, ethylene glycol monomethyl ether or ethylene glycol monobutyl ether; ethers, such as diethyl ether, tert-butyl methyl ether, glyme, diglyme, triglyme or tetrahydrofuran; ketones, such as tert-butyl methyl ketone, isobutyl methyl ketone, ethyl butyl ketone, dipropyl ketone, diisobutyl ketone, cyclohexanone or acetone; hydrocarbons, such as hexane, cyclohexane, ethylcyclohexane, heptane, octane, benzene, toluene or xylene; and water can be exemplified. These solvents can be used singularly, or can be used by mixing two or more types in an arbitrary ratio. As the solvents, dichloromethane, chloroform, methanol and ethanol are preferable in terms of good reaction yield of the europium complexes A and B.

Next, as usages of the diketonato complex (5) and the phosphine oxide (4) at the time of conducting Method 2, it is preferable to use 0.5 to 5.0 moles of the phosphine oxide (4), and it is further preferable to use 1.0 to 3.0 moles, with respect to 1 mole of the diketonato complex (5).

In Method 2, the reaction temperature and the reaction time are not particularly limited, and ordinary conditions at the time of manufacturing metal complexes can be used. As a specific example, the europium complexes A and B can be manufactured with a good yield at a reaction temperature that is appropriately selected from a range of temperature from −80° C. to 120° C., by selecting a reaction time that is appropriately selected from a range of time period from 1 minute to 120 hours.

The europium complexes A and B manufactured with Method 2 can be refined by selecting and using a normal refining method at the time of manufacturing metal complexes. As a specific refining method, filtration, extraction, centrifugal separation, decantation, distillation, sublimation, crystallization, column chromatography and the like can be exemplified.

(Europium Complex C)

Next, a europium complex C is explained.

Definitions of $Z^4$, $Z^5$, $Z^6$, $R^5$, $R^6$, $R^7$, $R^8$, $R^9$, $W^3$ and $W^4$ in the europium complex C expressed with the formula (6) are as mentioned below.

As an alkyl group with 1 to 3 carbon(s) represented by $Z^4$, $Z^5$ and $Z^6$ of the formula (6), the alkyl group with 1 to 3 carbon(s) that is similar to $X^F$ of the formula (Ba) can be exemplified.

As an alkyloxy group with 1 to 3 carbon(s) represented by $Z^4$, $Z^5$ and $Z^6$ of the formula (6), the alkyloxy group with 1 to 3 carbon(s) that is similar to $X^F$ of the formula (Ba) can be exemplified.

As a fluoroalkyl group with 1 to 3 carbon(s) represented by $Z^4$, $Z^5$ and $Z^6$ of the formula (6), the fluoroalkyl group with 1 to 3 carbon(s) that is similar to $X^F$ of the formula (Ba) can be exemplified.

As a fluoroalkyloxy group with 1 to 3 carbon(s) represented by $Z^4$, $Z^5$ and $Z^6$ of the formula (6), the fluoroalkyloxy group with 1 to 3 carbon(s) that is similar to $X^F$ of the formula (Ba) can be exemplified.

As a naphthyl group that may be substituted with a fluorine atom represented by $Z^4$, $Z^5$ and $Z^6$ of the formula (6), the naphthyl group that may be substituted with a fluorine atom that is similar to $X^F$ of the formula (Ba) can be exemplified.

As a pyridyl group that may be substituted with a fluorine atom represented by $Z^4$, $Z^5$ and $Z^6$ of the formula (6), the pyridyl group that may be substituted with a fluorine atom that is similar to $X^F$ of the formula (Ba) can be exemplified.

As an alkyl group with 1 to 3 carbon(s) represented by $R^5$, $R^7$ and $R^9$ of the formula (7), the alkyl group with 1 to 3 carbon(s) that is similar to $Z^4$, $Z^5$ and $Z^6$ can be exemplified.

As an alkyloxy group with 1 to 3 carbon(s) represented by $R^5$, $R^7$ and $R^9$ of the formula (7), the alkyloxy group with 1 to 3 carbon(s) that is similar to $Z^4$, $Z^5$ and $Z^6$ can be exemplified.

As a fluoroalkyl group with 1 to 3 carbon(s) represented by $R^5$, $R^7$ and $R^9$ of the formula (7), the fluoroalkyl group with 1 to 3 carbon(s) that is similar to $Z^4$, $Z^5$ and $Z^6$ can be exemplified.

As a fluoroalkyloxy group with 1 to 3 carbon(s) represented by $R^5$, $R^7$ and $R^9$ of the formula (7), the fluoroalkyloxy group with 1 to 3 carbon(s) that is similar to $Z^4$, $Z^5$ and $Z^6$ can be exemplified.

As a phenyl group that may be substituted with a fluorine atom represented by $R^5$, $R^7$ and $R^9$ of the formula (7), a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 2,4,6-trifluorophenyl group, a 3,4,5-trifluorophenyl group, a perfluorophenyl group and the like can be exemplified.

As a substituent represented by $R^5$, $R^7$ and $R^9$ of the formula (7), a hydrogen atom, a fluorine atom, an alkyl group with 1 to 3 carbon(s), an alkyloxy group with 1 to 3 carbon(s), a fluoroalkyl group with 1 to 3 carbon(s), a fluoroalkyloxy group with 1 to 3 carbon(s) and a phenyl group are preferable in terms of good light resistance. A hydrogen atom, a fluorine atom, a trifluoromethyl group and a trifluoromethyloxy group are further preferable. As $R^6$ and $R^8$ of the formula (7), a hydrogen atom is preferable in terms of easy availability.

As the substituent represented by $Z^4$, $Z^5$ and $Z^6$ of the formula (6), a linear alkyl group, a linear alkyloxy group, a biphenyl group, a phenyl group that may be substituted with a fluorine atom, a phenyl group that may be substituted with a linear fluoroalkyl group and a phenyl group that may be substituted with a linear fluoroalkyloxy group are preferable in terms of good light resistance, and a methyl group, a methyloxy group, a 4-fluorophenyl group, a 4-trifluoromethylphenyl group and a 4-trifluoromethyloxyphenyl group are further preferable.

As an alkyl group with 1 to 6 carbon(s) represented by $W^3$ and $W^4$ of the formula (6), the alkyl group with 1 to 6 carbon(s) that is similar to $W^A$ and $W^B$ of the formula (A) can be exemplified.

As a fluoroalkyl group with 1 to 6 carbon(s) represented by $W^3$ and $W^4$ of the formula (6), the fluoroalkyl group with 1 to 6 carbon(s) that is similar to $W^A$ and $W^B$ of the formula (A) can be exemplified.

As the substituent represented by $W^3$ and $W^4$ of the formula (6), a perfluoroalkyl group with 1 to 6 carbon(s) is preferable in terms of good light resistance, and a trifluoromethyl group, a perfluoroethyl group and a perfluoropropyl group are further preferable.

As the europium complex C, specifically, the structures expressed with the following (6-1) to (6-23) can be exemplified:

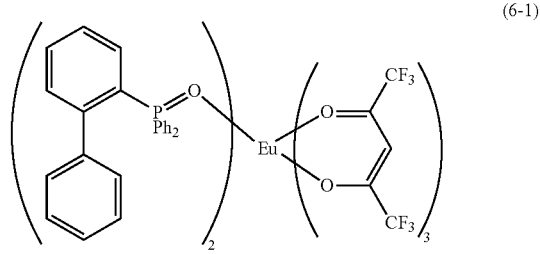

(6-1)

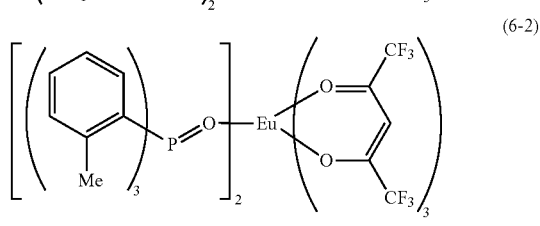

(6-2)

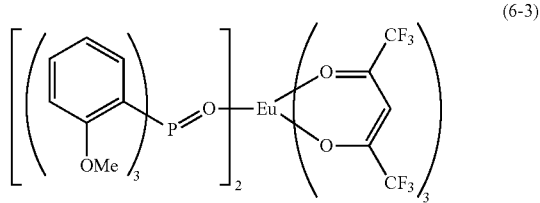

(6-3)

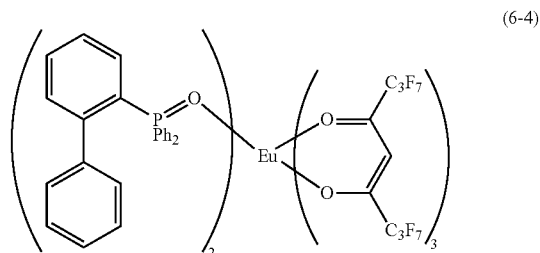

(6-4)

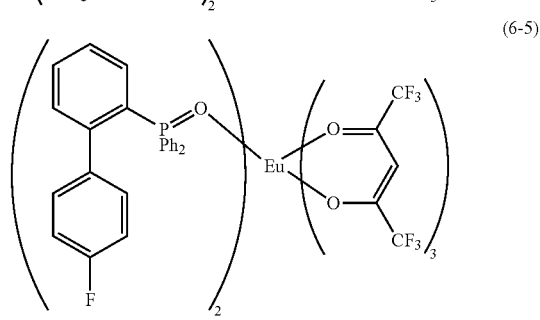

(6-5)

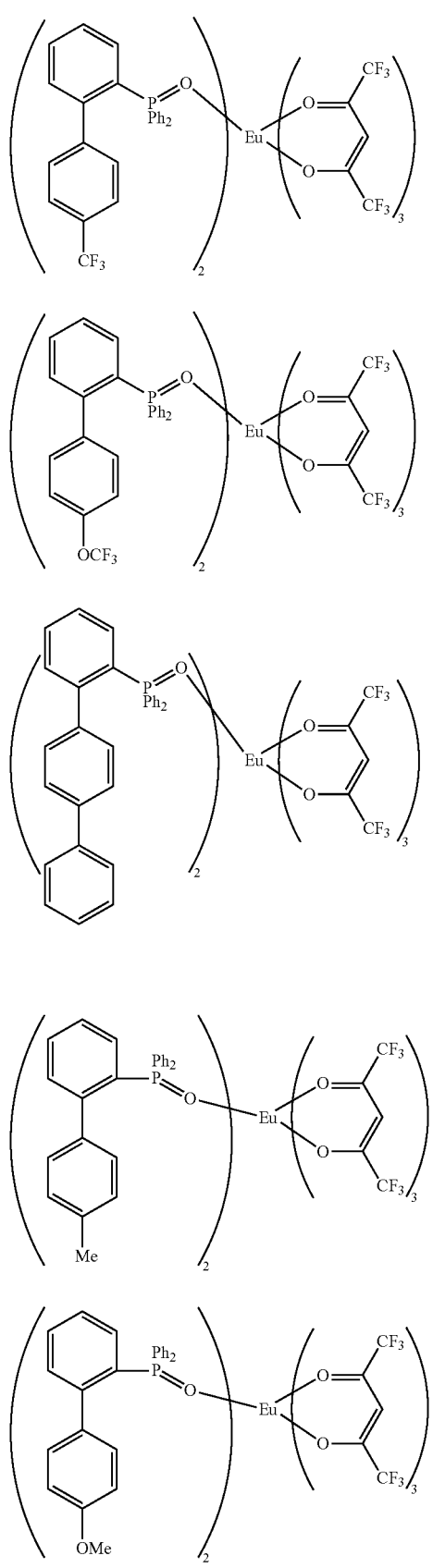
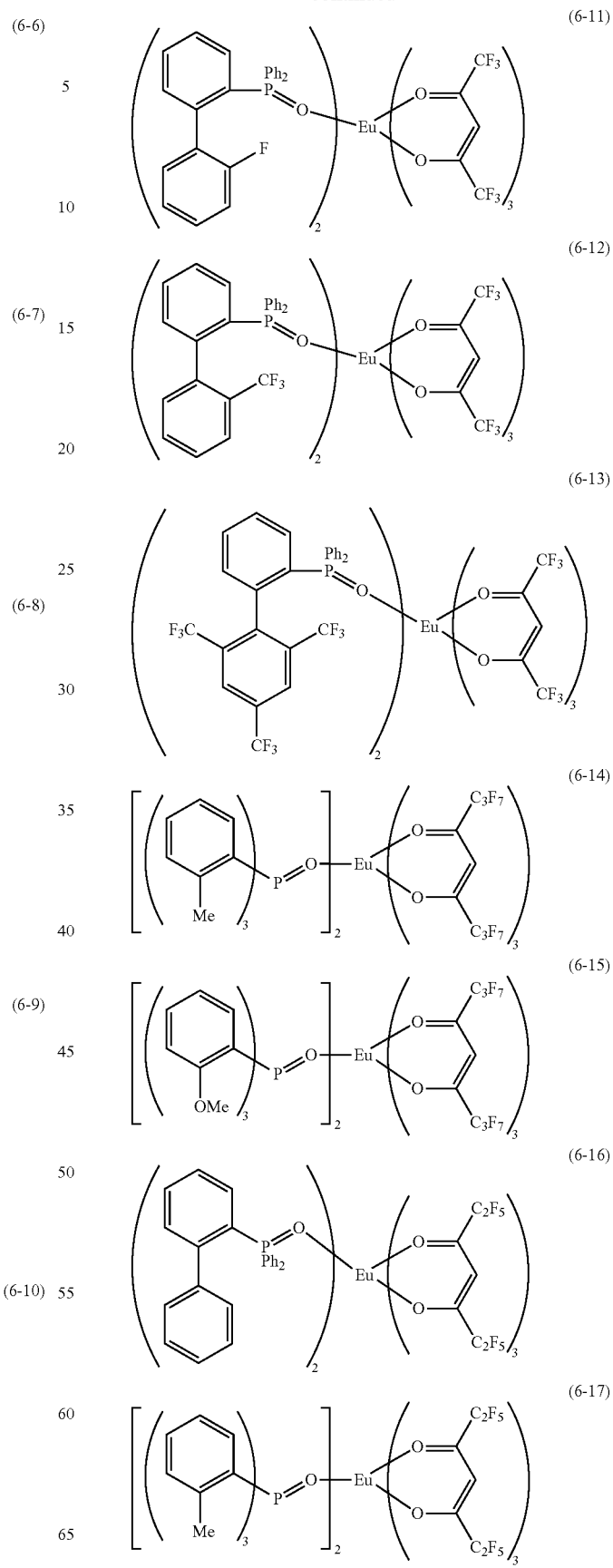

(6-18)
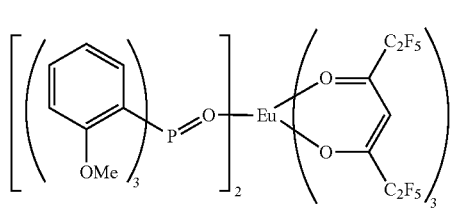

(6-19)
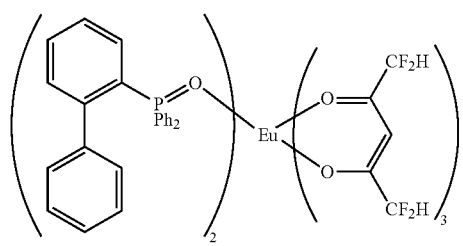

(6-20)
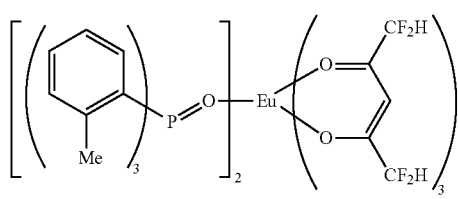

(6-21)
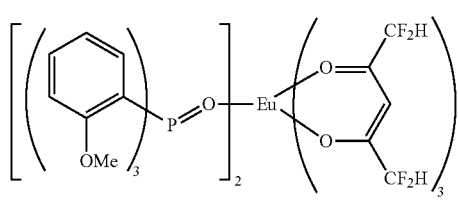

(6-22)
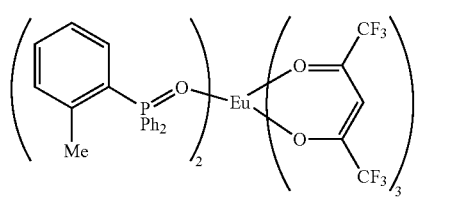

(6-23)
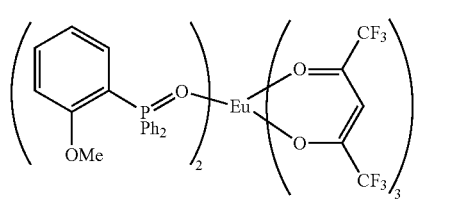

Among the compounds expressed with (6-1) to (6-23), (6-1) to (6-7), (6-11) to (6-18), (6-22) and (6-23) are preferable in terms of good light resistance, and (6-1) to (6-7), (6-22) and (6-23) are further preferable.

(Method 3)

Next, a manufacturing method for the europium complex C is explained. The europium complex C can be manufactured in accordance with Method 3 where europium salt, β-diketone (8) and phosphine oxide (9) are reacted.

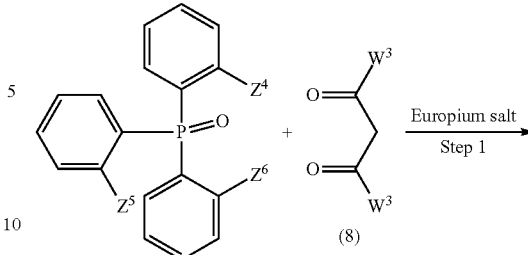

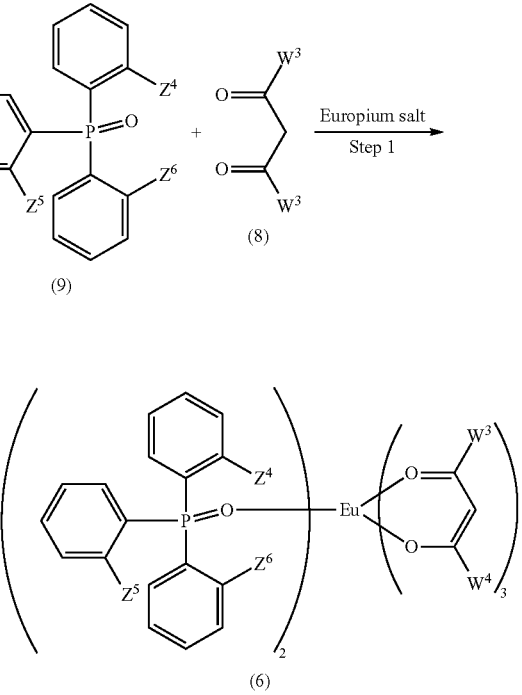

(wherein, $Z^4$, $Z^5$, $Z^6$, $W^3$ and $W^4$ have the same meanings as those of $Z^4$, $Z^5$, $Z^6$, $W^3$ and $W^4$ of the formula (6).)

Method 3 is a method for manufacturing the europium complex C by reacting europium salt, the β-diketone (8) and the phosphine oxide (9), and the europium complex C can be obtained with a good yield by applying a synthesis condition described, for example, in Chemical Communications, No. 5, pp. 520-521, 2002.

As the europium salt that is used in Method 3, for example, halide salts, such as europium (III) fluoride, europium (III) chloride, europium (III) bromide or europium (III) iodide, and their hydrates; organic acid salts, such as europium (III) oxalate, europium (III) acetate, europium (III) trifluoro acetate or europium (III) trifluoromethanesulfonate, and their hydrates; metallic alkoxides, such as tris [N,N-bis (trimethylsilyl) amide] europium (III), europium (III) trimethoxide, europium (III) triethoxide or europium (III) tri (2-propoxide); inorganic acid salts, such as europium (III) phosphate, europium (III) sulfate or europium (III) nitrate, and their hydrates can be exemplified.

Among these, in terms of good reaction yield, europium (III) chloride and europium (III) nitrate; or organic acid salts, such as europium (III) oxalate, europium (III) acetate, europium (III) trifluoro acetate or europium (III) trifluoromethanesulfonate are preferable, and europium (III) acetate, europium (III) chloride and europium (III) nitrate are further preferable.

Phosphine oxide (9) that is used for Method 3 can be obtained using a method described in Reference Example 18 herein or another method described in Chemical Reviews, Vol. 60, pp. 243-260, 1960, or the like.

As the phosphine oxide (9) that is used for Method 3, specifically structures expressed with the following (9-1) to (9-11) can be exemplified:

(9-1) 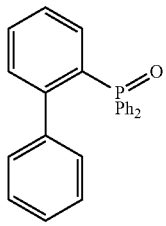

(9-2) 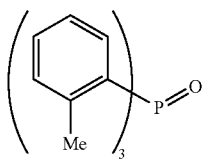

(9-3) 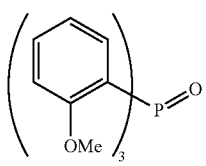

(9-4) 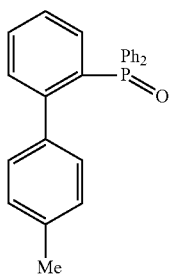

(9-5) 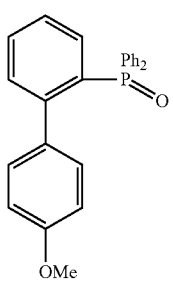

(9-6) 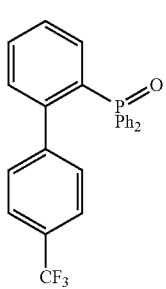

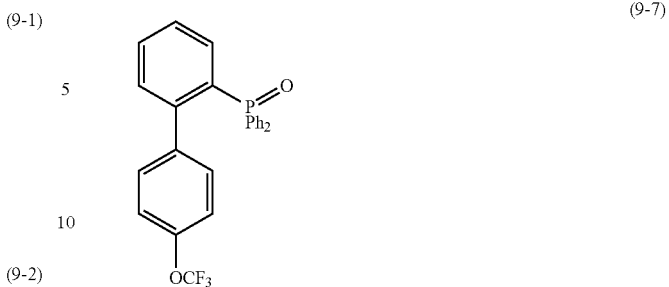

Among the compounds expressed with (9-1) to (9-11), as the phosphine oxide (9), the compounds expressed with (9-1) to (9-3) are preferable in terms of inexpensive raw materials.

As the β-diketone (8) that is used in Method 3, specifically, hexafluoroacetylacetone (Hhfa), 1,1,1,5,5,6,6,6-octafluoro-2,4-hexanedione, 1,1,5,5-tetrafluoro-2,4-pentanedione, 1,1,1,2,2,3,3,7,7,8,8,9,9,9-tetradeca-fluoro-4,6-nonanedione (Htdfn), 8H,8H-perfluoropentadecane-7,9-dione, trifluoroacetylacetone, 2,2-dimethyl-6,6,7,7,8,8,8-heptafluoro-3,5-octanedione, acetylacetone, 4,4,4-trifluoro-1-(2-thienyl)-1,3-butanedione, 4,4,4-trifluoro-1-phenyl-1,3-butanedione, 1,3-diphenyl-1,3-propanedione and the like can be exemplified. The β-diketone (8) that is used for Method 3 can be obtained by using, for example, a method described in Journal of the American Chemical Society, Vol.

66, pp. 1220-1222, 1994 or the like. Further, commercially available products can be used, as well. The β-diketone (8) has an active hydrogen ion, and that hydrogen ion is lost to become an anionic ligand. For example, hfa represents an anionic ligand where a hydrogen ion has been lost from Hhfa, and tdfn represents an anionic ligand where a hydrogen ion has been lost from Htdfn.

The manufacturing method in Method 3 is preferably implemented in a solvent(s) in terms of producing good yield of the europium complex C. Types of usable solvents are not particularly limited as long as these do not interfere with reactions. As examples of the usable solvents, halogenated hydrocarbons, such as dichloromethane, chloroform or chlorobenzene; alcohols, such as methanol, ethanol, propanol or isopropanol; esters, such as ethyl acetate, butyl acetate or isoamyl acetate; glycol ethers, such as ethylene glycol monoethyl ether, ethylene glycol monomethyl ether or ethylene glycol monobutyl ether; ethers, such as diethyl ether, tert-butyl methyl ether, glyme, diglyme, triglyme or tetrahydrofuran; ketones, such as tert-butyl methyl ketone, isobutyl methyl ketone, ethyl butyl ketone, dipropyl ketone, diisobutyl ketone, cyclohexanone or acetone; hydrocarbons, such as hexane, cyclohexane, ethylcyclohexane, heptane, octane, benzene, toluene or xylene; and water can be exemplified. Among these solvents, one type can be singularly used, and multiple types can be used by mixing at an arbitrary ratio, as well. In terms of producing good yield of the europium complex, as the solvents, dichloromethane, chloroform, methanol and ethanol are preferable.

As usages of europium salt and the phosphine oxide (9) at the time of implementing the manufacturing method in Method 3, it is preferable to use 0.5 to 5.0 moles of the phosphine oxide (9), and it is further preferable to use 1.0 to 2.5 moles, with respect to 1 mole of europium salt.

Further, as usages of europium salt and the β-diketone (8) at the time of implementing the manufacturing method in Method 3, it is preferable to use 1.0 to 10 moles of the β-diketone (8), and it is further preferable to use 2.0 to 8.0 moles, with respect to 1 mole of europium salt.

In the manufacturing method in Method 3, the reaction temperature and the reaction time are not particularly limited, and normal conditions at the time of manufacturing metal complexes can be used. As a specific example, the europium complex C can be manufactured with a good yield at a reaction temperature that is appropriately selected from a range of temperature from −80° C. to 120° C., by selecting a reaction time that is appropriately selected from a range of time period from 1 minute to 120 hours.

The europium complex C manufactured in Method 3 can be refined by using an appropriately selected normal refining method at the time of refining metal complexes. As a specific refining method, filtration, extraction, centrifugal separation, decantation, distillation, sublimation, crystallization, column chromatography and the like can be exemplified.

(Method 4)

Further, the europium complex C can be manufactured in accordance with Method 4 where a diketonato complex (10) and the phosphine oxide (9) are reacted, as well.

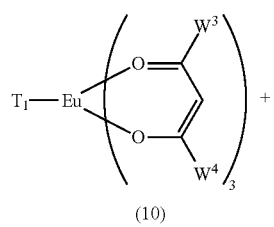

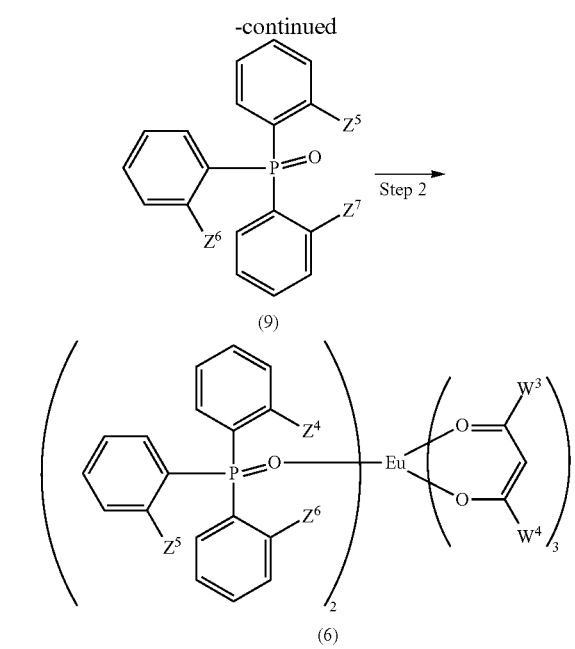

(wherein, $Z^4$, $Z^5$, $Z^6$, $W^3$ and $W^4$ have the same meanings as those of $Z^4$, $Z^5$, $Z^6$, $W^3$ and $W^4$ of the formula (6), respectively. T represents a coordinated molecule. 'l' represents an integer of 0 to 6.)

Method 4 is a method for manufacturing the europium complex C by reacting the phosphine oxide (9) and the diketonato complex (10), and the europium complex C can be obtained with a good yield by applying synthesis conditions described, for example, in Applied Physics Letters, Vol. 83, pp. 3599-3601, 2003.

The coordinated molecule represented by T is not limited as long as it does not interfere with reactions, and specifically, water, heavy water, tetrahydrofuran, pyridine, imidazole, acetone, methanol, ethanol, propanol, isopropyl alcohol, nitriles, such as acetonitrile or propionitrile, amines, such as ammonia, diethylamine or triethylamine, and ethers, such as dimethyl ether, diethyl ether or tetrahydrofuran, can be exemplified, and water is preferable in terms of easy synthesis of the diketonato complex (10).

'l' in the diketonato complex (10) represents an integer of 0 to 3, and it is preferably 2 in terms of availability.

The diketonato complex (10) that is used for Method 4 can be obtained using a method described in Reference Example 16 herein, or another method described in Journal of the American Chemical Society, Vol. 87, pp. 5254-5256, 1965.

As specific examples of the diketonato complex (10) that is used in Method 4, tris (hexafluoroacetylacetonato) europium (III), tris (1,1,1,5,5,6,6,6-octafluoro-2,4-dioxohexane-3-ido) europium (III), tris (1,1,5,5-tetrafluoro-2,4-dioxopentane-3-ido) europium (III), tris (1,1,1,2,2,3,3,7,7,8,8,9,9,9-tetradeca-fluoro-4,6-dioxononane-5-ido) europium (III), tris (1,1,1,2,2,3,3,4,4,5,5,6,6,10,10,11,11,12,12,13,13,14,14,15,15,15-hexacosafluoro-7,9-dioxopentadecane-8-ido) europium (III), tris (trifluoroacetylacetonato) europium (III), tris [4,4,4-trifluoro-1-(2-thienyl)-1,3-dioxobutane-2-ido] europium (III), tris (4,4,4-trifluoro-1-phenyl-1,3-dioxobutane-2-ido) europium (III), tris (1,3-diphenyl-1,3-dioxopropane-2-ido) europium (III) and their hydrates and the like can be exemplified.

The phosphine oxide (9) that is used for Method 4 can be obtained using a method described in Reference Example 18 herein or another method described in Chemical Reviews, Vol. 60, pp. 243-260, 1960, or Organic Letters, Vol. 13, pp. 3478-3481, 2011 or the like.

As the phosphine oxide (9) that is used for Method 4, the similar one that has been exemplified in the description of Method 3 can be exemplified.

A manufacturing method in Method 4 is preferably implemented in a solvent(s) in terms of producing a good yield of the europium complex C. Types of usable solvents are not particularly limited as long as these do not interfere with reactions.

As example of the usable solvents, halogenated hydrocarbons, such as dichloromethane, chloroform or chlorobenzene; alcohols, such as methanol, ethanol, propanol or isopropyl alcohol; esters, such as ethyl acetate, butyl acetate or isoamyl acetate; glycol ethers, such as ethylene glycol monoethyl ether, ethylene glycol monomethyl ether or ethylene glycol monobutyl ether; ethers, such as diethyl ether, tert-butyl methyl ether, glyme, diglyme, triglyme or tetrahydrofuran; ketones, such as tert-butyl methyl ketone, isobutyl methyl ketone, ethyl butyl ketone, dipropyl ketone, diisobutyl ketone, cyclohexanone or acetone; hydrocarbons, such as hexane, cyclohexane, ethylcyclohexane, heptane, octane, benzene, toluene or xylene; and water can be exemplified. Among these solvents, one type can be singularly used, and multiple types can be used by mixing at an arbitrary ratio. As the solvents, dichloromethane, chloroform, methanol and ethanol are preferable in terms of a good yield of the europium complex C.

Next, mole ratios of the diketonato complex (10) and the phosphine oxide (9) at the time of implementing the manufacturing method in Method 4 are explained. It is preferable to use 0.5 to 5.0 moles of the phosphine oxide (9), and it is further preferable to use 1.0 to 2.5 moles, with respect to 1 mole of the diketonato complex (10).

In the manufacturing method in Method 4, the reaction temperature and the reaction time are not particularly limited, and ordinary conditions at the time of manufacturing metal complexes can be used. As a specific example, the europium complex C can be manufactured with a good yield at a reaction temperature that is appropriately selected from a range of temperature from −80° C. to 120° C., by selecting a reaction time that is appropriately selected from a range of time period from 1 minute to 120 hours.

The europium complex C manufactured in Method 4 can be refined by using an appropriately selected normal refining method at the time of refining metal complexes. As a specific refining method, filtration, extraction, centrifugal separation, decantation, distillation, sublimation, crystallization, column chromatography and the like can be exemplified.

(Use Application of Europium Complexes)

Since the europium complexes A, B and C of the present invention have superior light resistance, it is preferable to contain the europium complexes A, B and C in optical materials. As the optical materials, wavelength conversion materials that are less prone to degradation even if irradiating sunlight, an ultraviolet light or the like for a long time, such as films for photovoltaic, agricultural films, LED fluorescent substances or security ink, are preferable and useful.

Further, the europium complexes A, B and C can be used as optical materials containing one type or more to be selected from resin materials, inorganic glass and organic low molecular materials, and optical materials containing resin materials are particularly preferable because of high dispersibility. As the resin materials, for example, polymethacrylate, such as polymethylmethacrylate, polyethylmethacrylate, polypropylmethacrylate, polyisopylmethacrylate, polybutylmethacrylate, poly(sec-butylmethacrylate), polyisobutylmethacrylate, poly(tert-butylmethacrylate), fluorine-containing polymethylmethacrylate, fluorine-containing polyethylmethacrylate, fluorine-containing polypropylmethacrylate, fluorine-containing polyisopylmethacrylate, fluorine-containing polybutylmethacrylate, fluorine-containing poly(sec-butylmethacrylate), fluorine-containing polyisobutylmethacrylate or fluorine-containing poly(tert-butylmethacrylate); polyacrylate, such as polymethyl acrylate, polyethyl acrylate, polypropyl acrylate, polyisopropyl acrylate, polybutyl acrylate, poly(sec-butyl acrylate), polyisobutyl acrylate, poly(tert-butyl acrylate), fluorine-containing polymethyl acrylate, fluorine-containing polyethyl acrylate, fluorine-containing polypropyl acrylate, fluorine-containing polyisopropyl acrylate, fluorine-containing polybutyl acrylate, fluorine-containing poly(sec-butyl acrylate), fluorine-containing polyisobutyl acrylate or fluorine-containing poly(tert-butyl acrylate); polyolefin, such as polystyrene, polyethylene, polypropylene, polybutene, fluorine-containing polyethylene, fluorine-containing polypropylene or fluorine-containing polybutene; polyvinyl ether, fluorine-containing polyvinyl ether, polyvinyl acetate, polyvinyl chloride or their copolymers; cellulose, polyacetal, polyester, polycarbonate, epoxy resin, polyamide resin, polyimide resin, polyurethane, Nafion, petroleum resin, rosin, silicon resin and the like are exemplified.

Among those, polymethylmethacrylate, polyethylmethacrylate, polypropylmethacrylate, polyisopylmethacrylate, polybutylmethacrylate, poly(sec-butylmethacrylate), polyisobutylmethacrylate, poly(tert-butylmethacrylate), polymethyl acrylate, polyethyl acrylate, polypropyl acrylate, polyisopropyl acrylate, polybutyl acrylate, poly(sec-butyl acrylate), polyisobutyl acrylate, poly(tert-butyl acrylate), polyethylene, polystyrene, polyvinyl acetate and their copolymers and the like are preferable. Particularly preferable ones are polymethylmethacrylate, polyethylmethacrylate, polypropylmethacrylate, polybutylmethacrylate, polymethyl acrylate, polyethyl acrylate, polypropyl acrylate, polybutyl acrylate, polyethylene, polystyrene, polyvinyl acetate and their copolymers. These may be used singularly, and two or more can be combined.

Polymethylmethacrylate, polyethylmethacrylate, polypropylmethacrylate, polybutylmethacrylate, polymethyl acrylate, polyethyl acrylate, polypropyl acrylate, polybutyl acrylate, polystyrene, polyvinyl acetate, and their copolymers that are used particularly preferably used among these resins can be obtained, for example, by suspension polymerization of methylmethacrylate, ethylmethacrylate, propylmethacrylate, butylmethacrylate, methyl acrylate, ethyl acrylate, propyl acrylate, butyl acrylate, styrene, vinyl acetate or their comonomers in water at 50 to 80° C. for 3 to 8 hours in the presence of a polymerization initiator.

As the polymerization initiator used above, any initiators that are normally used when these resin materials are polymerized, and for example, azo-based compounds, such as azobisisobutyronitrile, and organic peroxides, such as potassium persulfate, ammonium persulfate or benzoyl peroxide, are exemplified.

On the occasion of the suspension polymerization, it is preferable to add a dispersion stabilizer for the purpose of preventing polymeric particles from clumping together, and any dispersion stabilizers that are normally used are acceptable, and for example, poorly water-soluble inorganic particulates, such as basic calcium phosphate, aluminum hydroxide or magnesium carbonate, and polyacrylate, polymethacrylate, polyacrylamide, polyvinyl alcohol, cellulose derivatives and the like are exemplified.

On the occasion of the suspension polymerization, in order to prevent inhibition of gelled substances, it is preferable to add a modifier. Any modifiers that are normally used are acceptable, and for example, nitroxyl compounds, such as 4-hydroxy-2,2,6,6-tetramethylpiperidine-1-oxyl; nitrites, such as sodium nitrite; nitrogen oxides, such as di-t-butyl nitroxide, and the like are exemplified.

A content ratio of the europium complexes A, B and C in optical materials containing the europium complexes A, B and C and the resin materials is preferably 0.001 to 99% by weight, and is further preferably 0.01 to 10% by weight.

The inorganic glass that is normally used is acceptable, and for example, soda glass, crystal glass, borosilicate glass and the like are exemplified.

The organic low molecular materials that are normally used are acceptable, and for example, ionic liquid, such as amyltriethylammonium bis(trifluoromethanesulphonyl) imide or tetraamylammonium chloride; hydrocarbons, such as pentadecane, hexadecane, octadecane, nonadecane, icosane or paraffin; and the like are exemplified.

As a method for making the optical materials containing the europium complexes A, B and C of the present invention, a method for making the optical material by directly using the europium complexes A, B and C; another method for making the optical material by containing the europium complexes A, B and C into an optical material, which contains one or more types to be selected from the resin materials, the inorganic glass and the organic low molecular materials mentioned above; another method for making the optical materials by mixing a corresponding monomer on the occasion of polymerization of the resin materials into the europium complexes A, B and C to polymerize the monomer; another method for making the optical material by dissolving and dispersing the europium complexes A, B and C in a solvent; and the like are exemplified.

Herein, as a solvent to be used on the occasion of dissolving and dispersing the europium complexes A, B and C into the solvent, for example, halogenated hydrocarbons, such as dichloromethane, chloroform or chlorobenzene; alcohols, such as methanol, ethanol, propanol or isopropyl alcohol; esters, such as ethyl acetate, butyl acetate or isoamyl acetate; glycol ethers, such as ethylene glycol monoethyl ether, ethylene glycol monomethyl ether or ethylene glycol monobutyl ether; ethers, such as diethyl ether, tert-butyl methyl ether, glyme, diglyme, triglyme or tetrahydrofuran; ketones, such as tert-butyl methyl ketone, isobutyl methyl ketone, ethyl butyl ketone, dipropyl ketone, diisobutyl ketone, cyclohexanone or acetone; hydrocarbons, such as hexane, cyclohexane, ethylcyclohexane, heptane, octane, benzene, toluene or xylene; and water are exemplified. Among these solvents, one type can be used singularly, and multiple types can be used by mixing at an arbitrary ratio.

EXAMPLE

Hereafter, the present invention will be explained in further detail according to examples, comparative examples and evaluation examples, but the present invention should not be interpreted as being limited to these. Furthermore, in chemical formulae, a cyclohexyl group is abbreviated as 'Cy'.

For identification of the europium complexes, the following analysis method was used:

For measurement of $^1$H-NMR, $^{19}$F-NMR and $^{31}$P-NMR, ULTRASHIELD PLUS AVANCE III (400 MHz, 376 MHz and 162 MHz) and ASCEND AVANCE III HD (400 MHz, 376 MHz and 162 MHz) manufactured by Bruker Corporation were used.

For $^1$H-NMR, deuterated chloroform (CDCl$_3$) was used as a measurement solvent and tetramethylsilane (TMS) was used as an internal standard material to conduct measurement.

For $^{19}$F-NMR, deuterated chloroform (CDCl$_3$) and deuterated acetone (Acetone-d$_6$) were used as measurement solvents to conduct measurement.

For $^{31}$P-NMR, deuterated chloroform (CDCl$_3$) was used to conduct measurement.

For measurement of mass analysis, Waters 2695-micromass ZQ4000 manufactured by Waters Corporation was used.

For measurement of emission spectrum, a spectrophotometer (manufactured by JASCO Corporation, FP-6500) was used.

For measurement of luminescent quantum yield, an absolute PL quantum yield measuring apparatus (manufactured by Hamamatsu Photonics K.K, C9920-03) was used.

For single crystal X-ray crystallography, obtained single crystal was mounted onto a Goniometer Head, and measurement was conducted by using R-AXIS RAPID II apparatus manufactured by Rigaku Corporation. Details of the analytical conditions are mentioned below.

<Analytical Conditions>

X-ray source: CuK α (λ=1.54187 Å)

Detector: imaging plate

Further, for reagents, commercially available reagents were used.

Reference Example 1

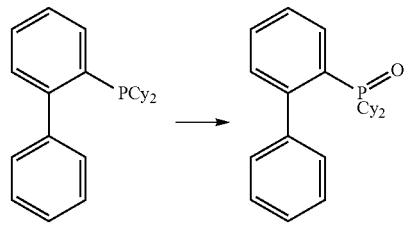

Dissolution of 2-biphenyl (dicyclohexyl) phosphine (1.50 g, 4.28 mmol) into dichloromethane (15 mL) was conducted, and a 30% hydrogen peroxide solution (1.0 mmol) was added and [the mixture] was stirred at room temperature for 1 hour. Water (15 mL) was poured into the reactant mixture, and after organic layers were separated, chloroform (15 mL) was added into an aqueous layer and a chloroform layer was separated. This operation was repeated twice. The organic layers were combined, and after these were dried with magnesium sulfate, they were concentrated under reduced pressure.

By refining the obtained crude product using silica gel column chromatography (eluent: chloroform/methanol), 2-biphenyl (dicyclohexyl) phosphine oxide was obtained as a white solid (1.58 g, yield >99%).

$^1$H-NMR (400 MHz, CDCl$_3$), δ (ppm): 8.11 (m, 1H), 7.53~7.46 (m, 2H), 7.45~7.33 (m, 3H), 7.25~7.19 (m, 3H), 1.88~1.78 (m, 2H), 1.78~1.45 (m, 8H), 1.45~0.96 (m, 12H). $^{31}$P-NMR (162 MHz, CDCl$_3$), δ (ppm): 48.3 (s).

Reference Example 2

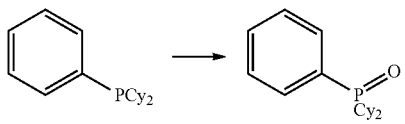

Dicyclohexylphenylphosphine (580 mg, 2.11 mmol) was dissolved into dichloromethane (8.0 mL), and a 30% hydrogen peroxide solution (0.80 mL) was added and [the mixture] was stirred at room temperature for three (3) hours. Water (8 mL) was poured into the reactant mixture, and after organic layers were separated, chloroform (8 mL) was added to an aqueous layer and a chloroform layer was separated. This operation was repeated twice. The organic layers were combined, and after these were dried with magnesium sulfate, they were concentrated under reduced pressure.

Dicyclohexylphenylphosphine oxide (440 mg, yield: 72%) was obtained as a white solid by refining the obtained crude product using silica gel column chromatography (eluent: chloroform/methanol).

$^1$H-NMR (400 MHz, CDCl$_3$), δ (ppm): 7.66 (brt, J=8.0 Hz, 2H), 7.55~7.44 (m, 3H), 2.12~1.97 (m, 4H), 1.88~1.55 (m, 8H), 1.38~1.08 (m, 10H). $^{31}$P-NMR (162 MHz, CDCl$_3$), δ (ppm): 45.3 (s).

Reference Example 3

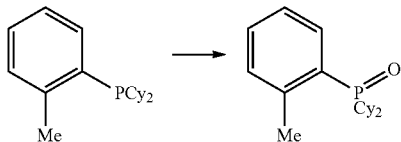

Dicyclohexyl (2-methylphenyl) phosphine (577 mg, 2.0 mmol) was dissolved into dichloromethane (4.0 mL), and after [the obtainment] was cooled down to 0° C., a 30% hydrogen peroxide solution (1.0 mL) was added, and [the mixture] was stirred at room temperature for 1 hour. Water (10 mL) was poured into the reactant mixture, and after organic layers were separated, chloroform (10 mL) was added and a chloroform layer was separated. This operation was repeated twice. The organic layers were combined, and after these were dried with sodium sulfate, they were concentrated under reduced pressure. A white solid of dicyclohexyl (2-methylphenyl) phosphine oxide was obtained by refining the obtained crude product by silica gel column chromatography (eluent: chloroform/methanol) (yield amount: 486 mg, yield: 80%).

$^1$H-NMR (400 MHz, CDCl$_3$), δ (ppm): 7.48~7.42 (m, 1H), 7.37 (t, J=7.6 Hz, 1H), 7.25~7.21 (m, 2H), 2.66 (s, 3H), 2.13~2.00 (m, 4H), 1.89~1.54 (m, 8H), 1.48~1.09 (m, 10H). $^{31}$P-NMR (162 MHz, CDCl$_3$), δ (ppm): 49.3 (s).

Reference Example 4

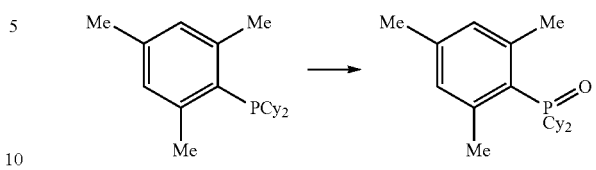

Dicyclohexyl (2,4,6-trimethylphenyl) phosphine (475 mg, 1.5 mmol) was dissolved into dichloromethane (3.0 mL), and after [the obtainment] was cooled down to 0° C., a 30% hydrogen peroxide solution (1.0 mL) was added, and [the mixture] was stirred at room temperature for 1 hour. Water (10 mL) was poured into the reactant mixture, and after organic layers were separated, chloroform (10 mL) was added to an aqueous layer, and a chloroform layer was separated. This operation was repeated twice. The organic layers were combined, and after these were dried with sodium sulfate and they were concentrated under reduced pressure. A white solid of dicyclohexyl (2,4,6-trimethylphenyl) phosphine oxide was obtained by refining the obtained crude product by silica gel column chromatography (eluent: chloroform/methanol) (yield amount: 605 mg, yield >99%).

$^1$H-NMR (400 MHz, CDCl$_3$), δ (ppm): 6.85 (s, 2H), 2.55 (s, 6H), 2.27 (s, 3H), 2.08~1.99 (m, 4H), 1.89~1.62 (m, 8H), 1.49~1.11 (m, 10H). $^{31}$P-NMR (162 MHz, CDCl$_3$), δ (ppm): 52.8 (s).

Reference Example 5

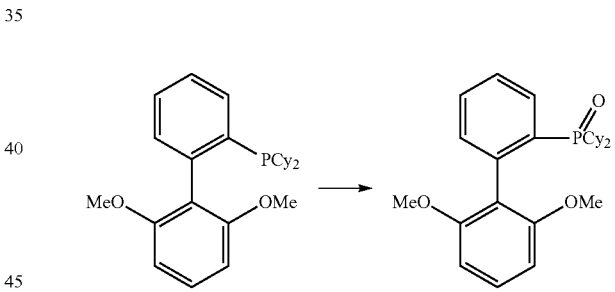

Dissolution of 2-(dicyclohexylphosphino)-2',6'-dimethoxybiphenyl (412 mg, 1.0 mmol) into dichloromethane (5.0 mL) was conducted, and a 30% hydrogen peroxide solution (2.4 mL) was added and [the mixture] was stirred at room temperature for 17 hours. Water (15 mL) was poured into the reactant mixture, and after organic layers were separated, chloroform (15 mL) was added to an aqueous layer, and a chloroform layer was separated. This operation was repeated twice. The organic layers were combined, and after these were dried with sodium sulfate and they were concentrated under reduced pressure. A white solid of dicyclohexyl (2',6'-dimethoxybiphenyl-2-yl) phosphine oxide was obtained by refining the obtained crude products by silica gel column chromatography (eluent: chloroform/methanol) (yield amount: 386 mg, yield: 90%).

$^1$H-NMR (400 MHz, CDCl$_3$), δ (ppm): 7.54~7.46 (m, 1H), 7.34~7.28 (t, J=8.2 Hz, 1H), 7.16~7.12 (m, 1H), 6.60 (d, J=8.5 Hz, 6H), 3.68 (s, 6H), 1.79~1.39 (m, 12H), 1.38~1.24 (m, 2H), 1.20~1.01 (m, 6H). $^{31}$P-NMR (162 MHz, CDCl$_3$), δ (ppm): 46.6 (s).

Reference Example 6

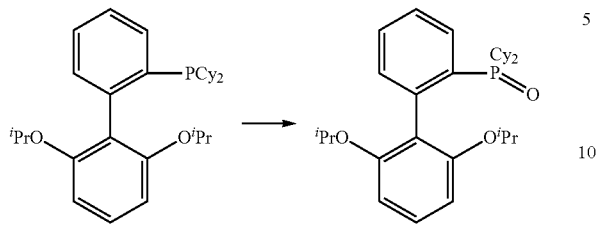

Dicyclohexyl (2',6'-diisopropoxy biphenyl-2-yl) phosphine (500 mg, 1.1 mmol) was dissolved into dichloromethane (4.0 mL), and after [the obtainment] was cooled down to 0° C., a 30% hydrogen peroxide solution (1.0 mL) was added, and [the mixture] was stirred at room temperature for 1 hour. Water (10 mL) was poured into the reactant mixture, and after organic layers were separated, chloroform (10 mL) was added into an aqueous layer, and a chloroform layer was separated. This operation was repeated twice. The organic layers were combined, and after these were dried with sodium sulfate and they were concentrated under reduced pressure. A colorless oily matter of dicyclohexyl (2',6'-diisopropoxy biphenyl-2-yl) phosphine oxide was obtained by refining the obtained crude product by silica gel column chromatography (eluent: chloroform/methanol) (yield amount: 572 mg, yield >99%).

$^1$H-NMR (400 MHz, CDCl$_3$), δ (ppm): 7.92~7.86 (m, 1H), 7.44~7.34 (m, 2H), 7.21 (t, J=8.4 Hz, 1H), 7.05~7.00 (m, 1H), 6.59 (d, J=8.4 Hz, 2H), 4.38 (sept, J=6.0 Hz, 2H), 1.80~1.00 (m, 34H). $^{31}$P-NMR (162 MHz, CDCl$_3$), δ (ppm): 46.7 (s).

Reference Example 7

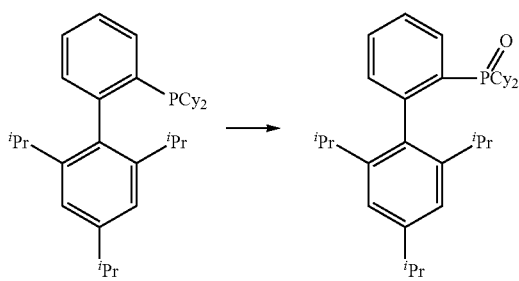

Dissolution of 2-dicyclohexylphosphino-2',4',6'-triisopropylbiphenyl (716 mg, 1.5 mmol) into dichloromethane (5.0 mL) was conducted, and a 30% hydrogen peroxide solution (3.6 mL) was added and [the mixture] was stirred at room temperature for 17 hours. Water (15 mL) was poured into the reactant mixture, and after organic layers were separated, chloroform (15 mL) was added into an aqueous layer, and a chloroform layer was separated. This operation was repeated twice. The organic layers were combined, and after these were dried with sodium sulfate and they were concentrated under reduced pressure. A white solid of dicyclohexyl (2',4',6'-triisopropylbiphenyl-2-yl) phosphine oxide was obtained by refining the obtained crude product using silica gel column chromatography (eluent: chloroform/methanol) (yield amount: 588 mg, yield: 80%).

$^1$H-NMR (400 MHz, CDCl$_3$), δ (ppm): 7.72~7.63 (m, 1H), 7.48~7.36 (m, 2H), 7.20~7.14 (m, 1H), 7.01-6.95 (m, 2H), 2.97~2.80 (m, 1H), 2.45~2.30 (m, 2H), 1.93~1.79 (m, 4H), 1.78~1.67 (m, 8H), 1.44-1.33 (m, 4H), 1.32~1.22 (m, 12H), 1.21~1.08 (m, 6H), 0.96 (d, J=6.7 Hz, 6H). $^{31}$P-NMR (162 MHz, CDCl$_3$), δ (ppm): 44.4 (s).

Reference Example 8

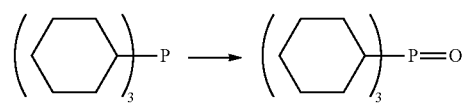

Tricyclohexyl phosphine (1.66 g, 5.9 mmol) was dissolved into dichloromethane (10 mL), and a 30% hydrogen peroxide solution (3.0 mL) was added, and [the mixture] was stirred at room temperature for one (1) hour. Water (15 mL) was poured into the reactant mixture, and after organic layers were separated, chloroform (15 mL) was added to an aqueous layer, and a chloroform layer was separated. This operation was repeated twice. The organic layers were combined, and after these were dried with sodium sulfate and they were concentrated under reduced pressure. A white solid of tricyclohexyl phosphine oxide was obtained by refining the obtained crude product by silica gel column chromatography (eluent: chloroform/methanol) (yield amount: 1.24 g, yield: 71%).

$^1$H-NMR (400 MHz, CDCl$_3$), δ (ppm): 1.94~1.73 (m, 18H), 1.48~1.25 (m, 15H). $^{31}$P-NMR (162 MHz, CDCl$_3$), δ (ppm): 50.0 (s).

Reference Example 9

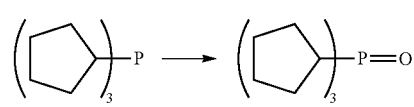

Tricyclopentylphosphine (1.00 g, 4.20 mmol) was poured, and was dissolved into dichloromethane (26 mL). After this solution was cooled down to 0° C., a 30% hydrogen peroxide solution (1.3 mL) was poured, and [the mixture] was stirred at 0° C. for 15 minutes and then at room temperature for 2 hours. Water (13 mL) was poured into the reactant mixture, and after organic layers were separated, chloroform (26 mL) was added to an aqueous layer, and a chloroform layer was separated. This operation was repeated twice. The organic layers were combined, and after these were dried with sodium sulfate and they were concentrated under reduced pressure. A white solid of tri (cyclopentyl) phosphine oxide was obtained by refining the obtained crude product by silica gel column chromatography (eluent: chloroform/methanol) (yield amount: 653 mg, yield: 61%).

$^1$H-NMR (400 MHz, CDCl$_3$), δ (ppm): 2.16~2.02 (m, 3H), 1.95~1.51 (m, 24H). $^{31}$P-NMR (162 MHz, CDCl$_3$), δ (ppm): 54.0 (s, 1P).

Reference Example 10

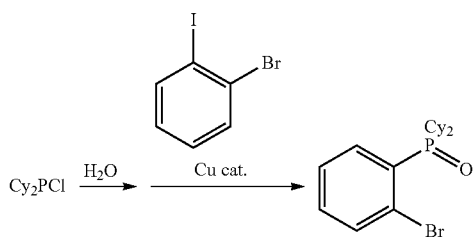

Under argon atmosphere, chlorodicyclohexylphosphine (2.2 mL, 10 mmol) was dissolved into tetrahydrofuran (50 mL), and water (5.0 mL) was added and [the mixture] was stirred at room temperature for 2 hours. After a solvent(s) was removed by concentration, chloroform (20 mL) was poured into the reactant mixture, and a chloroform layer was separated. This operation was repeated twice. After organic layers were dried with sodium sulfate, these were concentrated under reduced pressure, and a white solid of dicyclohexylphosphine oxide (yield amount: 2.04 g, yield: 95%).

$^1$H-NMR (400 MHz, CDCl$_3$), δ (ppm): 6.31 (d, $J_{PH}$=433.5 Hz, 1H), 2.01~1.65 (m, 12H), 1.57~1.19 (m, 10H). $^{31}$P-NMR (162 MHz, CDCl$_3$), δ (ppm): 49.4 (s).

Under argon atmosphere, toluene (25 mL) was added to the above-mentioned dicyclohexylphosphine oxide (1.5 g, 7.0 mmol), 1-bromo-2-iodobenzene (0.88 mL, 7.0 mmol), copper (I) iodide (267 mg, 1.4 mmol) and 2,2'-bipyridyl (219 mg, 1.4 mmol), and [the mixture] was stirred at room temperature for five (5) minutes. Cesium carbonate (4.56 g, 14 mmol) was added into the reactant mixture, and [the mixture] was stirred at 100° C. for twenty one (21) hours. After any insoluble matter was removed by filtration, chloroform (30 mL) was poured into the reactant mixture, and [the mixture] was washed with 1M hydrochloride (30 mL) three times. After a separated organic layer(s) was dried with sodium sulfate, these were concentrated under reduced pressure. A white solid of (2-bromophenyl) dicyclohexylphosphine oxide was obtained by refining the obtained crude product by silica gel column chromatography (eluent: chloroform/methanol) (yield amount: 6.07 g, yield: 70%).

$^1$H-NMR (400 MHz, CDCl$_3$), δ (ppm): 8.13 (ddd, J=10.6, 7.6, 1.8 Hz, 1H), 7.59 (dd, J=7.6, 3.4 Hz, 1H), 7.46 (t, J=7.6 Hz, 1H), 7.34 (t, J=7.6 Hz, 1H), 2.51~2.40 (m, 2H), 2.16~2.05 (m, 2H), 1.92~1.81 (m, 2H), 1.78~1.59 (m, 6H), 1.44~1.14 (m, 10H). $^{31}$P-NMR (162 MHz, CDCl$_3$), δ (ppm): 48.7 (s).

Reference Example 11

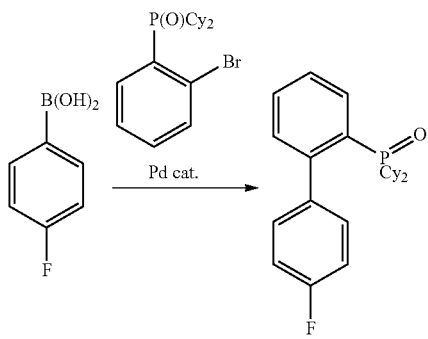

Under argon atmosphere, toluene (4.0 mL) was added to (2-bromophenyl) dicyclohexylphosphine oxide (369 mg, 1.0 mmol) obtained in Reference Example 10, 4-fluorophenylboronic acid (280 mg, 2.0 mmol), dicyclohexyl (2',6'-diisopropoxy biphenyl-2-yl) phosphine (37 mg, 0.08 mmol), tripotassium phosphate (637 mg, 3.0 mmol) and tris (dibenzylideneacetone) dipalladium (0) (18 mg, 0.020 mmol), and [the mixture] was stirred at 100° C. for 19 hours. Water (10 mL) was poured into the reactant mixture. Chloroform (10 mL) was added into an aqueous layer, and a chloroform layer was separated. This operation was repeated three times. The organic layers were combined, and after these were dried with sodium sulfate and they were concentrated under reduced pressure.

A white solid of (4'-fluoro-[1,1'-biphenyl]-2-yl) dicyclohexylphosphine oxide was obtained by refining the obtained crude product by silica gel column chromatography (eluent: chloroform/methanol) (yield amount: 339 mg, yield: 88%).

$^1$H-NMR (400 MHz, CDCl$_3$), δ (ppm): 7.99 (m, 1H), 7.52~7.46 (m, 2H), 7.24~7.17 (m, 3H), 7.13~7.07 (m, 2H), 1.90~1.01 (m, 22H). $^{19}$F-NMR (376 MHz, CDCl$_3$), δ (ppm): −114.3 (s). $^{31}$P-NMR (162 MHz, CDCl$_3$), δ (ppm): 47.8 (s).

Reference Example 12

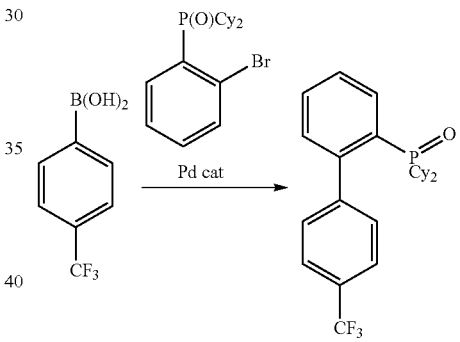

Under argon atmosphere, 1,4-dioxane (3.4 mL) was added to (2-bromophenyl) dicyclohexylphosphine oxide (369 mg, 1.0 mmol) obtained in Reference Example 10, 4-(trifluoromethyl) phenylboronic acid (379 mg, 2.0 mmol), triphenylphosphine (31 mg, 0.12 mmol), tripotassium phosphate (637 mg, 3.0 mmol) and bis (dibenzylideneacetone) palladium (0) (17 mg, 0.030 mmol), [the mixture] was stirred at 100° C. for 14 hours. Water (20 mL) was poured into the reactant mixture. Chloroform (20 mL) was added to an aqueous layer, and a chloroform layer was separated. This operation was repeated twice. The organic layers were combined, and after these were dried with sodium sulfate and they were concentrated under reduced pressure. A white solid of (4'-trifluoromethyl-[1,1'-biphenyl]-2-yl) dicyclohexylphosphine oxide was obtained by refining the obtained crude product by silica gel column chromatography (eluent: hexane/ethyl acetate) (yield amount: 204 mg, yield: 47%).

$^1$H-NMR (400 MHz, CDCl$_3$), δ (ppm): 7.84 (m, 1H), 7.65 (d, J=8.0 Hz, 2H), 7.53~7.50 (m, 2H), 7.38 (d, J=8.0 Hz, 2H), 7.21 (m, 1H), 1.87~1.05 (m, 22H). $^{19}$F-NMR (376 MHz, CDCl$_3$), δ (ppm): −62.4 (s). $^{31}$P-NMR (162 MHz, CDCl$_3$), δ (ppm): 47.3 (s).

Reference Example 13

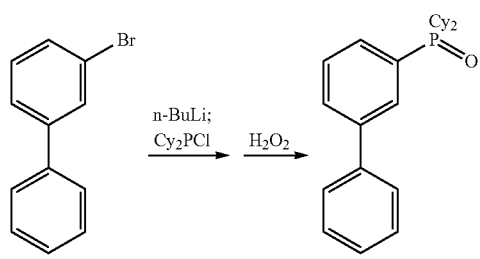

Under argon atmosphere, 3-bromobiphenyl (513 mg, 2.2 mmol) was dissolved into diethyl ether (5.0 mL), and [the obtainment] was cooled down to −20° C. Into this solution, n-butyllithium in 2.67M hexane solution (0.85 mL, 2.3 mmol) was delivered by drops, and after stirring for 2 hours, chlorodicyclohexylphosphine (0.44 mL, 2.0 mmol) was added and [the mixture] was heated to room temperature and stirred for 6 hours. The reactant mixture was concentrated under reduced pressure, and a white solid of 3-biphenyl (dicyclohexyl) phosphine was obtained by refining the obtained crude product by silica gel column chromatography (eluent: hexane/ethyl acetate) (yield amount: 645 mg, yield: 92%).

$^1$H-NMR (400 MHz, CDCl$_3$), δ (ppm): 7.68 (d, J=7.6 Hz, 1H), 7.63~7.54 (m, 3H), 7.49~7.33 (m, 5H), 2.00~0.98 (m, 22H). $^{31}$P-NMR (162 MHz, CDCl$_3$), δ (ppm): 3.68 (s).

The above-mentioned 3-biphenyl (dicyclohexyl) phosphine (631 mg, 1.8 mmol) was dissolved into dichloromethane (4.0 mL), and after [the obtainment] was cooled down to 0° C., a 30% hydrogen peroxide solution (1.0 mL) was added and [the mixture] was stirred at room temperature for 1 hour. Water (10 mL) was poured into the reactant mixture, and after organic layers were separated, chloroform (10 mL) was added into an aqueous layer, and a chloroform layer was separated. This operation was repeated twice. The organic layers were combined, and after these were dried with sodium sulfate and they were concentrated under reduced pressure. A white solid of 3-biphenyl (dicyclohexyl) phosphine oxide was obtained by refining the obtained crude product by silica gel column chromatography (eluent: chloroform/methanol) (yield amount: 969 mg, yield: >99%).

$^1$H-NMR (400 MHz, CDCl$_3$), δ (ppm): 7.89 (d, J=10 Hz, 1H), 7.74 (d, J=7.5 Hz, 1H), 7.65~7.58 (m, 3H), 7.54 (td, J=7.5, 2.8 Hz, 1H), 7.47 (t, J=7.5 Hz, 2H), 7.39 (t, J=7.5 Hz, 1H), 2.13~2.01 (m, 4H), 1.88~1.61 (m, 8H), 1.40~1.09 (m, 10H). $^{31}$P-NMR (162 MHz, CDCl$_3$) δ (ppm): 45.0 (s).

Reference Example 14

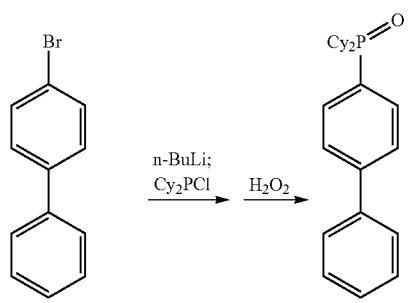

Under argon atmosphere, 4-bromobiphenyl (513 mg, 2.2 mmol) was dissolved into diethyl ether (5.0 mL), and [the obtainment] was cooled down to −20° C. Into this solution, n-butyllithium in a 2.67M hexane solution (0.85 mL, 2.3 mmol) was delivered by drops, and after stirring for 2 hours, chlorodicyclohexylphosphine (0.44 mL, 2.0 mmol) was added, and [the mixture] was heated to room temperature and stirred for 6 hours. The reactant mixture was concentrated under reduced pressure and a white solid of 4-biphenyl (dicyclohexyl) phosphine was obtained by refining the obtained crude product by silica gel column chromatography (eluent: hexane/ethyl acetate) (yield amount: 592 mg, yield: 85%).

$^1$H-NMR (400 MHz, CDCl$_3$), δ (ppm): 7.72 (m, 1H), 7.65~7.59 (m, 2H), 7.59~7.49 (m, 3H), 7.48~7.32 (m, 3H), 2.12~1.54 (m, 12H), 1.41~0.96 (m, 10H). $^{31}$P-NMR (162 MHz, CDCl$_3$), δ (ppm): 2.19 (s).

Dissolution of 4-biphenyl (dicyclohexyl) phosphine (592 mg, 1.7 mmol) into dichloromethane (4.0 mL) was conducted, and after cooling down to 0° C., 30% hydrogen peroxide solution (1.0 mL) was added, and [the mixture] was stirred at room temperature for 1 hour. Water (10 mL) was poured into the reactant mixture, and after organic layers were separated, chloroform (10 mL) was added into an aqueous layer, and a chloroform layer was separated. This operation was repeated twice. The organic layers were combined, and after these were dried with sodium sulfate and they were concentrated under reduced pressure. A white solid of 4-biphenyl (dicyclohexyl) phosphine oxide was obtained by refining the obtained crude product by silica gel column chromatography (eluent: chloroform/methanol) (yield amount: 612 mg, yield >99%).

$^1$H-NMR (400 MHz, CDCl$_3$), δ (ppm): 7.76~7.67 (m, 4H), 7.65~7.61 (m, 2H), 7.50~7.44 (m, 2H), 7.39 (m, 1H), 2.14~1.99 (m, 4H), 1.90~1.61 (m, 8H), 1.41~1.09 (m, 10H). $^{31}$P-NMR (162 MHz, CDCl$_3$), δ (ppm): 45.0 (s).

Reference Example 15

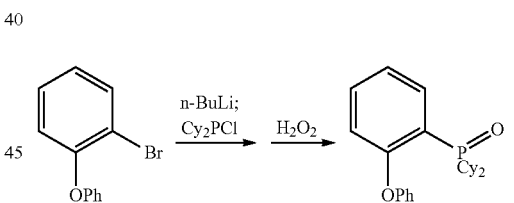

Under argon atmosphere, 2-bromodiphenyl ether (498 mg, 2.0 mmol) was dissolved into tetrahydrofuran (16.0 mL), and [the obtainment] was cooled down to −80° C. Into this solution, n-butyllithium in 2.67M hexane solution (0.77 mL, 2.1 mmol) was delivered by drops, and after stirring for 3 hours, chlorodicyclohexylphosphine (0.44 mL, 2.0 mmol) was added, and [the mixture temperature] was heated to room temperature and was stirred for 18 hours. Water (20 mL) was poured into the reactant mixture. Dichloromethane (20 mL) was added to an aqueous layer, and a dichloromethane layer was separated. This operation was repeated twice. The organic layers were combined, and after these were dried with sodium sulfate and they were concentrated under reduced pressure. A white solid of dicyclohexyl (2-phenoxyphenyl) phosphine was obtained by refining the obtained crude product by silica gel column chromatography (eluent: hexane/ethyl acetate) (yield amount: 678 mg, yield: 93%).

$^1$H-NMR (400 MHz, CDCl$_3$), δ (ppm): 7.50 (m, 1H), 7.36~7.24 (m, 3H), 7.11~7.05 (m, 2H), 6.99~6.93 (m, 2H), 6.82 (m, 1H), 2.11~2.00 (m, 2H), 1.92~1.57 (m, 10H), 1.33~1.01 (m, 10H). $^{31}$P-NMR (162 MHz, CDCl$_3$), δ (ppm): −6.60 (s).

Dicyclohexyl (2-phenoxyphenyl) phosphine (678 mg, 1.9 mmol) was dissolved into dichloromethane (4.0 mL), and after [the obtainment] was cooled down to 0° C., a 30% hydrogen peroxide solution (1.0 mL) was added, and [the mixture] was stirred at room temperature for 1 hour. Water (10 mL) was poured into the reactant mixture, and after organic layers were separated, chloroform (10 mL) was added into an aqueous layer, and a chloroform layer was separated. This operation was repeated twice. The organic layers were combined, and after these were dried with sodium sulfate and they were concentrated under reduced pressure. A white solid of dicyclohexyl (2-phenoxyphenyl) phosphine oxide was obtained by refining the obtained crude product by silica gel column chromatography (eluent: chloroform/methanol) (yield amount: 533 mg, yield: 75%).

$^1$H-NMR (400 MHz, CDCl$_3$), δ (ppm): 8.04 (m, 1H), 7.44~7.35 (m, 3H), 7.24~7.17 (m, 2H), 7.05~7.00 (m, 2H), 6.74 (m, 1H), 2.26~2.02 (m, 4H), 1.87~1.57 (m, 8H), 1.55~1.37 (m, 4H), 1.31~1.05 (m, 6H). $^{31}$P-NMR (162 MHz, CDCl$_3$), δ (ppm): 47.9 (s).

Reference Example 16

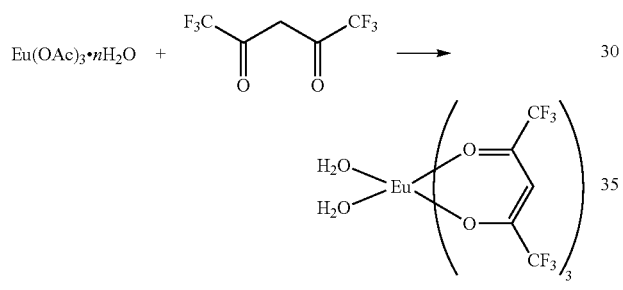

Under argon atmosphere, purified water (100 mL) was added to europium (III) acetate hydrate (8.0 g, 21 mmol as 2.5 hydrate), and [the mixture] was stirred at room temperature for 10 minutes. After Hhfa (16.7 g, 80.2 mmol) was delivered by drops into the reactant mixture, [the mixture] was stirred at 50° C. for 3 hours. The obtained white suspension was filtrated, and the obtained white solid was washed with water (200 mL) and toluene (200 mL), and then, diaqua-tris (hexafluoroacetylacetonato) europium (III) was obtained as a white solid (yield amount: 11.6 g, yield: 68% as using 21 mmol of europium acetate 2.5 hydrate).

$^{19}$F-NMR (376 MHz, Acetone-d$_6$), δ (ppm): −81.2 (brs). ESIMS (m/z): 566.8 [M-hfa]$^+$.

Example 1

Under argon atmosphere, dichloromethane (8.0 mL) was added to europium (III) acetate hydrate (170 mg, 0.46 mmol, as 2.5 hydrate) and (2-biphenyl) dicyclohexylphosphine oxide (338 mg, 0.92 mmol) obtained in Reference Example 1, and [the mixture] was stirred at room temperature for 30 minutes. After Hhfa in a 0.3M dichloromethane solution (4.7 mL, 1.4 mmol) was delivered by drops into the reactant mixture, [the mixture] was stirred at room temperature for 3 hours. Hexane was poured into the reaction liquid and [the mixture] was left at room temperature, and a reddish white solid of bis [(2-biphenyl) dicyclohexylphosphine oxide)] tris (hexafluoroacetylacetonato) europium (III) was obtained by filtrating the precipitated solid (yield amount: 483 mg, yield: 35%)

$^{19}$F-NMR (376 MHz, CDCl$_3$), δ (ppm): −78.4 (brs). $^{31}$P-NMR (162 MHz, CDCl$_3$), δ (ppm): −81.1 (brs). ESIMS (m/z): 1297.6 [M-hfa]$^+$.

Example 2

Under argon atmosphere, dichloromethane (5.0 mL) was added to europium (III) acetate hydrate (132 mg, 0.40 mmol, as 2.5 hydrate) and dicyclohexylphenylphosphine oxide (232 mg, 0.80 mmol) obtained in Reference Example 2, and [the mixture] was stirred at room temperature for 1 hour. After Hhfa in a 1.8M dichloromethane solution (0.67 mL, 1.2 mmol) was delivered by drops into the reactant mixture, [the mixture] was stirred at room temperature for 3 hours. After any insoluble matter was removed by filtration, the reaction liquid was concentrated under reduced pressure and recrystallized with methanol, and then, a reddish white solid of bis (dicyclohexylphenylphosphine oxide) tris (hexafluoroacetylacetonato) europium (III) was obtained (yield amount: 381 mg, yield: 70%).

$^{19}$F-NMR (376 MHz, CDCl$_3$), δ (ppm): −78.3 (s). $^{31}$P-NMR (162 MHz, CDCl$_3$), δ (ppm): −80.6 (brs). ESIMS (m/z): 1147.7 [M-hfa]+.

Example 3

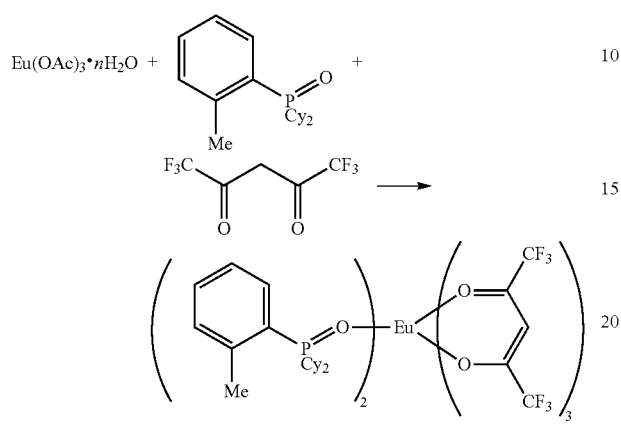

Under argon atmosphere, dichloromethane (3.0 mL) was added to europium (III) acetate hydrate (112 mg, 0.30 mmol, as 2.5 hydrate) and dicyclohexyl (2-methylphenyl) phosphine oxide (183 mg, 0.60 mmol) obtained in Reference Example 3, and [the mixture] was stirred at room temperature for 1 hour. After Hhfa in a 1.8M dichloromethane solution (0.5 mL, 0.90 mmol) was delivered by drops into the reactant mixture, and [the mixture] was stirred at room temperature for 12 hours. The reaction liquid was concentrated under reduced pressure and recrystallized with dichloromethane/acetonitrile, and then, a reddish white solid of bis [dicyclohexyl-(2-methylphenyl) phosphine oxide] tris (hexafluoroacetylacetonato) europium (III) was obtained (yield amount: 321 mg, yield: 77%).

$^{19}$F-NMR (376 MHz, CDCl$_3$), δ (ppm): −78.4 (brs). $^{31}$P-NMR (162 MHz, CDCl$_3$), δ (ppm): −76.3 (brs). ESIMS (m/z): 1175.3 [M-hfa]$^+$.

Example 4

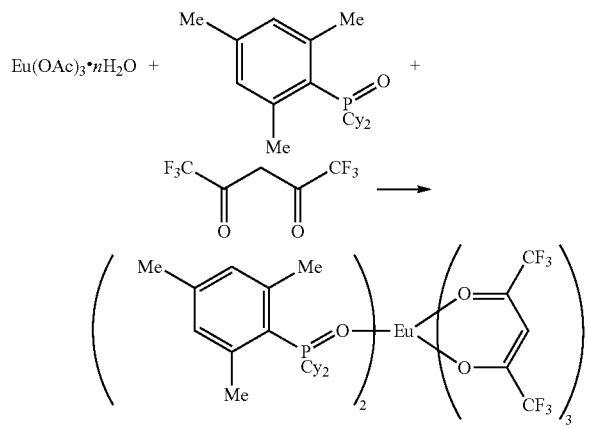

Under argon atmosphere, dichloromethane (3.0 mL) was added to europium (III) acetate hydrate (112 mg, 0.30 mmol, as 2.5 hydrate) and dicyclohexyl (2,4,6-trimethylphenyl) phosphine oxide (199 mg, 0.60 mmol) obtained in Reference Example 4, and [the mixture] was stirred at room temperature for 1 hour. After Hhfa in a 1.8M dichloromethane solution (0.5 mL, 0.90 mmol) was delivered by drops into the reactant mixture, [the mixture] was stirred at room temperature for 12 hours. The reaction liquid was concentrated under reduced pressure and recrystallized with dichloromethane/acetonitrile, and then, a reddish white solid of bis [dicyclohexyl-(2, 4, 6-trimethylphenyl) phosphine oxide] tris (hexafluoroacetylacetonato) europium (III) was obtained (yield amount: 162 mg, yield: 38%).

$^{19}$F-NMR (376 MHz, CDCl$_3$), δ (ppm): −79.1 (brs). $^{31}$P-NMR (162 MHz, CDCl$_3$), δ (ppm): −71.6 (brs). ESIMS (m/z): 1231.3 [M-hfa]$^+$.

Example 5

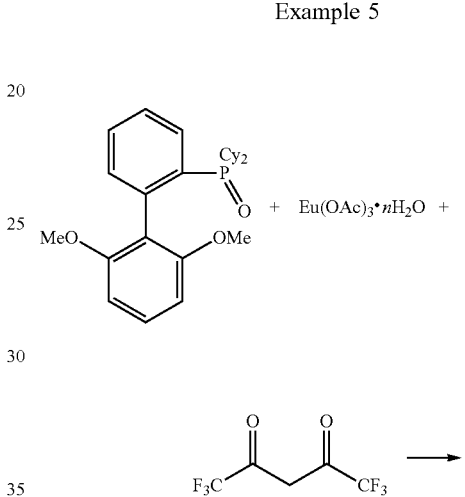

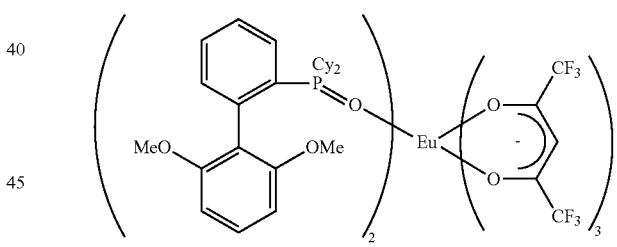

Under argon atmosphere, dichloromethane (5 mL) was added to europium (III) acetate hydrate (100 mg, 0.30 mmol, as 2.5 hydrate) and dicyclohexyl (2', 6'-dimethoxybiphenyl-2-yl) phosphine oxide (257 mg, 0.60 mmol) obtained in Reference Example 5, and [the mixture] was stirred at room temperature for 30 minutes. After Hhfa in a 1.8M dichloromethane solution (0.5 mL, 0.9 mmol) was delivered by drops into the reactant mixture, [the mixture] was stirred at room temperature for 3 hours. After any insoluble matter was removed by filtration, the reaction liquid was concentrated under reduced pressure and [the obtainment] was washed with hexane, and then, a reddish white solid of bis [dicyclohexyl-(2',6'-dimethoxybiphenyl-2-yl) phosphine oxide] tris (hexafluoroacetylacetonato) europium (III) was obtained (yield amount: 332 mg, yield: 67%).

$^{19}$F-NMR (376 MHz, CDCl$_3$), δ (ppm): −78.5 (s). $^{31}$P-NMR (162 MHz, CDCl$_3$), δ (ppm): −84.0 (brs). ESIMS (m/z): 1419.7 [M-hfa]$^+$.

Example 6

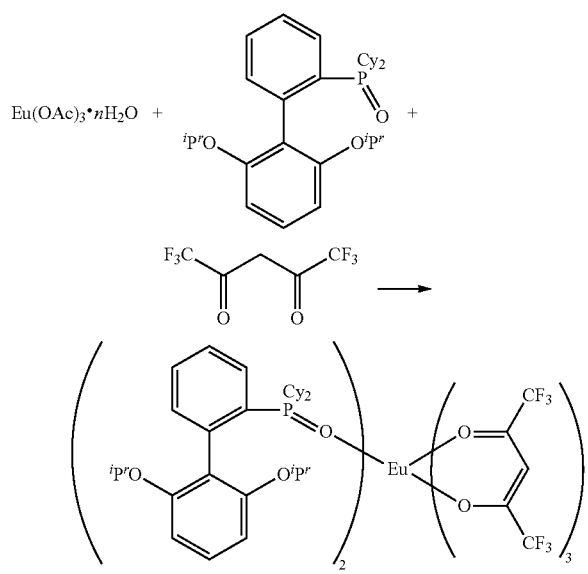

Under argon atmosphere, dichloromethane (2.0 mL) was added to europium (III) acetate hydrate (58 mg, 0.16 mmol, as 2.5 hydrate) and dicyclohexyl (2', 6'-diisopropoxy biphenyl-2-yl) phosphine oxide (153 mg, 0.32 mmol) obtained in Reference Example 6, and [the mixture] was stirred at room temperature for 1 hour. After Hhfa in a 1.0M dichloromethane solution (0.48 mL, 0.48 mmol) was delivered by drops into the reactant mixture, [the mixture] was stirred at room temperature for 8 hours. The reaction liquid was concentrated under reduced pressure and recrystallized with dichloromethane/methanol, and then, a reddish white solid of bis [dicyclohexyl (2', 6'-diisopropoxy biphenyl-2-yl) phosphine oxide] tris (hexafluoroacetylacetonato) europium (III) was obtained (yield amount: 172 mg, yield: 64 mg).

$^{19}$F-NMR (376 MHz, CDCl$_3$), δ (ppm): −78.1 (brs). $^{31}$P-NMR (162 MHz, CDCl$_3$), δ (ppm): −85.4 (brs). ESIMS (m/z): 1531.1 [M-hfa]$^+$.

Example 7

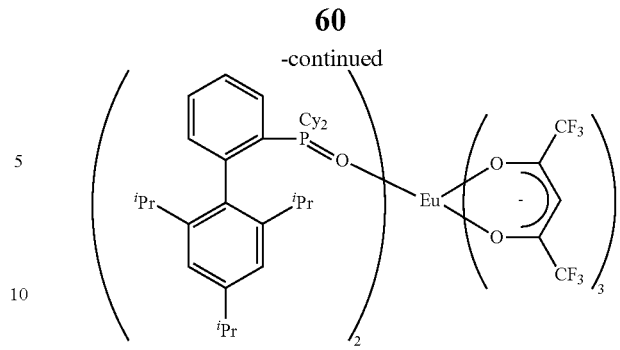

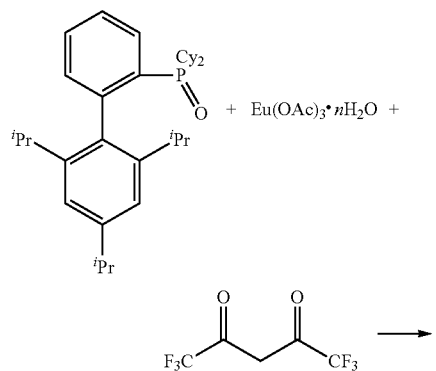

Under argon atmosphere, dichloromethane (5.0 mL) was added to europium (III) acetate hydrate (99 mg, 0.30 mmol, as 2.5 hydrate) and dicyclohexyl (2', 4', 6'-triisopropylbiphenyl-2-yl) phosphine oxide (296 mg, 0.60 mmol) obtained in Reference Example 7, and [the mixture] was stirred at room temperature for 30 minutes. After Hhfa in a dichloromethane solution (1.8M, 0.5 mL, 0.9 mmol) was delivered by drops into the reactant mixture, [the mixture] was stirred at room temperature for 3 hours. After any insoluble matter was removed by filtration, the reaction liquid was concentrated under reduced pressure, and washed with hexane and MeOH, and recrystallized with MeOH, and then, a reddish white solid of bis [dicyclohexyl (2', 4', 6'-triisopropylbiphenyl-2-yl) phosphine oxide] tris (hexafluoroacetylacetonato) europium (III) was obtained (yield amount: 344 mg, yield: 65%).

$^{19}$F-NMR (376 MHz, CDCl$_3$), δ (ppm): −78.5 (s). $^{31}$P-NMR (162 MHz, CDCl$_3$), δ (ppm): −86.0 (brs). ESIMS (m/z): 1552.1 [M-hfa]$^+$.

Example 8

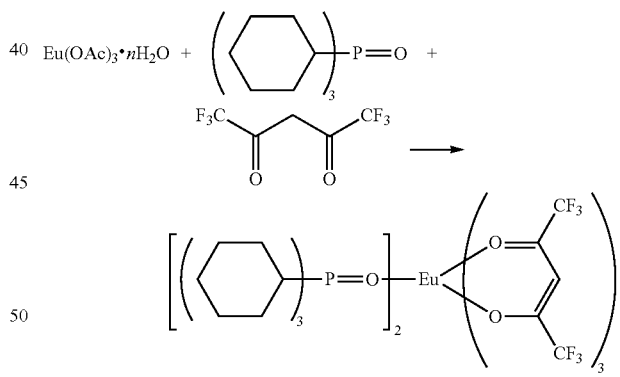

Under argon atmosphere, dichloromethane (3.0 mL) was added to europium (III) acetate hydrate (112 mg, 0.30 mmol, as 2.5 hydrate) and tricyclohexyl phosphine oxide (178 mg, 0.60 mmol) obtained in Reference Example 8, and [the mixture] was stirred at room temperature for 1 hour. After Hhfa in a dichloromethane solution (1.8M, 0.5 mL, 0.9 mmol) was delivered by drops into the reactant mixture, [the obtainment] was stirred at room temperature for 3 hours. The reaction liquid was concentrated under reduced pressure and was recrystallized with dichloromethane/methanol, and then, a white solid of bis (tricyclohexylphosphine oxide)tris (hexafluoroacetylacetonato) europium (III) was obtained (yield amount: 271 mg, yield: 66%).

$^{19}$F-NMR (376 MHz, CDCl$_3$), δ (ppm): −78.0 (brs).
$^{31}$P-NMR (162 MHz, CDCl$_3$), δ (ppm): −71.7 (brs). ESIMS (m/z): 1159.3 [M-hfa]$^+$.

Example 9

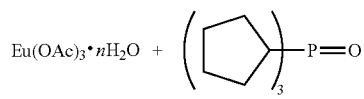

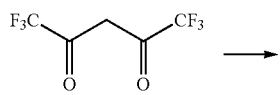

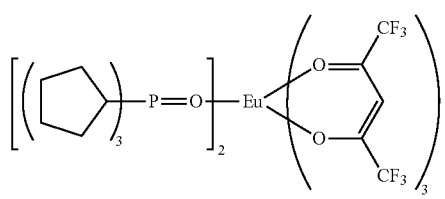

Under argon atmosphere, dichloromethane (3.0 mL) was added to europium (III) acetate hydrate (112 mg, 0.30 mmol, as 2.5 hydrate) and tri (cyclopentyl)phosphine oxide (153 mg, 0.60 mmol) obtained in Reference Example 9, and [the mixture] was stirred at room temperature for 1 hour. After Hhfa in a 1.8M dichloromethane solution (0.50 mL, 0.90 mmol) was delivered by drops into the reactant mixture, [the mixture] was stirred at room temperature for 7 hours. The reaction liquid was concentrated under reduced pressure and was recrystallized with dichloromethane/methanol, and then, a white solid of bis (tri (cyclopentyl) phosphine oxide) tris (hexafluoroacetylacetonato) europium (III) was obtained (yield amount: 223 mg, yield: 58%).

$^{19}$F-NMR (376 MHz, CDCl$_3$), δ (ppm): −77.8 (brs).
$^{31}$P-NMR (162 MHz, CDCl$_3$), δ (ppm): −69.3 (brs). ESIMS (m/z): 1074.9 [M-hfa]$^+$.

Example 10

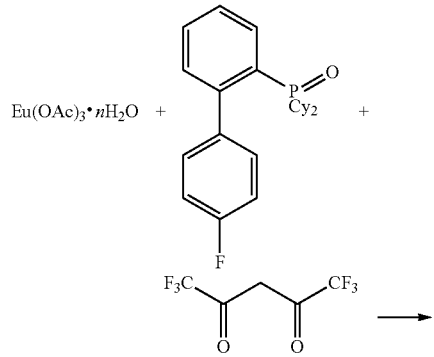

-continued

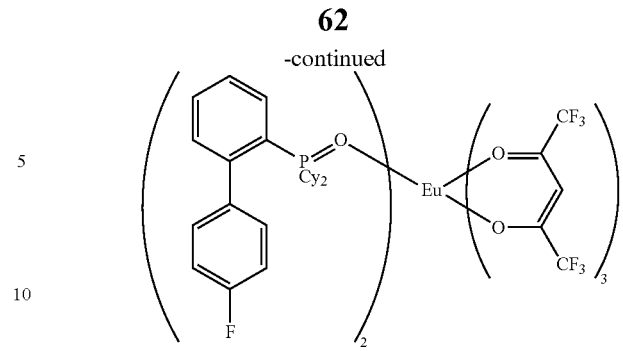

Under argon atmosphere, dichloromethane (2.0 mL) was added to europium (III) acetate hydrate (73 mg, 0.19 mmol, as 2.5 hydrate) and (4'-fluoro-[1,1'-biphenyl]-2-yl) dicyclohexylphosphine oxide (150 mg, 0.38 mmol) obtained in Reference Example 11, and [the mixture] was stirred at room temperature for 1 hour. After Hhfa in a 1.8M dichloromethane solution (0.32 mL, 0.58 mmol) was delivered by drops into the reactant mixture, [the obtainment] was stirred at room temperature for 12 hours. The reaction liquid was concentrated under reduced pressure and was recrystallized with dichloromethane/hexane, and then, a white solid of bis [(4'-fluoro-[1,1'-biphenyl]-2-yl) dicyclohexylphosphine oxide] tris (hexafluoroacetylacetonato) europium (III) was obtained (yield amount: 196 mg, yield: 65%). $^{19}$F-NMR (376 MHz, CDCl$_3$) δ (ppm): −78.4 (brs, 18F), −112.8 (brs, 2F). $^{31}$P-NMR (162 MHz, CDCl$_3$) δ (ppm): −80.5 (brs). ESIMS (m/z): 1335.2 [M-hfa]$^+$.

Example 11

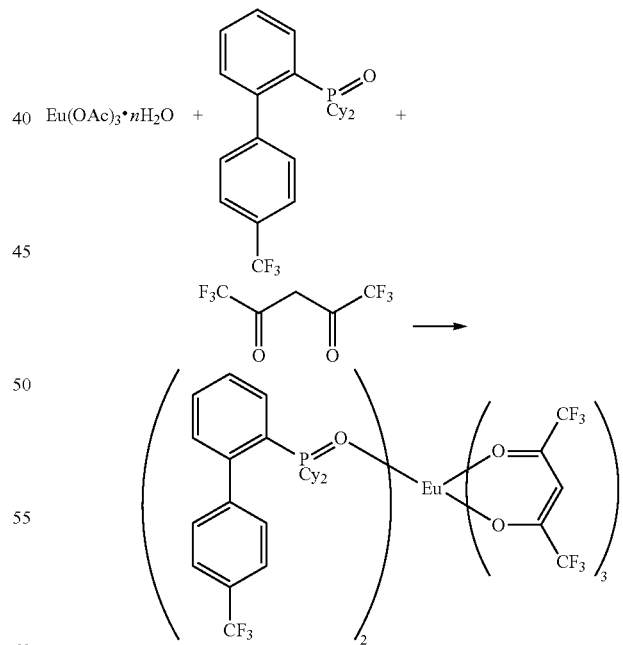

Under argon atmosphere, dichloromethane (2.0 mL) was added to europium (III) acetate hydrate (66 mg, 0.18 mmol, as 2.5 hydrate) and (4'-trifluoromethyl-[1,1'-biphenyl]-2-yl) dicyclohexylphosphine oxide (155 mg, 0.36 mmol) obtained in Reference Example 12, and [the mixture] was stirred at room temperature for 1 hour. After Hhfa in a 1.0M dichloromethane solution (0.54 mL, 0.54 mmol) was delivered by drops into the reactant mixture, [the obtainment] was stirred at room temperature for 8 hours. The reaction liquid was concentrated under reduced pressure and recrystallized with acetone, and then, a white solid of bis [(4'-trifluoromethyl-[1,1'-biphenyl]-2-yl) dicyclohexylphosphine oxide] tris (hexafluoroacetylacetonato) europium (III) was obtained (yield amount: 161 mg, yield: 56%).

$^{19}$F-NMR (376 MHz, CDCl$_3$) δ (ppm): −62.5 (brs, 6F), −78.4 (brs, 18F). $^{31}$P-NMR (162 MHz, CDCl$_3$) δ (ppm): −80.5 (brs). ESIMS (m/z): 1434.2 [M-hfa]$^+$.

Example 12

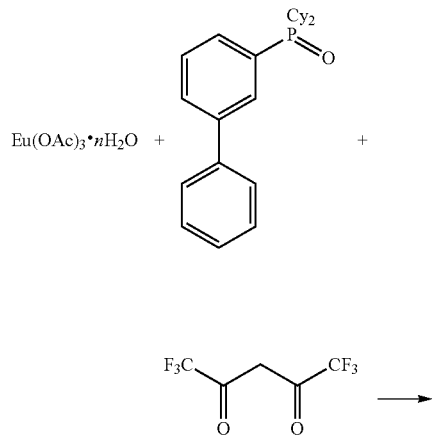

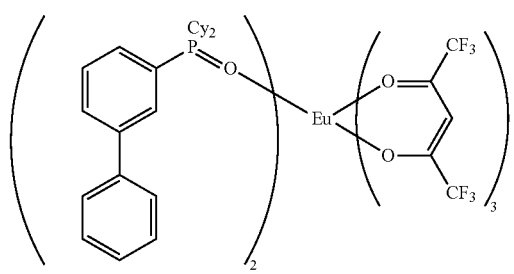

Under argon atmosphere, dichloromethane (3.0 mL) was added to europium (III) acetate hydrate (112 mg, 0.30 mmol, as 2.5 hydrate) and 3-biphenyl (dicyclohexyl) phosphine oxide (220 mg, 0.60 mmol) obtained in Reference Example 13, and [the mixture] was stirred at room temperature for 1 hour. After Hhfa in a 1.8M dichloromethane solution (0.50 mL, 0.90 mmol) was delivered by drops into the reactant mixture, and [the mixture] was stirred at room temperature for 5 hours. The reaction liquid was concentrated under reduced pressure and was recrystallized with dichloromethane/methanol, and then, a white solid of bis [3-biphenyl (dicyclohexyl) phosphine oxide] tris (hexafluoroacetylacetonato) europium (III) was obtained (yield amount: 250 mg, yield: 55%).

$^{19}$F-NMR (376 MHz, CDCl$_3$) δ (ppm): −78.2 (brs). $^{31}$P-NMR (162 MHz, CDCl$_3$), δ (ppm): −79.3 (brs). ESIMS (m/z): 1299.4 [M-hfa]$^+$.

Example 13

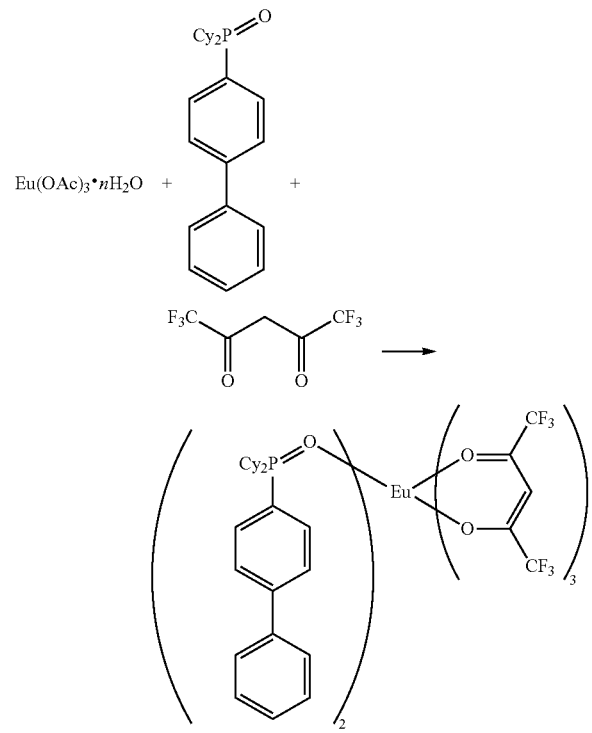

Under argon atmosphere, dichloromethane (3.0 mL) was added to europium (III) acetate hydrate (112 mg, 0.30 mmol, as 2.5 hydrate) and 4-biphenyl (dicyclohexyl) phosphine oxide (220 mg, 0.60 mmol) obtained in Reference Example 14, and [the mixture] was stirred at room temperature for 1 hour. After Hhfa in a 1.8M dichloromethane solution (0.50 mL, 0.90 mmol) was delivered by drops into the reactant mixture, [the mixture] was stirred at room temperature for 5 hours. The reaction liquid was concentrated under reduced pressure and was recrystallized with dichloromethane/hexane, and then, a white solid of bis [(4-biphenyl (dicyclohexyl) phosphine oxide] tris (hexafluoroacetylacetonato) europium (III) was obtained (yield amount: 350 mg, yield: 77%).

$^{19}$F-NMR (376 MHz, CDCl$_3$) δ (ppm): −78.2 (brs). $^{31}$P-NMR (162 MHz, CDCl$_3$), δ (ppm): −80.1 (brs). ESIMS (m/z): 1299.4 [M-hfa]$^+$.

Example 14

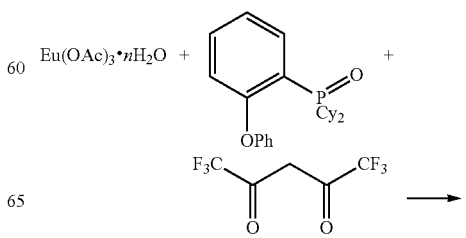

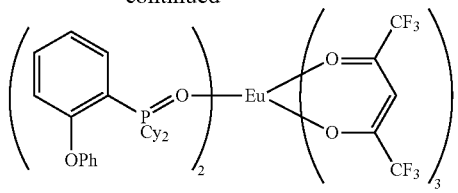

Under argon atmosphere, dichloromethane (3.0 mL) was added to europium (III) acetate hydrate (112 mg, 0.30 mmol, as 2.5 hydrate) and dicyclohexyl (2-phenoxyphenyl) phosphine oxide (230 mg, 0.60 mmol) obtained in Reference Example 15, and [the mixture] was stirred at room temperature for 1 hour. After Hhfa in a 1.8M dichloromethane solution (0.50 mL, 0.90 mmol) was delivered by drops into the reactant mixture, [the mixture] was stirred at room temperature for 8 hours. The reaction liquid was concentrated under reduced pressure and was recrystallized with dichloromethane/methanol, and then, a white solid of bis [dicyclohexyl (2-phenoxyphenyl) phosphine oxide] tris (hexafluoroacetylacetonato) europium (III) was obtained (yield amount: 229 mg, yield: 65%).

$^{19}$F-NMR (376 MHz, CDCl$_3$) δ (ppm): −78.2 (brs). $^{31}$P-NMR (162 MHz, CDCl$_3$) δ (ppm): −78.9 (brs). ESIMS (m/z): 1331.3 [M-hfa]$^+$.

Example 15

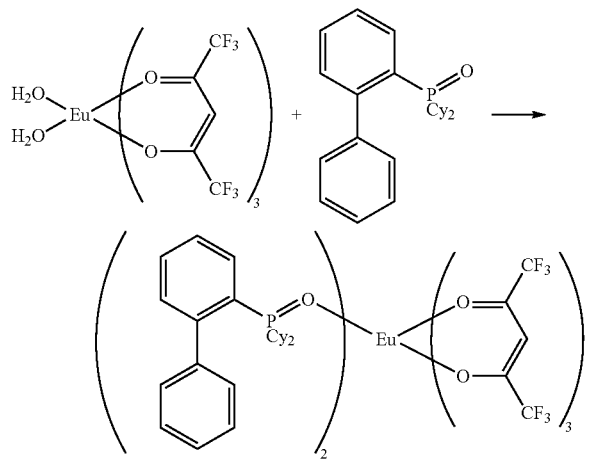

Under argon atmosphere, dichloromethane (3.0 mL) was added to diaqua-tris (hexafluoroacetylacetonato) europium (III) (243 mg, 0.30 mmol) obtained in Reference Example 16 and (2-biphenyl) dicyclohexylphosphine oxide (220 mg, 0.60 mmol) obtained in Reference Example 1, and [the mixture] was stirred at room temperature for 3 hours. After any insoluble matter was removed by filtration, the reaction liquid was concentrated under reduced pressure and was recrystallized with dichloromethane/methanol, and then, a reddish white solid of bis [(2-biphenyl) dicyclohexylphosphine oxide)] tris (hexafluoroacetylacetonato) europium (III) was obtained (yield amount: 336 mg, yield: 74%).

Example 16

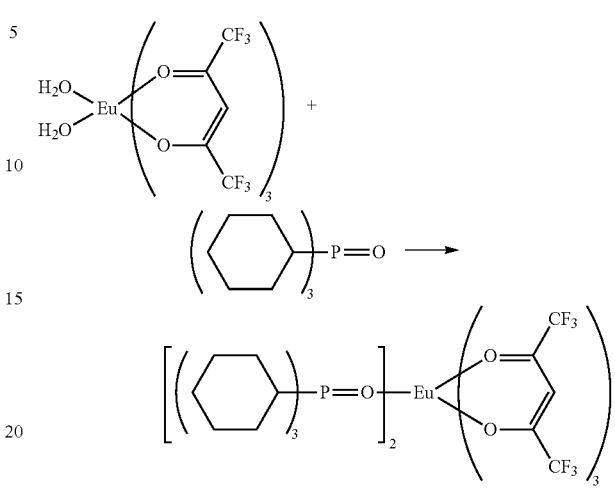

Under argon atmosphere, methanol (50.0 mL) was added to diaqua-tris (hexafluoroacetylacetonato) europium (III) (2.0 g, 24.7 mmol) obtained in Reference Example 16 and tricyclohexyl phosphine oxide (1.47 g, 4.94 mmol) obtained in Reference Example 8, and [the mixture] was stirred at 65° C. for 3 hours. The reaction liquid was filtrated, and the filtrate was concentrated under reduced pressure and was crystallized with methanol, and then, a white solid of bis (tricyclohexylphosphine) tris (hexafluoroacetylacetonato) europium (III) was obtained (yield amount: 2.4 g, yield: 71%).

Production Example 1

Into ethylene-vinyl acetate copolymer resin (manufactured by Tosoh Corporation, Ultrathene 720) (915 mg) in a toluene solution (4 mL), bis [(2-biphenyl) dicyclohexylphosphine oxide] tris (hexafluoroacetylacetonato) europium (III) (1 mg) in a toluene solution (1 mL) obtained in Example 1 was added. This mixture was stirred at room temperature for 30 minutes, and the obtained viscous liquid was applied onto a surface of a flat quartz glass substrate using a drop casting method, and [the quartz glass substrate] was dried under a condition of 60° C. of temperature for 24 hours, and an optical material containing bis [(2-biphenyl) dicyclohexylphosphine oxide] tris (hexafluoroacetylacetonato) europium (III) was produced.

Production Example 2

Into ethylene-vinyl acetate copolymer resin (manufactured by Tosoh Corporation, Ultrathene 720) (920 mg) in a toluene solution (4 mL), bis (tricyclohexylphosphine) tris (hexafluoroacetylacetonato) europium (III) (1 mg) in a toluene solution (1 mL) obtained in Example 8 was added. This mixture was stirred at room temperature for 30 minutes, and the obtained viscous liquid was applied onto a surface of a flat quartz glass substrate using a drop casting method, and [the quartz glass substrate] was dried under a condition of 60° C. of temperature for 24 hours, and an optical material containing bis (tricyclohexylphosphine) tris (hexafluoroacetylacetonato) europium (III) was produced.

Production Example 3

A mixture of methyl methacrylate monomer (70.0 g, 700 mmol), benzoyl peroxide (1.4 g, 5.8 mmol) as a polymerization initiator and bis (tricyclohexylphosphine) tris (hexafluoroacetylacetonato) europium (III) (70.4 mg, 0.051 mmol) obtained in Example 8 was added to a solution where purified water (208 mL) was added and dissolved into polyvinyl alcohol (4.2 g) as a dispersion stabilizer and sodium nitrite (0.21 g, 3.0 mmol) as a modifier. This mixture was stirred at 65° C. for 4 hours and the obtained white suspension was filtrated, and after [the obtainment] was washed with purified water, this was dried with heated air under reduced pressure (80° C., 2 hours), and an optical material (66.1 g) containing bis (tricyclohexylphospine) tris (hexafluoroacetylacetonato) europium (III) was produced.

Comparative Example 1

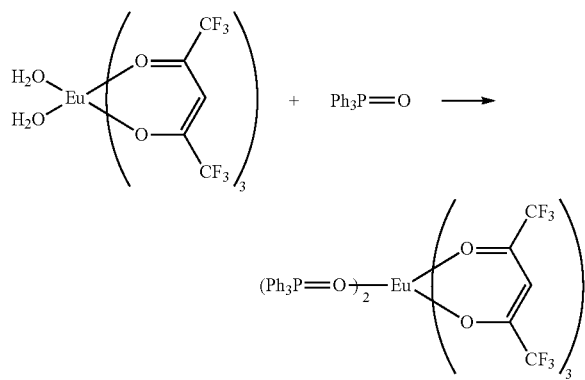

Under argon atmosphere, ethanol (200 mL) was added to diaqua-tris (hexafluoroacetylacetonato) europium (III) (5.0 g, 6.18 mmol) obtained in Reference Example 16 and triphenylphosphine oxide (3.4 g, 12.4 mmol), and [the mixture] was stirred at 65° C. for 3 hours. The reaction liquid was filtrated, and the filtrate was concentrated under reduced pressure and recrystallized with methanol, and then, a white solid of bis (triphenylphosphine oxide) tris (hexafluoroacetylacetonato) europium (III) was obtained (yield amount: 4.8 g, yield: 58%). Furthermore, this compound is a compound that is specifically described in RUB1453869 and JP-A-2003-81986.

$^{19}$F-NMR (376 MHz, CDCl$_3$), δ (ppm): −79.0 (brs).
$^{31}$P-NMR (162 MHz, CDCl$_3$), δ (ppm): −91.3 (brs). ESIMS (m/z): 1123.4 [M-hfa]+

Comparative Example 2

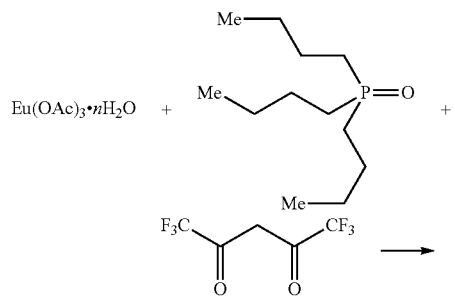

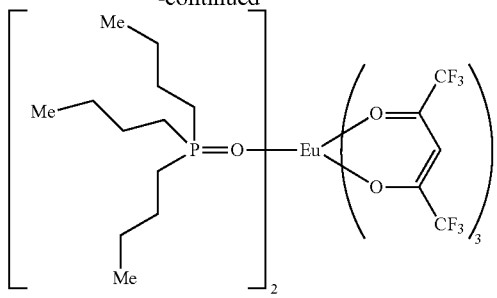

Under argon atmosphere, dichloromethane (3.0 mL) was added to europium (III) acetate hydrate (112 mg, 0.30 mmol, as 2.5 hydrate) and tributylphosphine oxide (131 mg, 0.60 mmol), and [the mixture] was stirred at room temperature for 1 hour. After Hhfa in a 1.8M dichloromethane solution (0.50 mL, 0.90 mmol) was delivered by drops into the reactant mixture, [the mixture] was stirred at room temperature for 5 hours. The reaction liquid was concentrated under reduced pressure and recrystallized with dichloromethane/hexane, and then, a white solid of bis (tributylphosphine oxide) tris (hexafluoroacetylacetonato) europium (III) was obtained (yield amount: 243 mg, yield: 67%).

$^{19}$F-NMR (376 MHz, CDCl$_3$), δ (ppm): −78.0 (brs).
$^{31}$P-NMR (162 MHz, CDCl$_3$), δ (ppm): −63.0 (brs). ESIMS (m/z): 1003.0 [M-hfa]$^+$.

Evaluation Example

Evaluating samples for emission spectrum measurement and light resistance of the europium complexes of the present invention and the europium complexes obtained in Comparative Examples 1 to 2 were produced by crushing powder of the europium complexes synthesized in Examples 1 to 14 and the europium complexes obtained in Comparative Examples 1 to 2 with mortars to be fine powder, and by filling the powder to powder cells (manufactured by JASCO Corporation, PSH-002) under dry air atmosphere.

Measurement results of emission spectrums (excitation light: 380 nm) of the europium complexes obtained in Examples 1 to 14 are shown in FIGS. 1 to 14, respectively, and measurement results of emission spectrums (excitation light: 380 nm) of optical materials containing the europium complexes obtained in Production Examples 1 to 3 are shown in FIGS. 15 to 17, respectively. The measurement conditions were 1 nm of slit at the excitation side and 1 nm of slit at the fluorescence side. Emission of lights at approximately 593 nm, 612 nm, 653 nm and 699 nm based upon f-f electronic transition, which is characteristic in Eu (III) complex, was observed.

Evaluation results of luminescent quantum yields at the wavelength 380 nm of excitation light of the europium complexes obtained in Examples 1 to 14 are shown in Table 1.

TABLE 1

| Sample | Luminescent quantum yield (%) |
|---|---|
| Example 1 | 54% |
| Example 2 | 72% |
| Example 3 | 70% |
| Example 4 | 60% |

TABLE 1-continued

| Sample | Luminescent quantum yield (%) |
|---|---|
| Example 5 | 56% |
| Example 6 | 71% |
| Example 7 | 64% |
| Example 8 | 71% |
| Example 9 | 66% |
| Example 10 | 60% |
| Example 11 | 64% |
| Example 12 | 58% |
| Example 13 | 68% |
| Example 14 | 75% |

The light resistance was evaluated using the method shown below. For the evaluation of the light resistance in Examples 1 to 14 and Comparative Examples 1 to 2, intensity of emission at the maximum emission wavelength in the vicinity of 615 nm was measured with a spectrophotometer (manufactured by JASCO Corporation, FP-6500). The measurement conditions were 5 nm of slit at the excitation side and 5 nm of slit at the fluorescence side. Next, at room temperature, ultra violet rays at 200 mW/cm$^2$ (365 nm) were irradiated for a predetermined time (0 to 24 hours) by using an ultraviolet ray irradiator (manufactured by Ushio Inc., SP-9) and a lens. The intensity of emission of the samples after being irradiated with the ultraviolet rays was measured again with the spectrophotometer, and residual ratios of the intensity of emission from the initial state were calculated by an expression below, and the light resistance was evaluated by setting the irradiation time of ultraviolet ways on the X axis and setting the residual ratio of the intensity of emission on the Y axis.

Residual ratio of intensity of emission (%)($I/I_0$)=
(intensity of emission at maximum emission wavelength after irradiation of ultraviolet rays)/
intensity of emission at maximum emission wavelength before irradiation of ultraviolet rays)×100

The evaluation results of the light resistance of the europium complexes of the present invention obtained in Examples 1 to 14 were shown in FIGS. 18 to 31 along with the results of Comparative Examples 1 and 2, respectively, and results of the residual ratios of the intensity of emission after 24 hours of the irradiation of the ultraviolet rays obtained as a result were shown in Table 2.

TABLE 2

| Sample | Residual ratio of intensity of emission (%) |
|---|---|
| Example 1 | 98% |
| Example 2 | 91% |
| Example 3 | 99% |
| Example 4 | 90% |
| Example 5 | 96% |
| Example 6 | 96% |
| Example 7 | 93% |
| Example 8 | 93% |
| Example 9 | 79% |
| Example 10 | 90% |
| Example 11 | 93% |
| Example 12 | 88% |
| Example 13 | 97% |
| Example 14 | 97% |
| Comparative Example 1 | 46% |

TABLE 2-continued

| Sample | Residual ratio of intensity of emission (%) |
|---|---|
| Comparative Example 2 | 70% |

As shown in FIGS. 18 to 31, It has been found that the europium complex of the present invention has excellent light resistance by significantly suppressing a decrease in emission intensity due to ultraviolet ray irradiation by introducing a specific substituent on the phosphorus atom.

In the meantime, in the compound specifically described in RUB1453869 and JP-A-2003-81986 (Comparative Example 1) and in the europium complex having a linear alkyl group on the phosphorus atom disclosed in JP-A-2005-223276 (Comparative Example 2), a decrease in the intensity of emission by the irradiation of ultraviolet rays is significant.

Reference Example 17

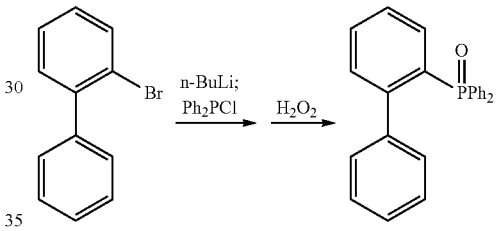

Under argon atmosphere, 2-bromobiphenyl (1.40 g, 6.00 mmol) was dissolved into diethyl ether (10 mL), and [the obtainment] was cooled down to −15° C. In to this solution, n-butyllithium in a 2.67M hexane solution (2.4 mL, 6.41 mmol) was delivered by drops, and after stirring for 2 hours, chlorodiphenylphosphine in a 0.54M diethyl ether solution (10 mL, 5.4 mmol) was added, and [the mixture] was slowly heated to room temperature and stirred for 3 hours. The reaction liquid was filtrated, and the filtrate was concentrated under reduced pressure, and the obtained crude product was refined by silica gel column chromatography (eluent: hexane/ethyl acetate), and then, a white solid of (2-biphenyl) diphenyl phosphine was obtained (yield amount: 1.6 g, yield: 79%).

$^1$H-NMR (400 MHz, CDCl$_3$), δ (ppm): 7.41~7.37 (m, 1H), 7.34~7.16 (m, 17H), 7.07~7.04 (m, 1H). $^{31}$P-NMR (162 MHz, CDCl$_3$), δ (ppm): −13.5 (s).

The above-mentioned (2-biphenyl) diphenylphosphine (341 mg, 1.01 mmol) was dissolved into dichloromethane (5 mL), and a 30% hydrogen peroxide solution (2.4 mL) was added to this [obtainment], and [the mixture] was stirred at room temperature for 3.5 hours. Water (15 mL) was poured into the reactant mixture, and after organic layers were separated, chloroform (15 mL) was added to an aqueous layer, and a chloroform layer was separated. This operation was repeated twice. The above-mentioned organic layers were combined, and after these were dried with sodium sulfate, they were concentrated under reduced pressure. A white solid of (2-biphenyl) diphenylphosphine oxide was obtained by refining the obtained crude product by silica gel column chromatography (eluent: chloroform/methanol) (yield amount: 300 mg, yield: 84%).

$^1$H-NMR (400 MHz, CDCl$_3$), δ (ppm): 7.59~7.53 (m, 5H), 7.44~7.28 (m, 9H), 7.22~7.19 (m, 2H), 7.07~7.02 (m, 3H). $^{31}$P-NMR (162 MHz, CDCl$_3$), δ (ppm): 27.8 (s).

Reference Example 18

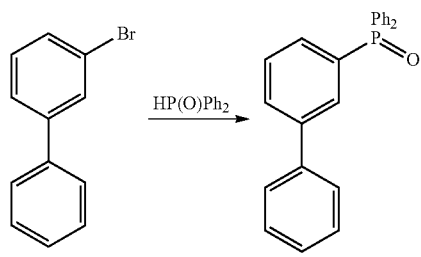

Under argon atmosphere, 3-bromo-2,2'-biphenyl (280 mg, 1.20 mmol), nickel chloride hexahydrate (23.8 mg, 0.10 mmol), 2,2'-bipyridyl (31.2 mg, 0.20 mmol), zinc powder (131 mg, 2.00 mmol) and diphenylphosphine oxide (202 mg, 1.00 mmol) were suspended into water (2.0 mL), and [the suspension] was stirred at 70° C. for 16 hours. Chloroform (4.0 mL) and water (2.0 mL) were poured into the reactant mixture, and [the mixture] was filtrated and the residue was washed with chloroform. After the filtrate was separated, an aqueous layer was extracted with chloroform (10 mL×2), and the combined organic layer was dried with magnesium sulfate, and was concentrated under reduced pressure. By refining the obtained crude product by silica gel column chromatography (eluent: hexane/ethyl acetate), (3-biphenyl) diphenylphosphine oxide (316 mg, yield: 89%) was obtained as a white solid.

$^1$H-NMR (400 MHz, CDCl$_3$), δ (ppm): 7.95 (brd, J=12.6 Hz, 1H), 7.77 (brd, J=7.6 Hz, 1H), 7.75~7.67 (m, 4H), 7.63~7.39 (m, 12H), 7.35 (brdd, J=7.3, 7.3 Hz, 1H). $^{31}$P-NMR (162 MHz, CDCl$_3$), δ (ppm): 29.1 (s).

Reference Example 19

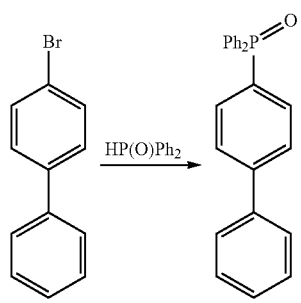

Under argon atmosphere, 4-bromo-2,2'-biphenyl (280 mg, 1.20 mmol), nickel chloride hexahydrate (23.8 mg, 0.10 mmol), 2,2'-bipyridyl (31.2 mg, 0.20 mmol), zinc powder (131 mg, 2.00 mmol) and diphenylphosphine oxide (202 mg, 1.00 mmol) were suspended into water (2.0 mL), and [the suspension] was stirred at 70° C. for 16 hours. Chloroform (4.0 mL) and water (2.0 mL) were poured into the reactant mixture, and [the mixture] was filtrated and the residue was washed with chloroform. After the filtrate was separated, an aqueous layer was extracted with chloroform (10 mL×2), and the combined organic layers were dried with magnesium sulfate and were concentrated under reduced pressure. By refining the obtained crude product by silica gel column chromatography (eluent: hexane/ethyl acetate), (4-biphenyl)diphenylphosphine oxide (344 mg, yield: 97%) was obtained as a white solid.

$^1$H-NMR (400 MHz, CDCl$_3$), δ (ppm): 7.77~7.66 (m, 8H), 7.63~7.53 (m, 4H), 7.52~7.43 (m, 6H), 7.39 (brdd, J=7.3, 7.3 Hz, 1H). $^{31}$P-NMR (162 MHz, CDCl$_3$), δ (ppm): 29.0 (s).

Reference Example 20

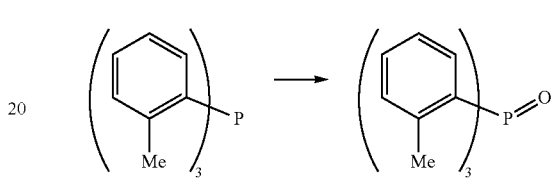

Tri (o-tolyl) phosphine (1.01 g, 3.03 mmol) was dissolved into dichloromethane (10 mL), and a 30% hydrogen peroxide solution (1.0 mL) was added, and [the mixture] was stirred at room temperature for 2.5 hours. Water (10 mL) was poured into the reactant mixture, and after organic layers were separated, chloroform (10 mL) was added into an aqueous layer, and a chloroform layer was separated. This operation was repeated twice. The organic layers were combined, and after the combined layers were dried with magnesium sulfate and were concentrated under reduced pressure. A white solid of tri (o-tolyl) phosphine oxide was obtained by refining the obtained crude product by silica gel column chromatography (eluent: chloroform/methanol) (yield amount: 448 mg, yield: 42%).

$^1$H-NMR (400 MHz, CDCl$_3$), δ (ppm): 7.43 (brdd, J=7.5, 7.4 Hz, 3H), 7.32 (brdd, J=7.5, 4.1 Hz, 3H), 7.19~7.05 (m, 6H), 2.50 (s, 9H). $^{31}$P-NMR (162 MHz, CDCl$_3$), δ (ppm): 37.1 (s).

Reference Example 21

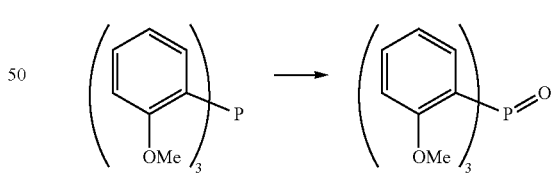

Tris (2-methoxyphenyl) phosphine (2.00 g, 5.68 mmol) was dissolved into dichloromethane (20 mL), and a 30% hydrogen peroxide solution (3.5 mL) was added and [the mixture] was stirred at room temperature for 1 hour. Water (60 mL) was poured into the reactant mixture, and after organic layers were separated, chloroform (50 mL) was added to an aqueous layer, and a chloroform layer was separated. This operation was repeated twice. The organic layers were combined, and after [the combined layers] were dried with magnesium sulfate, it was concentrated under reduced pressure. A white solid of tris (2-methoxyphenyl) phosphine oxide was obtained by refining the crude product by silica gel column chromatography (eluent: chloroform/methanol) (yield amount: 1.85 g, yield: 88%).

$^1$H-NMR (400 MHz, CDCl$_3$), δ (ppm): 7.54~7.43 (m, 6H), 6.98 (td, J=7.6, 2.3 Hz, 3H), 6.90 (dd, J=5.3, 2.3 Hz, 3H), 3.57 (s, 9H). $^{31}$P-NMR (162 MHz, CDCl$_3$), δ (ppm): 25.6 (s).

Reference Example 22

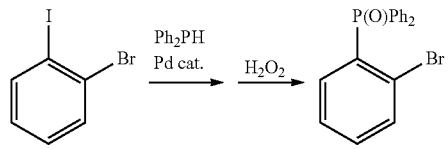

Under argon atmosphere, N,N-dimethylacetamide (55.0 mL) was added to 1-bromo-2-iodobenzene (7.23 g, 25.6 mmol), diphenyl phosphine (4.71 g, 25.3 mmol), palladium (II) acetate (30.4 mg, 0.135 mmol) and sodium acetate (2.28 g, 27.8 mmol), and [the mixture] was stirred at 130° C. for 3 days. Water (100 mL) was poured into the reactant mixture, and an aqueous layer was extracted with chloroform (60 mL) twice. After combined organic layers were washed with 100 mL of water four times, the layers were dried with sodium sulfate, and then these were concentrated under reduced pressure. A white solid of (2-bromophenyl) diphenyl phosphine was obtained by refining the obtained crude product by silica gel column chromatography (eluent: hexane/ethyl acetate) (yield amount: 6.07 g, yield: 70%).

$^1$H-NMR (400 MHz, CDCl$_3$), δ (ppm): 7.59 (m, 1H), 7.38~7.32 (m, 6H), 7.30~7.25 (m, 4H), 7.21~7.16 (m, 2H), 6.76 (m, 1H). $^{31}$P-NMR (162 MHz, CDCl$_3$), δ (ppm): −5.1 (s).

The (2-bromophenyl) diphenyl phosphine (6.07 g, 17.8 mmol) was dissolved into dichloromethane (35 mL), and after [the obtainment] was cooled down to 0° C., a 30% hydrogen peroxide solution (10 mL) was added, and [the mixture] was stirred at room temperature for 1 hour. Water (20 mL) was poured into the reactant mixture, and after organic layers were separated, chloroform (50 mL) was added to an aqueous layer, and a chloroform layer was separated. This operation was repeated twice. The organic layers were combined, and after these were dried with sodium sulfate, they were concentrated under reduced pressure. By refining the obtained crude product by silica gel column chromatography (eluent: chloroform/methanol), (2-bromophenyl) diphenylphosphine oxide (yield amount: 6.00 g, yield: 94%) was obtained.

$^1$H-NMR (400 MHz, CDCl$_3$), δ (ppm): 7.74~7.66 (m, 5H), 7.59~7.55 (m, 2H), 7.51~7.46 (m, 4H), 7.41~7.32 (m, 3H). $^{31}$P-NMR (162 MHz, CDCl$_3$), δ (ppm): 30.5 (s).

Reference Example 23

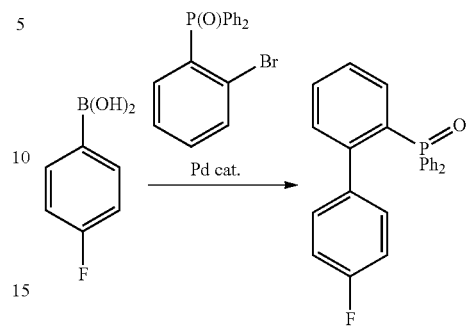

Under argon atmosphere, 1,4-dioxane (5.0 mL) was added to (2-bromophenyl) diphenylphosphine oxide (500 mg, 1.40 mmol) obtained in Reference Example 22, 4-fluorophenylboronic acid (196 mg, 1.40 mmol), triphenylphosphine (44 mg, 0.168 mmol), tripotassium phosphate (590 mg, 2.78 mmol) and bis (dibenzylideneacetone) palladium (0) (24 mg, 0.0417 mmol), and [the mixture] was stirred at 100° C. for 14 hours. Water (30 mL) was poured into the reactant mixture, and chloroform (20 mL) was added to an aqueous layer, and a chloroform layer was separated. This operation was repeated twice. The organic layers were combined, and after these were dried with sodium sulfate, they were concentrated under reduced pressure. A white solid of (4'-fluoro [1,1'-biphenyl]-2-yl) diphenylphosphine oxide was obtained by refining the obtained crude product by silica gel column chromatography (eluent: hexane/ethyl acetate) (yield amount: 431 mg, yield: 83%).

$^1$H-NMR (400 MHz, CDCl$_3$), δ (ppm): 7.59~7.53 (m, 5H), 7.43~7.29 (m, 9H), 7.18 (dd, J=8.6, 5.2 Hz, 2H), 6.73 (t, J=8.6 Hz, 2H). $^{19}$F-NMR (376 MHz, CDCl$_3$), δ (ppm): −115.5 (s) $^{31}$P-NMR (162 MHz, CDCl$_3$), δ (ppm): 27.7 (s).

Reference Example 24

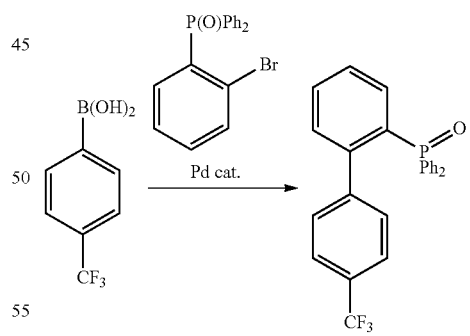

Under argon atmosphere, 1,4-dioxane (5.0 mL) was added to (2-bromophenyl) diphenylphosphine oxide (500 mg, 1.40 mmol) obtained in Reference Example 22, 4-(trifluoromethyl) phenylboronic acid (266 mg, 1.40 mmol), triphenylphosphine (44 mg, 0.168 mmol), tripotassium phosphate (590 mg, 2.78 mmol) and bis (dibenzylideneacetone) palladium (0) (24 mg, 0.0417 mmol), and [the mixture] was stirred at 100° C. for 14 hours. Water (30 mL) was poured into the reactant mixture, and chloroform (20 mL) was added to an aqueous layer and a chloroform layer was separated. This operation was repeated twice. The organic layers were combined, and after these were dried with sodium sulfate, they were concentrated under reduced pressure. A white solid of (4'-trifluoromethyl [1,1'-biphenyl]-2-yl) diphenylphosphine oxide was obtained by refining the obtained crude product by silica gel column chromatography (eluent: hexane/ethyl acetate) (yield amount: 413 mg, yield: 70%).

$^1$H-NMR (400 MHz, CDCl$_3$), δ (ppm): 7.60~7.54 (m, 5H), 7.46~7.36 (m, 4H), 7.34~7.27 (m, 9H). $^{19}$F-NMR (376 MHz, CDCl$_3$), δ (ppm): −62.8 (s)$^{31}$P-NMR (162 MHz, CDCl$_3$), δ (ppm): 27.2 (s).

Reference Example 25

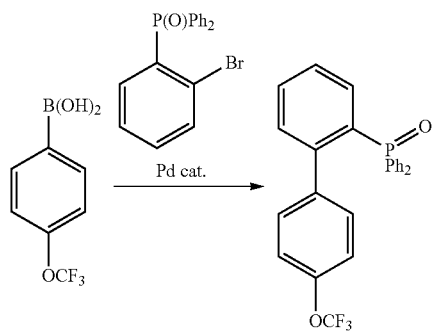

Under argon atmosphere, 1,4-dioxane (5.0 mL) was added to (2-bromophenyl)diphenylphosphine oxide (500 mg, 1.40 mmol) obtained in Reference Example 22, 4-(trifluoromethoxy) phenylboronic acid (288 mg, 1.40 mmol), triphenylphosphine (44 mg, 0.17 mmol), tripotassium phosphate (590 mg, 2.78 mmol) and bis (dibenzylideneacetone) palladium (0) (24 mg, 0.042 mmol), and [the mixture] was stirred at 100° C. for 14 hours. Water (30 mL) was poured into the reactant mixture, and chloroform (20 mL) was added to an aqueous layer and a chloroform layer was separated. This operation was repeated twice. The organic layers were combined, and after these were dried with sodium sulfate, they were concentrated under reduced pressure. A white solid of (4'-trifluoromethoxy [1,1'-biphenyl]-2-yl) diphenylphosphine oxide was obtained by refining the obtained crude product by silica gel column chromatography (eluent: hexane/ethyl acetate) (yield amount: 157 mg, yield: 26%).

$^1$H-NMR (400 MHz, CDCl$_3$), δ (ppm): 7.60~7.55 (m, 5H), 7.43~7.24 (m, 11H), 6.88 (d, J=8.1 Hz, 2H). $^{19}$F-NMR (376 MHz, CDCl$_3$), δ (ppm): −57.7 (s)$^{31}$P-NMR (162 MHz, CDCl$_3$), δ (ppm): 27.3 (s).

Reference Example 26

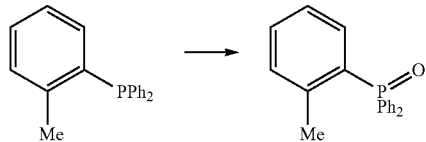

Diphenyl (o-tolyl) phosphine (1.00 g, 3.62 mmol) was dissolved into dichloromethane (5.0 mL), and after [the obtainment] was cooled down to 0° C., a 30% hydrogen peroxide solution (2.0 mL) was added, and [the mixture] was stirred at room temperature for 1 hour. Water (10 mL) was poured into the reactant mixture, and after organic layers were separated, chloroform (20 mL) was added to an aqueous layer and a chloroform layer was separated. This operation was repeated twice. The organic layers were combined, and after these were dried with sodium sulfate, they were concentrated under reduced pressure. A white solid of diphenyl (o-tolyl) phosphine oxide was obtained by refining the obtained crude product by silica gel column chromatography (eluent: chloroform/methanol) (yield amount: 948 mg, yield: 90%).

$^1$H-NMR (400 MHz, CDCl$_3$), δ (ppm): 7.68~7.62 (m, 4H), 7.57~7.52 (m, 2H), 7.49~7.39 (m, 5H), 7.30~7.27 (m, 1H), 7.16~7.10 (m, 1H), 7.06~6.99 (m, 1H), 2.45 (s, 3H). $^{31}$P-NMR (162 MHz, CDCl$_3$), δ (ppm): 31.5 (s).

Reference Example 27

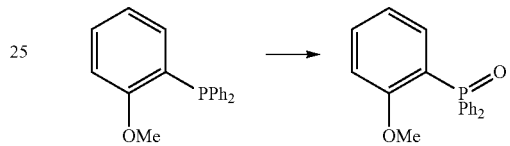

Diphenyl (2-methoxyphenyl) phosphine (1.08 g, 3.68 mmol) was dissolved into dichloromethane (5.0 mL), and after [the obtainment] was cooled down to 0° C., a 30% hydrogen peroxide solution (2.0 mL) was added, and [the mixture] was stirred at room temperature for 1 hour. Water (10 mL) was poured into the reactant mixture, and after organic layers were separated, chloroform (20 mL) was added to an aqueous layer, and a chloroform layer was separated. This operation was repeated twice. The organic layers were combined, and after these were dried with sodium sulfate, they were concentrated under reduced pressure. A white solid of diphenyl (2-methoxyphenyl) phosphine oxide was obtained by refining the obtained crude product by silica gel column chromatography (eluent: chloroform/methanol) (yield amount: 986 mg, yield: 87%).

$^1$H-NMR (400 MHz, CDCl$_3$), δ (ppm): 7.80~7.65 (m, 5H), 7.56~7.47 (m, 3H), 7.46~7.39 (m, 4H), 7.08 (t, J=7.8 Hz, 1H), 6.92 (dd, J=7.8, 5.2 Hz, 1H), 3.56 (s, 3H). $^{31}$P-NMR (162 MHz, CDCl$_3$), δ (ppm): 27.2 (s).

Example 17

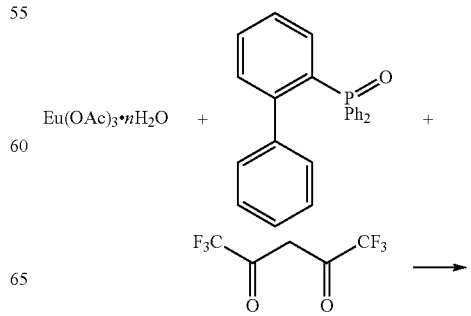

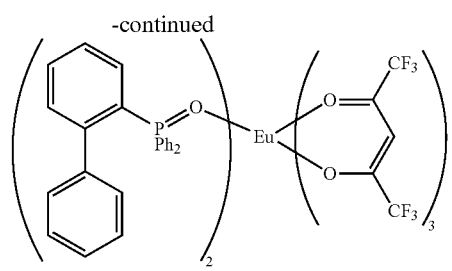

Under argon atmosphere, dichloromethane (40 mL) was added to europium (III) acetate hydrate (1.12 g, 2.9 mmol as 2.5 hydrate) and (2-biphenyl) diphenylphosphine oxide (2.13 g, 6.02 mmol) obtained in Reference Example 17, and [the mixture] was stirred at room temperature for 1 hour. After Hhfa in a 2.0M dichloromethane solution (4.5 mL, 9.0 mmol) was delivered by drops into the reactant mixture, [the mixture] was stirred at room temperature for 3 hours. The reaction liquid was filtrated, and the filtrate was concentrated under reduced pressure and recrystallized with dichloromethane/hexane, and then, a white solid of bis [(2-biphenylyl) diphenylphosphine oxide] tris (hexafluoroacetylacetonato) europium (III) was obtained (yield amount: 3.09 g, yield: 68% as 2.99 mmol of europium (III) acetate hydrate was used).

$^{19}$F-NMR (376 MHz, CDCl$_3$), δ (ppm): −76.1 (brs). $^{31}$P-NMR (162 MHz, CDCl$_3$), δ (ppm): −92.5 (brs). ESIMS (m/z): 1275.6 [M-hfa]$^+$. Anal. Calcd. for [C$_{63}$H$_{41}$EuF$_{18}$O$_8$P$_2$]: C, 51.06%: H, 2.79%. Found: C, 50.94%; H, 2.90%. Further, single crystal X-ray structural analysis of bis [(2-biphenyl) diphenylphosphine oxide)] tris (hexafluoroacetylacetonato) europium (III) was conducted. Results of the single crystal X-ray structural analysis are shown below, and an obtained crystal structure due to this analysis is shown in FIG. 32.

Monoclinic (P121)
a=13.540 (3) Å
b=11.657 (4) Å
c=19.191 (8) Å
β=97.74 (3°)
V=3001.3 (17) Å$^3$
Z=2
R1=0.1090
wR2=0.3838

Example 18

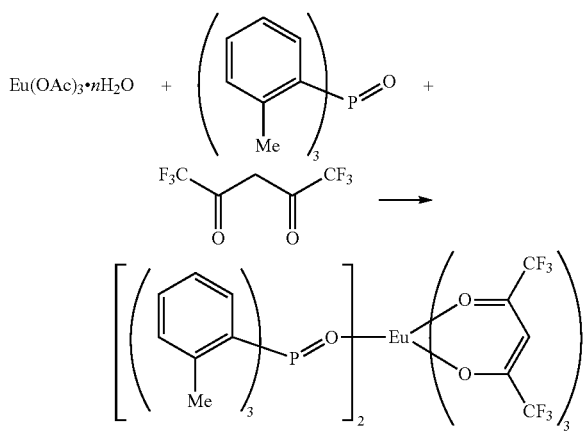

Under argon atmosphere, dichloromethane (5.0 mL) was added to europium (III) acetate hydrate (132 mg, 0.353 mmol as 2.5 hydrate) and tri (o-tolyl) phosphine oxide (256 mg, 0.80 mmol) obtained in Reference Example 20, and [the mixture] was stirred at room temperature for 1 hour. After Hfac in a 1.8M dichloromethane solution (0.67 mL, 1.2 mmol) was delivered by drops into the reactant mixture, [the mixture] was stirred at room temperature for 3 hours. The reaction liquid was filtrated, the filtrate was concentrated under reduced pressure and was recrystallized with methanol, and then, a reddish white solid of bis [tri (o-tolyl) phosphine oxide] tris (hexafluoroacetylacetonato) europium (III) was obtained (yield amount: 364 mg, yield: 73% as 0.353 mmol of europium (III) acetate hydrate was used).

$^{19}$F-NMR (376 MHz, CDCl$_3$), δ (ppm): −79.1 (s). $^{31}$P-NMR (162 MHz, CDCl$_3$), δ (ppm): −104 (brs). ESIMS (m/z): 1207.4 [M-hfa]$^+$.

Example 19

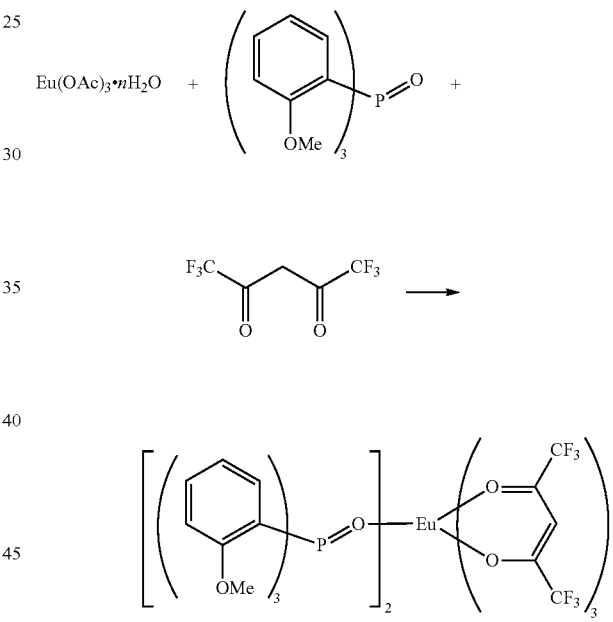

Under argon atmosphere, dichloromethane (5.0 mL) was added to europium (III) acetate hydrate (131 mg, 0.350 mmol as 2.5 hydrate) and tris (2-methoxyphenyl) phosphine oxide (258 mg, 0.700 mmol) obtained in Reference Example 21, and [the mixture] was stirred at room temperature for 1 hour. After Hhfa in a 2.1M dichloromethane solution (0.50 mL, 1.05 mmol) was delivered by drops into the reactant mixture, [the obtainment] was stirred at room temperature for 3 hours. The reaction liquid was concentrated under reduced pressure and was recrystallized with methanol, and then, a white solid of tris [tris (2-methoxyphenyl) phosphine oxide] tris (hexafluoroacetylacetonato) europium (III) was obtained (yield amount: 344 mg, yield: 65% as 0.350 mmol of europium (III) acetate hydrate was used).

$^{19}$F-NMR (376 MHz, CDCl$_3$), δ (ppm): −78.7 (brs). $^{31}$P-NMR (162 MHz, CDCl$_3$), δ (ppm): −118.5 (brs). ESIMS (m/z): 1303.5 [M-hfa]$^+$.

Example 20

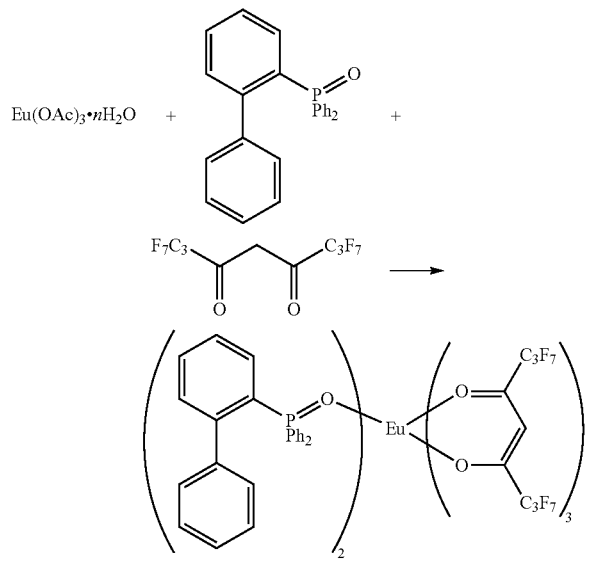

Under argon atmosphere, dichloromethane (3.0 mL) was added to europium (III) acetate hydrate (74.8 mg, 0.200 mmol, as 2.5 hydrate) and (2-biphenyl)diphenylphosphine oxide (142 mg, 0.401 mmol) obtained in Reference Example 17, and [the mixture] was stirred at room temperature for 1 hour. After 1,1,1,2,2,3,3,7,7,8,8,9,9,9-tetradeca-fluoro-4,6-nonanedione (0.15 mL, 0.603 mmol) was delivered by drops into the reactant mixture, [the mixture] was stirred at room temperature for 10 hours. The reaction liquid was filtrated, and the filtrate was concentrated under reduced pressure and recrystallized with methanol, and then, a white solid of bis [(2-biphenyl) diphenylphosphine oxide] tris (1,1,1,2,2,3,3,7,7,8,8,9,9,9-tetradeca-fluoro-4,6-dioxononane-5-id) europium (III) was obtained (yield amount: 278 mg, yield: 67% as 0.200 mmol of europium (III) acetate hydrate was used).

$^{19}$F-NMR (376 MHz, CDCl$_3$), δ (ppm): −80.9 (brs, 18F), −123.1 (brs, 12F), −127.0 (brs, 12F). $^{31}$P-NMR (162 MHz, CDCl$_3$), δ (ppm): −106.8 (brs). ESIMS (m/z): 1675.5 [M-tdf]$^+$.

Example 21

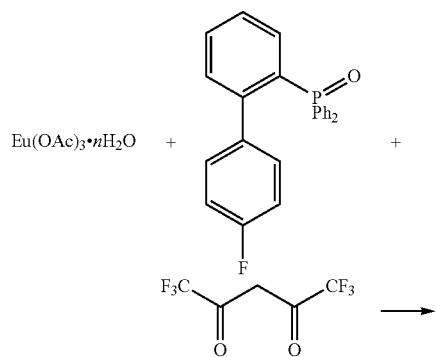

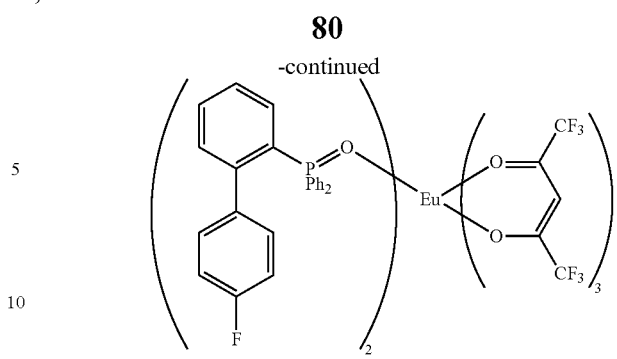

Under argon atmosphere, dichloromethane (4.0 mL) was added to europium (III) acetate hydrate (112 mg, 0.299 mmol as 2.5 hydrate) and (4'-fluoro [1,1'-biphenyl]-2-yl) diphenylphosphine oxide (223 mg, 0.599 mmol) obtained in Reference Example 23, and [the mixture] was stirred at room temperature for 1 hour. After Hhfa in a 1.8M dichloromethane solution (0.5 mL, 0.90 mmol) was delivered by drops into the reactant mixture, [the mixture] was stirred at room temperature for 12 hours. The reaction liquid was concentrated under reduced pressure and recrystallized with dichloromethane/hexane, and then, a reddish white solid of bis [(4'-fluoro [1,1'-biphenyl]-2-yl)diphenylphosphine oxide] tris (hexafluoroacetylacetonato) europium (III) was obtained (yield amount: 349 mg, yield: 77% as 0.299 mmol of europium (III) acetate hydrate was used).

$^{19}$F-NMR (376 MHz, CDCl$_3$), δ (ppm): −79.0 (brs, 18F), −113.6 (brs, 2F). $^{31}$P-NMR (162 MHz, CDCl$_3$), δ (ppm): −92.1 (brs). ESIMS (m/z): 1311.2 [M-hfa]$^+$.

Example 22

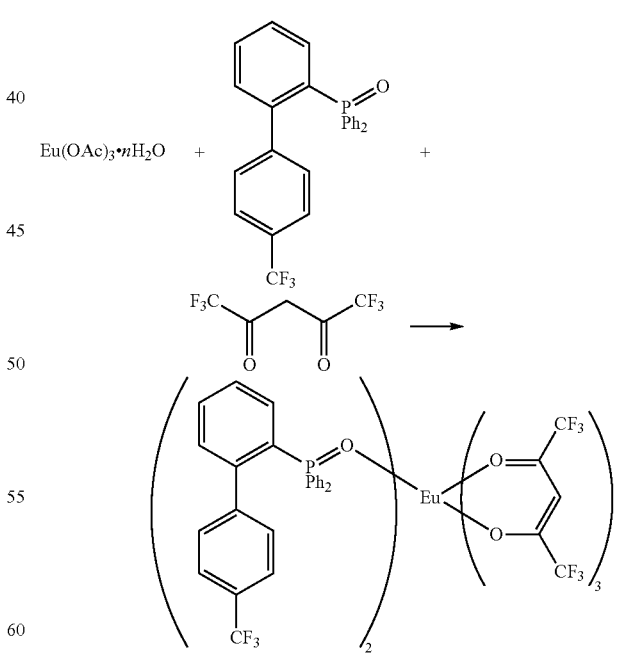

Under argon atmosphere, dichloromethane (4.0 mL) was added to europium (III) acetate hydrate (112 mg, 0.299 mmol as 2.5 hydrate) and (4'-trifluoromethyl [1,1'-biphenyl]-2-yl)diphenylphosphine oxide (253 mg, 0.599 mmol) obtained in Reference Example 24, and [the mixture was stirred at room temperature for 1 hour. After Hhfa in a 0.9M dichloromethane solution (1.0 mL, 0.90 mmol) was delivered by drops into the reactant mixture, [the mixture] was stirred at room temperature for 6 hours. The reaction liquid was concentrated under reduced pressure and recrystallized with acetone/methanol, and then, a reddish white solid of bis [(4'-trifluoromethyl [1,1'-biphenyl]-2-yl) diphenylphosphine oxide] tris (hexafluoroacetylacetonato) europium (III) was obtained (yield amount: 286 mg, yield: 59% as 0.299 mmol of europium (III) acetate hydrate was used).

$^{19}$F-NMR (376 MHz, CDCl$_3$), δ (ppm): −62.0 (brs, 6F), −79.1 (brs, 18F). $^{31}$P-NMR (162 MHz, CDCl$_3$), δ (ppm): −91.7 (brs). ESIMS (m/z): 1411.3 [M-hfa]$^+$.

Example 23

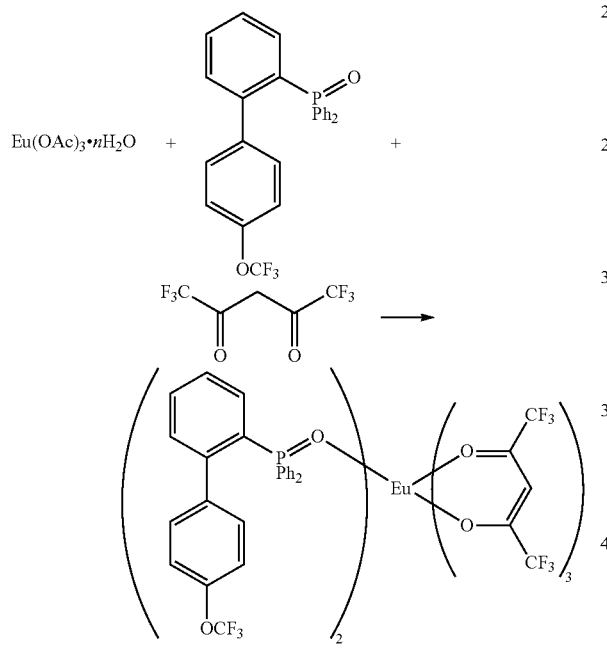

Under argon atmosphere, dichloromethane (3.0 mL) was added to europium (III) acetate hydrate (56 mg, 0.150 mmol as 2.5 hydrate) and (4'-trifluoromethoxy [1,1'-biphenyl]-2-yl)diphenylphosphine oxide (132 mg, 0.301 mmol) obtained in Reference Example 25, and [the mixture] was stirred at room temperature for 1 hour. After Hhfa in a 0.9M dichloromethane solution (0.5 mL, 0.45 mmol) was delivered by drops into the reacted mixture, [the mixture] was stirred at room temperature for 6 hours. The reaction liquid was concentrated under reduced pressure and recrystallized with dichloromethane/hexane, and then, a reddish white solid of bis [(4'-trifluoromethoxy[1,1'-biphenyl]-2-yl)diphenylphosphine oxide] tris (hexafluoroacetylacetonato) europium (III) was obtained (yield amount: 195 mg, yield: 79% as 0.150 mmol of europium (III) acetate hydrate was used).

$^{19}$F-NMR (376 MHz, CDCl$_3$), δ (ppm): −56.7 (brs, 6F), −79.1 (brs, 18F). $^{31}$P-NMR (162 MHz, CDCl$_3$), δ (ppm): −92.5 (brs). ESIMS (m/z): 1443.3 [M-hfa]$^+$.

Example 24

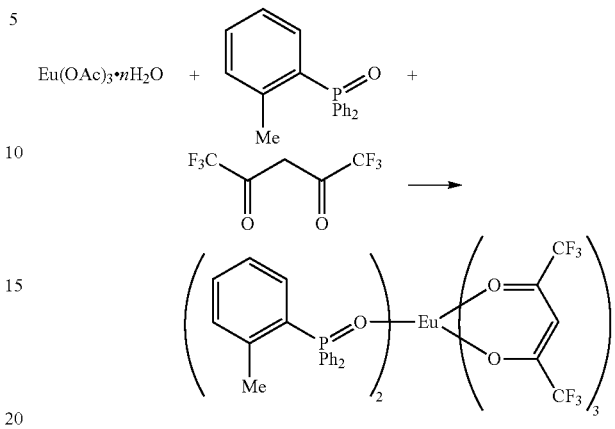

Under argon atmosphere, dichloromethane (3.0 mL) was added to europium (III) acetate hydrate (112 mg, 0.30 mmol as 2.5 hydrate) and diphenyl (o-tolyl) phosphine oxide (175 mg, 0.60 mmol) obtained in Reference Example 26, and [the mixture] was stirred at room temperature for 1 hour. After Hhfa in a 1.8M dichloromethane solution (0.5 mL, 0.90 mmol) was delivered by drops into the reactant mixture, [the obtainment] was stirred at room temperature for 3 hours. The reaction liquid was concentrated under reduced pressure and recrystallized with dichloromethane/hexane, and then, a reddish white solid of bis [diphenyl (o-tolyl) phosphine oxide] tris (hexafluoroacetylacetonato) europium (III) was obtained (yield amount: 315 mg, yield: 77% as 0.30 mmol of europium (III) acetate hydrate was used).

$^{19}$F-NMR (376 MHz, CDCl$_3$), δ (ppm): −79.0 (brs). $^{31}$P-NMR (162 MHz, CDCl$_3$), δ (ppm): −92.7 (brs). ESIMS (m/z): 1150.8 [M-hfa]$^+$.

Example 25

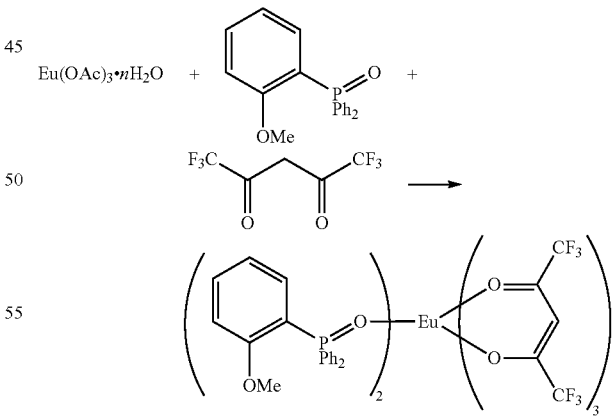

Under argon atmosphere, dichloromethane (3.0 mL) was added to europium (III) acetate hydrate (112 mg, 0.30 mmol as 2.5 hydrate) and diphenyl (2-methoxyphenyl) phosphine oxide (185 mg, 0.60 mmol) obtained in Reference Example 27, and [the mixture] was stirred at room temperature for 1 hour. After Hhfa in a 1.8M dichloromethane solution (0.5 mL, 0.90 mmol) was delivered by drops into the reactant mixture, [the mixture] was stirred at room temperature for 3 hours. The reaction liquid was concentrated under reduced pressure and recrystallized with dichloromethane/hexane, and then, a reddish white solid of bis [diphenyl (2-methoxyphenyl) phosphine oxide] tris (hexafluoroacetylacetonato) europium (III) was obtained (yield amount: 334 mg, yield: 80% as 0.30 mmol of europium (III) acetate hydrate was used).

$^{19}$F-NMR (376 MHz, CDCl$_3$), δ (ppm): −78.9 (brs). $^{31}$P-NMR (162 MHz, CDCl$_3$), δ (ppm): −97.8 (brs). ESIMS (m/z): 1183.1 [M-hfa]$^+$.

Production Example 4

The bis [(2-biphenylyl) diphenylphosphine oxide] tris (hexafluoroacetylacetonato) europium (III) (10 mg) in a toluene solution (1 mL) obtained in Example 17 was added to ethylene-vinyl acetate copolymer resin (manufactured by Tosoh Corporation, Ultrathene 720) (889 mg) in a toluene solution (4 mL). This mixture was stirred at room temperature for 30 minutes, and the obtained viscous liquid was applied onto a surface of a flat quartz glass substrate using a drop casting method, and [the quartz glass substrate] was dried under a condition of 60° C. of temperature for 24 hours, and an optical material containing bis [(2-biphenylyl) diphenylphosphine oxide] tris (hexafluoroacetylacetonato) europium (III) was produced.

Production Example 5

A mixture of a methyl methacrylate monomer (40.1 g, 401 mmol), benzoyl peroxide (0.795 g, 3.3 mmol) as a polymerization initiator and bis [tri (o-tolyl) phosphine oxide] tris (hexafluoroacetylacetonato) europium (III) (39.6 mg, 0.028 mmol) obtained in Example 18 was added to a solution where purified water (203 mL) was added and dissolved into polyvinyl alcohol (2.38 g) as a dispersion stabilizer and sodium nitrite (0.119 g, 1.7 mmol) as a modifier. This mixture was stirred at 65° C. for 4 hours and the obtained white suspension was filtrated, and after this was washed with purified water, [the obtainment] was dried by heating under reduced pressure (80° C., 2 h), and an optical material (38.5 g) containing bis [tri (o-tolyl) phosphine oxide] tris (hexafluoroacetylacetonato) europium (III) was produced.

Comparative Example 3

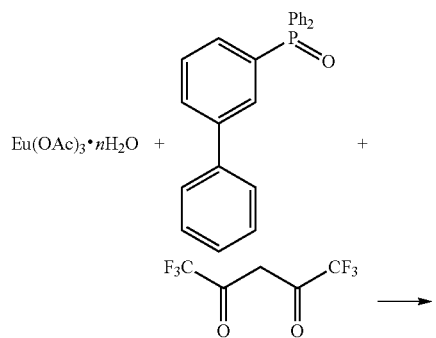

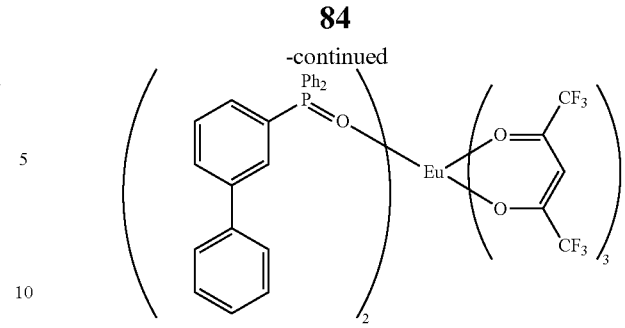

Under argon atmosphere, dichloromethane (3.0 mL) was added to europium (III) acetate hydrate (74.8 mg, 0.200 mmol as 2.5 hydrate) and (3-biphenyl) diphenylphosphine oxide (142 mg, 0.401 mmol) obtained in Reference Example 18, and [the mixture] was stirred at room temperature for 1 hour. After Hhfa in a 1.5M dichloromethane solution (0.40 mL, 0.60 mmol) was delivered by drops into the reactant mixture, [the mixture] was stirred at room temperature for 3 hours. The reaction liquid was concentrated under reduced pressure and was recrystallized with methanol, and then, a white solid of bis [(3-biphenyl) diphenylphosphine oxide] tris (hexafluoroacetylacetonato) europium (III) was obtained (yield amount: 164 mg, yield: 55% as 0.200 mmol of europium (III) acetate hydrate was used).

$^{19}$F-NMR (376 MHz, CDCl$_3$), δ (ppm): −79.0 (brs). $^{31}$P-NMR (162 MHz, CDCl$_3$), δ (ppm): −88.8 (brs). ESIMS (m/z): 1275.6 [M-hfa]$^+$.

Comparative Example 4

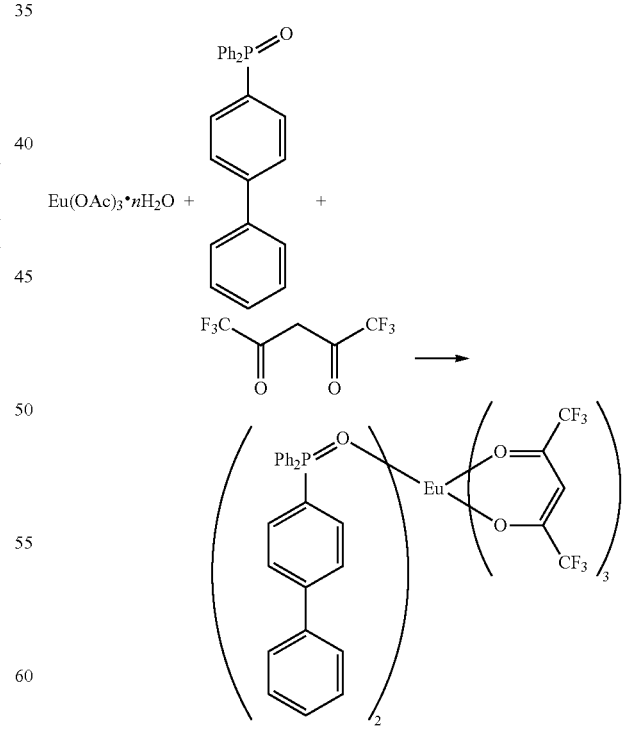

Under argon atmosphere, dichloromethane (8.0 mL) was added to europium (III) acetate hydrate (180 mg, 0.481 mmol, as 2.5 hydrate) and (4-biphenyl) diphenylphosphine oxide (344 mg, 0.971 mmol) obtained in Reference Example 19, and [the mixture] was stirred at room temperature for 1 hour. After Hhfa in a 1.5M dichloromethane solution (0.96 mL, 1.44 mmol) was delivered by drops into the reactant mixture, [the obtainment] was stirred at room temperature for 3 hours. The reaction liquid was filtrated, and the filtrate was concentrated under reduced pressure and recrystallized with methanol, and then, a reddish white solid of bis [(4-biphenyl) diphenylphosphine oxide] tris (hexafluoroacetylacetonato) europium (III) was obtained (yield amount: 465 mg, yield: 65% as 0.480 mmol of europium (III) acetate hydrate was used).

$^{19}$F-NMR (376 MHz, CDCl$_3$), δ (ppm): −78.9 (brs). $^{31}$P-NMR (162 MHz, CDCl$_3$), δ (ppm): −91.2 (brs). ESIMS (m/z): 1275.5 [M-hfa]$^+$.

Evaluation Example

Samples for emission spectral measurement and light resistance of europium complexes were produced by crushing powder of europium complexes obtained in Examples 17 to 24 and Comparative Examples 1, 3 and 4 in mortars to be fine powder, and by filling the powder into powder cells (manufactured by JASCO Corporation, PSH-002) under dry air atmosphere.

Measurement results of emission spectrum (380 nm of excitation light) of the europium complexes obtained in Examples 17 to 25 are shown in FIGS. 33 to 41, respectively, and a measurement result of emission spectrum (340 nm of excitation light) of an optical material containing the europium complex of the present invention obtained in Production Example 4 is shown in FIG. 42. A measurement result of emission spectrum (320 nm of excitation light) of an optical material containing the europium complex of the present invention obtained in Production Example 5 is shown in FIG. 43. Emission of lights at approximately 593 nm, 612 nm, 653 nm and 699 nm based upon f-f electronic transition, which is characteristic in Eu (III) complex(es), was observed.

Evaluation results of luminescent quantum yield at wavelength 380 nm of the excitation light of the europium complexes obtained in Examples 17 to 25 are shown in Table 3.

TABLE 3

| Sample | Luminescent quantum yield (%) |
|---|---|
| Example 17 | 66% |
| Example 18 | 56% |
| Example 19 | 69% |
| Example 20 | 67% |
| Example 21 | 57% |
| Example 22 | 78% |
| Example 23 | 48% |
| Example 24 | 75% |
| Example 25 | 78% |

The light resistance was evaluated by a method indicated below.

For the light resistance evaluation of Examples 17 to 25 and Comparative Examples 1, 3 and 4, the intensity of emission at the maximum emission wavelength in the vicinity of 615 nm was measured with a spectrophotometer (manufactured by JASCO Corporation, FP-6500), respectively. Measurement conditions were 5 nm of a slit at the excitation side, 5 nm of a slit at a fluorescence side and 380 nm of excitation light wavelength. Next, at room temperature, an ultraviolet light at 200 mW/cm$^2$ (365 nm) was irradiated for a predetermined time period (0 to 24 hours) using an ultraviolet light irradiator (manufactured by Ushio Inc, SP-9) and lenses. The intensity of emission of the samples after the irradiation of ultraviolet light was measured again with the spectrophotometer, and residual ratios of the intensity of emission from the initial state were calculated in accordance with the expression below, and the light resistance was evaluated by setting the ultraviolet light irradiation time at the X axis and setting the residual ratio of the intensity of emission at the Y axis.

Residual ratio of intensity of emission (%)($I/I_0$)= (intensity of emission at maximum emission wavelength after irradiation of ultraviolet rays)/ (intensity of emission at maximum emission wavelength before irradiation of ultraviolet rays)×100

Evaluation results of the light resistance of the europium complexes obtained in Comparative Examples 1, 3 and 4 were shown in FIG. 44, and evaluation results of the light resistance of the europium complexes of the present invention obtained in Examples 17 to 25 were shown in FIGS. 45 to 53, respectively, and results of the residual ratios of the intensity of emission after 24 hours of irradiation of ultraviolet light obtained as a result were shown in Table 4.

TABLE 4

| Sample | Residual ratio of intensity of emission (%) |
|---|---|
| Example 17 | 95% |
| Example 18 | 95% |
| Example 19 | 98% |
| Example 20 | >99% |
| Example 21 | 96% |
| Example 22 | >99% |
| Example 23 | 88% |
| Example 24 | 93% |
| Example 25 | 96% |
| Comparative Example 1 | 46% |
| Comparative Example 3 | 35% |
| Comparative Example 4 | 48% |

As shown in FIGS. 45 to 53, It has been found that the europium complex of the present invention, which has a specific substituent at the ortho position of the phenyl group on the phosphorus atom of the phosphine oxide, is hard to reduce the emission intensity by ultraviolet ray irradiation, and has excellent light resistance.

In the meantime, a decrease in the intensity of emission was great in the compound (Comparative Example 1) specifically described in RUB1453869 and JP-A-2003-81986, and a decrease in the intensity of emission was great in a compound having specific substituents at a meta position (Comparative Example 3) and at a para position (Comparative Example 4) of the phenyl group on a phosphorus atom of phosphine oxide.

INDUSTRIAL APPLICABILITY

The europium complexes of the present invention will not attenuate the intensity of emission and have high photostability even after irradiation of lights for a long time compared to europium complexes having triphenylphosphine oxide and europium complexes having a linear alkyl group on a phosphorus atom. Further, the europium complexes of the present invention also show high solubility, and it is easy to be dissolved into organic solvents, polymer materials or the like, and these are uniformly dispersible. Consequently, the europium complexes of the present invention are useful as emitting materials, such as films for photovoltaic, agricultural films, LED fluorescent bodies or security ink, and wavelength conversion materials to be used for those.

Furthermore, all contents in specifications, patent claims, drawings and abstracts of Japanese Patent Applications 2017-227187 filed on Nov. 27, 2017 and 2018-52956 filed on Mar. 20, 2018 are cited herein, and incorporated as disclosures of the specification of the present invention.

What is claimed is:

1. A europium complex expressed with the following formula (A):

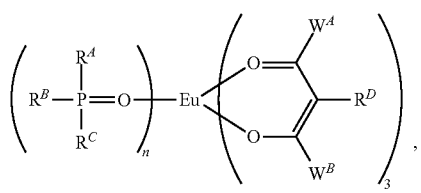

(A)

wherein $R^A$ and $R^B$ independently represent a cyclic alkyl group with 3 to 10 carbons, respectively, and $R^C$ is a cyclic alkyl group with 3 to 10 carbons, or a phenyl group expressed with the formula (B):

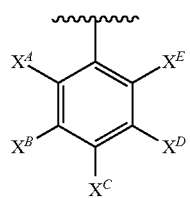

(B)

wherein $X^A$, $X^B$, $X^C$, $X^D$ and $X^E$ independently represent a hydrogen atom, a fluorine atom, an alkyl group with 1 to 3 carbons, an alkyloxy group with 1 to 3 carbons, an aryloxy group with 6 to 10 carbons, a fluoroalkyl group with 1 to 3 carbons, a fluoroalkyloxy group with 1 to 3 carbons, or a phenyl group that may be substituted with a fluorine atom, an alkyl group with 1 to 3 carbons, an alkyloxy group with 1 to 3 carbons, a fluoroalkyl group with 1 to 3 carbons, a fluoroalkyloxy group with 1 to 3 carbons, a fluorophenyl group, a hydroxyl group or a cyano group, respectively, or wherein $R^A$ is cyclic alkyl group with 3 to 10 carbons, $R^B$ and $R^C$ are a phenyl group expressed with the formula (B), provided, however, that a case where $R^A$ is a cyclohexyl group, and, $R^B$ and $R^C$ are a phenyl group is excluded; or wherein $R^A$, $R^B$ and $R^c$ are independently an ortho-substituted phenyl group expressed with the formula (Ba):

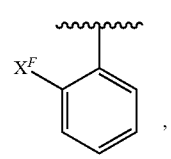

(Ba)

wherein $X^F$ represents a hydrogen atom, an alkyl group with 1 to 3 carbons, an alkyloxy group with 1 to 3 carbons, a fluoroalkyl group with 1 to 3 carbons, a fluoroalkyloxy group with 1 to 3 carbons, a naphthyl group that may be substituted with a fluorine atom, a pyridyl group that may be substituted with a fluorine atom, or a phenyl group expressed with the formula (C):

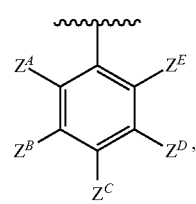

(C)

wherein $Z^A$, $Z^C$ and $Z^E$ independently represent a hydrogen atom, a fluorine atom, an alkyl group with 1 to 3 carbons, an alkyloxy group with 1 to 3 carbons, an aryloxy group with 6 to 10 carbons, a fluoroalkyl group with 1 to 3 carbons, a fluoroalkyloxy group with 1 to 3 carbons, a phenyl group that may be substituted with a fluorine atom, a hydroxyl group or a cyano group, respectively;

wherein $Z^B$ and $Z^D$ are independently a hydrogen atom or fluorine atom, respectively, provided, however that a case where $R^A$, $R^B$ and $R^C$ are all a phenyl group is excluded;

wherein $R^D$ represents a hydrogen atom, a deuterium atom or a fluorine atom;

wherein $W^A$ and $W^B$ independently an alkyl group with 1 to 6 carbons, a fluoroalkyl group with 1 to 6 carbons, a phenyl group, a 2-thienyl group or a 3-thienyl group, respectively; and wherein n represents an integer of 1 to 3.

2. The europium complex according to claim 1 expressed with the following formula (1):

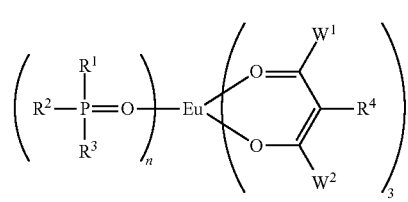

(1)

wherein $R^1$ and $R^2$ independently represent a cyclic alkyl group with 3 to 10 carbons, respectively;

wherein $R^3$ represents a cyclic alkyl group with 3 to 10 carbons or a phenyl group expressed with a formula (2a):

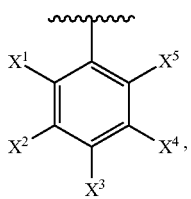

(2a)

(wherein $X^1$, $X^2$, $X^3$, $X^4$ and $X^5$ independently represent a hydrogen atom; a fluorine atom, an alkyl group with 1 to 3 carbons, an alkyloxy group with 1 to 3 carbons, an aryloxy group with 6 to 10 a carbons, a fluoroalkyl group with 1 to 3 a carbons, a fluoroalkyloxy group with 1 to 3 carbons, or a phenyl group that may be substituted with a fluorine atom, an alkyl group with 1 to 3 carbons, an alkyloxy group with 1 to 3 a carbons, a fluoroalkyl group with 1 to 3 a carbons, a fluoroalkyloxy group with 1 to 3 carbons, a fluorophenyl group, a hydroxyl group or a cyano group, respectively;

wherein $R^4$ represents a hydrogen atom, a deuterium atom or a fluorine atom;

wherein $W^1$ and $W^2$ independently represent an alkyl group with 1 to 6 a carbons, a fluoroalkyl group with 1 to 6 carbons, a phenyl group, a 2-thienyl group, or a 3-thienyl group, respectively; and wherein n represents an integer of 1 to 3.

3. The europium complex according to claim 1, wherein in the formula (1), $R^3$ is a cyclic alkyl group with 3 to 10 carbons.

4. The europium complex according to claim 1, wherein in the formula (1), $R^1$, $R^2$ and $R^3$ are a cyclohexyl group.

5. The europium complex according to claim 1, wherein in the formula (1), n is 2.

6. The europium complex according to claim 1, wherein in the formula (1), $W^1$ and $W^2$ are independently a fluoroalkyl group with 1 to 6 carbons, respectively.

7. A europium complex according to claim 1 expressed with the following formula (1):

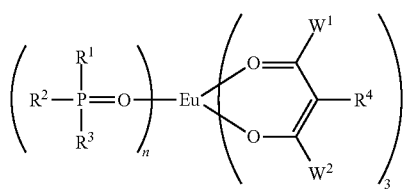

(1)

wherein $R^1$ is a cyclic alkyl group with 3 to 10 carbons;
wherein $R^2$ and $R^3$ represent a phenyl group expressed with the following formula (2a):

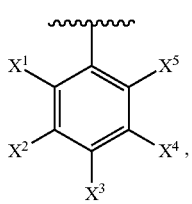

(2a)

(wherein $X^1$, $X^2$, $X^3$, $X^4$ and $X^5$ independently represent a hydrogen atom, a fluorine atom, an alkyl group with 1 to 3 carbons, an alkyloxy group with 1 to 3 carbons, an aryloxy group with 6 to 10 carbons, a fluoroalkyl group with 1 to 3 carbons, a fluoroalkyloxy group with 1 to 3 carbons, or a phenyl group that may be substituted with a fluorine atom, an alkyl group with 1 to 3 carbons, an alkyloxy group with 1 to 3 carbons, a fluoroalkyl group with 1 to 3 carbons, a fluoroalkyloxy group with 1 to 3 carbons, a fluorophenyl group, a hydroxyl group, or a cyano group, respectively, provided, in a case where $R^1$ is a cyclohexyl group, and, $R^2$ and $R^3$ are a phenyl group is excluded;

wherein $R^4$ represents a hydrogen atom, a deuterium atom or a fluorine atom;

wherein $W^1$ and $W^2$ independently represent an alkyl group with 1 to 6 carbons, a fluoroalkyl group with 1 to 6 a carbons, a phenyl group, a 2-thienyl group, or a 3-thienyl group, respectively; and wherein n represents an integer of 1 to 3.

8. The europium complex according to claim 1, wherein in the formula (1), $R^1$ is a cyclohexyl group.

9. The europium complex according to claim 1, wherein in the formula (1), n is 2.

10. The europium complex according to claim 1, wherein in the formula (1), $W^1$ and $W^2$ are independently a fluoroalkyl group with 1 to 6 carbons, respectively.

11. The europium complex according to claim 1, wherein in the formula (1), $R^4$ is a hydrogen atom.

12. The europium complex according to claim 1, wherein in the formula (2a), $X^1$, $X^2$ and $X^3$ are independently a hydrogen atom, a methyl group, or a phenyl group expressed with the following formula (2b), respectively, and $X^4$ and $X^5$ is independently a hydrogen atom or a methyl group, respectively,

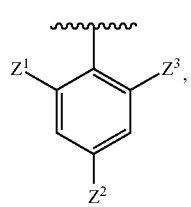

(2b)

wherein $Z^1$, $Z^2$ and $Z^3$ are independently a hydrogen atom, a fluorine atom, an alkyl group with 1 to 3 carbons, an alkyloxy group with 1 to 3 carbons, an aryloxy group with 6 to 10 carbons, a fluoroalkyl group with 1 to 3 carbons, a fluoroalkyloxy group with 1 to 3 carbons, or a phenyl group that may be substituted with a fluorine atom, respectively.

13. The europium complex according to claim 1, wherein in the formula (1), $R^4$ is a hydrogen atom.

14. The europium complex according to claim 1, wherein in the formula (2a), $X^1$, $X^2$ and $X^3$ are independently a hydrogen atom, a methyl group, or a phenyl group expressed with the formula (2b), respectively; and $X^4$ and $X^5$ independently a hydrogen atom or a methyl group, respectively,

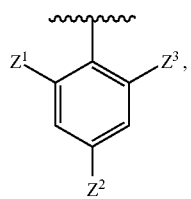

(2b)

wherein $Z^1$, $Z^2$ and $Z^3$ are independently a hydrogen atom, a fluorine atom, an alkyl group with 1 to 3 carbons, an alkyloxy group with 1 to 3 carbons, an aryloxy group with 6 to 10 carbons, a fluoroalkyl group with 1 to 3 carbons, a fluoroalkyloxy group with 1 to 3 carbons or, a phenyl group that may be substituted with a fluorine atom, respectively.

15. The europium complex according to claim 1, wherein the europium complex is a compound selected from the group consisting of compounds (1-1) to (1-11) and (1-19) to (1-21):

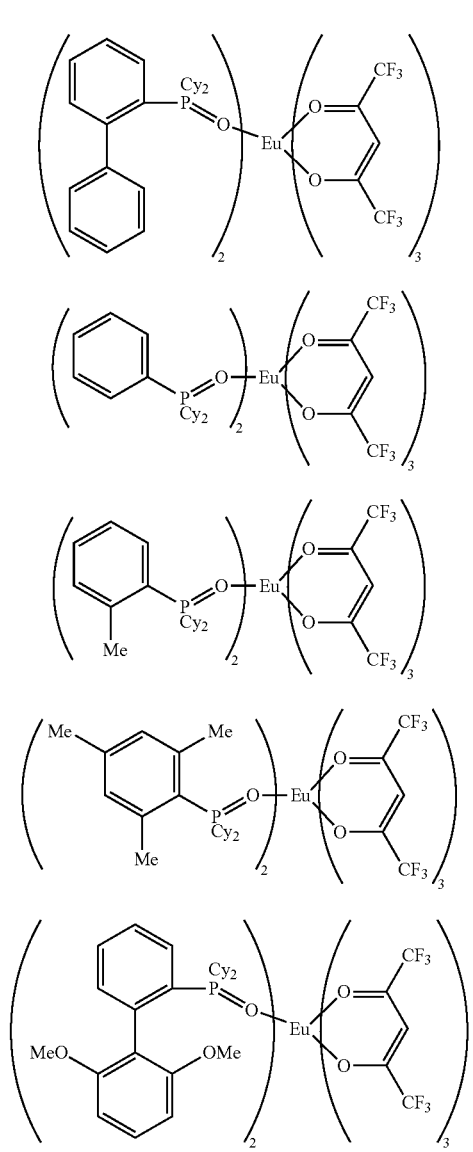

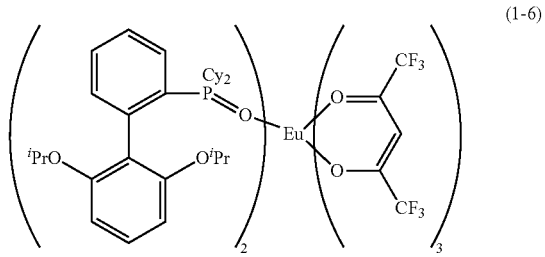

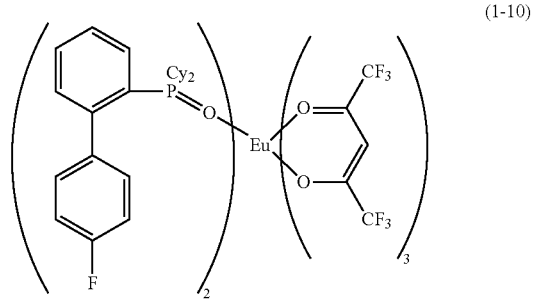

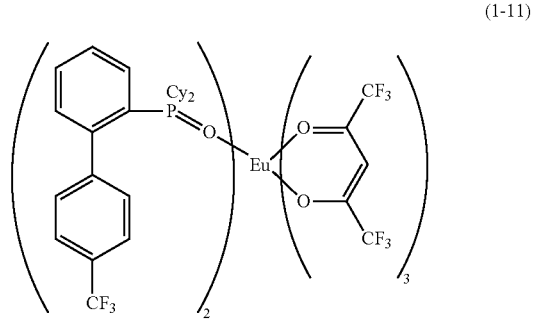

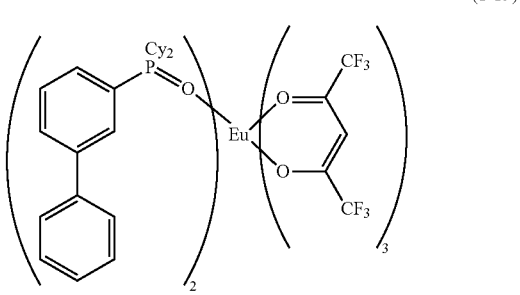

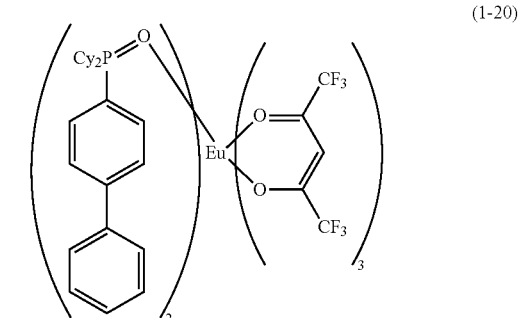

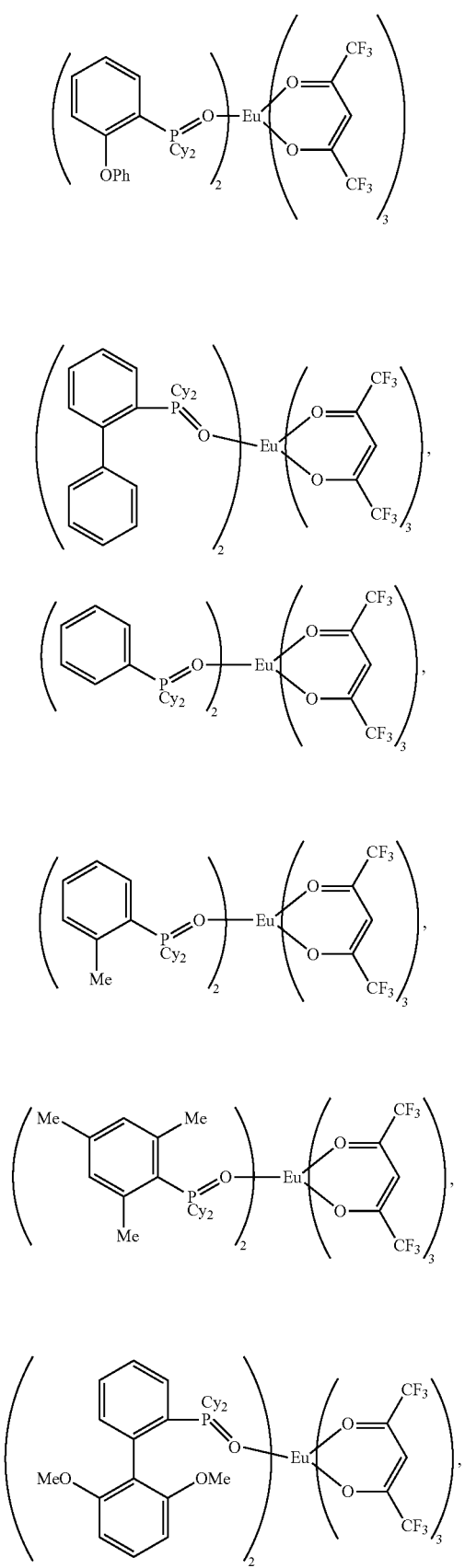
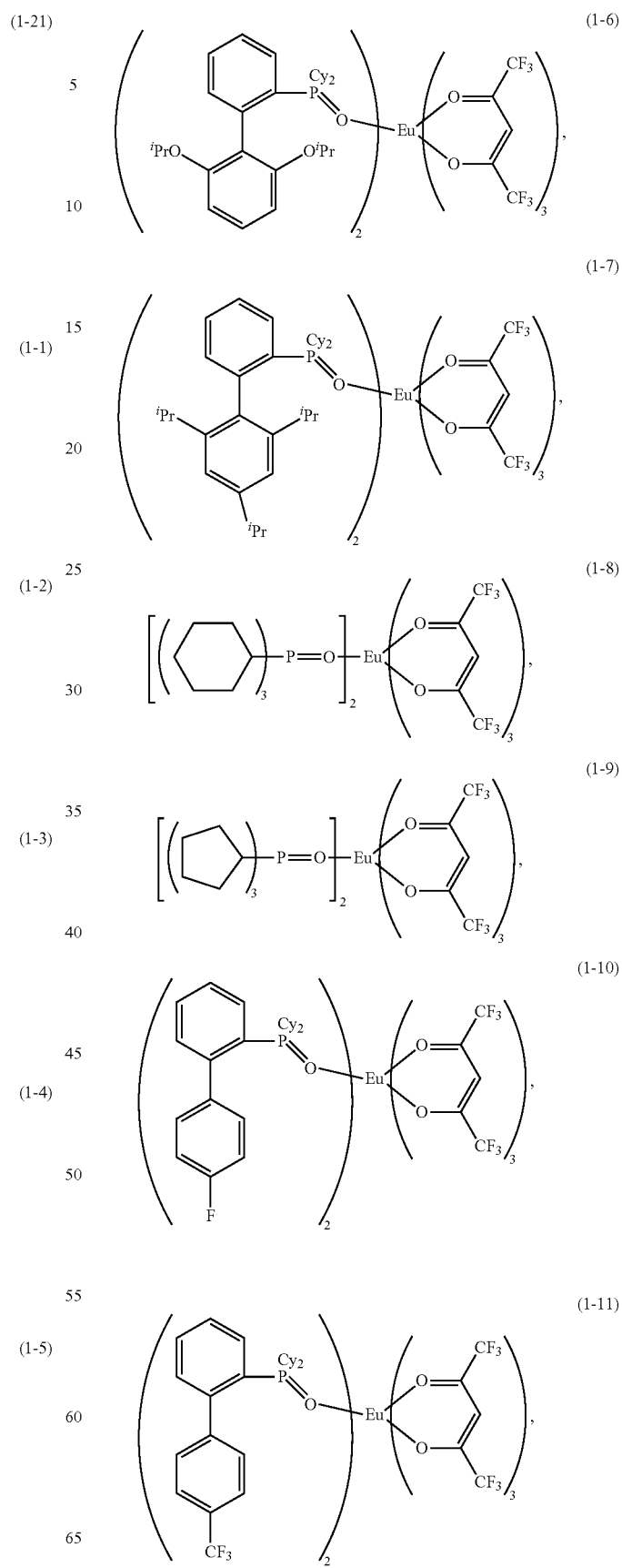

-continued

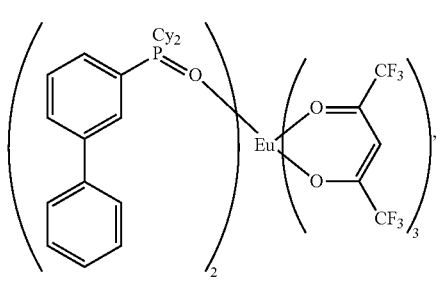
(1-19)

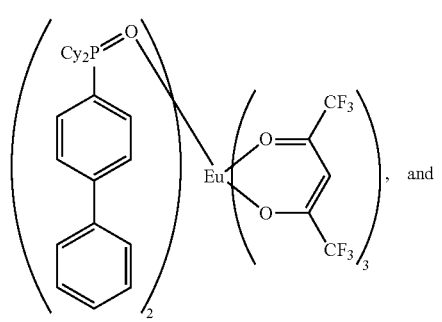
(1-20)

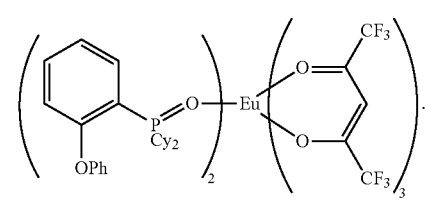
(1-21)

16. The europium complex according to claim 1 expressed with the following formula (6):

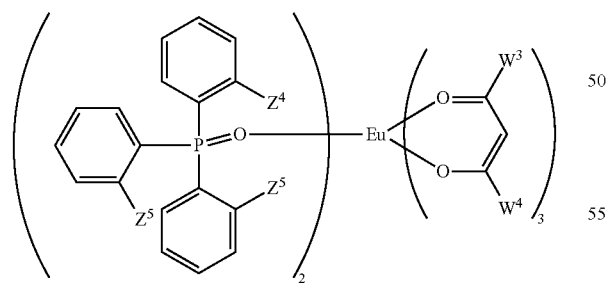
(6)

wherein $Z^4$, $Z^5$ and $Z^6$ independently represent a hydrogen atom, an alkyl group with 1 to 3 carbons, an alkyloxy group with 1 to 3 carbons, a fluoroalkyl group with 1 to 3 carbons, a fluoroalkyloxy group with 1 to 3 carbons, a naphthyl group that may be substituted with a fluorine atom, a pyridyl group that may be substituted with a fluorine atom or group expressed with the formula (7):

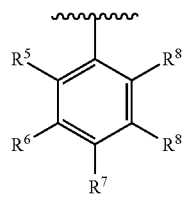
(7)

wherein $R^5$, $R^7$ and $R^9$ independently represent a hydrogen atom, a fluorine atom, an alkyl group with 1 to 3 carbons, an alkyloxy group with 1 to 3 carbons, a fluoroalkyl group with 1 to 3 carbons, a fluoroalkyloxy group with 1 to 3 carbons, a phenyl group that may be substituted with a fluorine atom, a hydroxyl group, or a cyano group, respectively;

$R^6$ and $R^8$ independently represent a hydrogen atom or a fluorine atom, respectively, provided, however, that a case where $Z^4$, $Z^5$ and $Z^6$ cannot be a hydrogen atom at the same time; and $W^3$ and $W^4$ independently represent an alkyl group with 1 to 6 carbons, a fluoroalkyl group with 1 to 6 carbons, a phenyl group, a 2-thienyl group or a 3-thienyl group, respectively.

17. The europium complex according to claim 1, wherein $W^3$ and $W^4$ are independently a fluoroalkyl group with 1 to 6 carbons, respectively.

18. The europium complex according to claim 1, wherein $Z^4$, $Z^5$ and $Z^6$ are independently a hydrogen atom, a methyl group, a methyloxy group, or a group expressed with the formula (7), respectively; and in the formula (7), $R^5$, $R^7$ and $R^9$ are independently a hydrogen atom, a fluorine atom, an alkyl group with 1 to 3 carbons, an alkyloxy group with 1 to 3 carbons a fluoroalkyl group with 1 to 3 carbons, a fluoroalkyloxy group with 1 to 3 carbons, or a phenyl group, respectively; and $R^6$ and $R^8$ are a hydrogen atom.

19. The europium complex according to claim 1, wherein the formula (6) is a compound selected from the group consisting of compounds (6-1) to (6-7), (6-22), and (6-23):

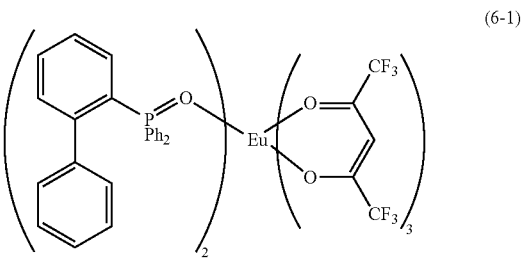
(6-1)

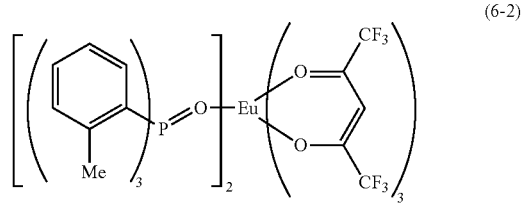
(6-2)

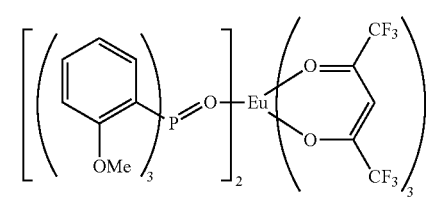
(6-3)
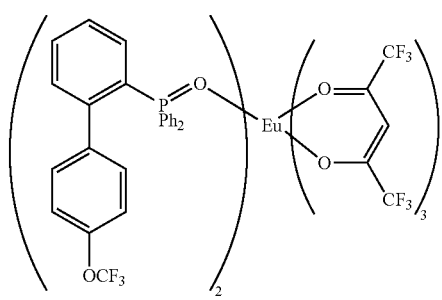
(6-7)
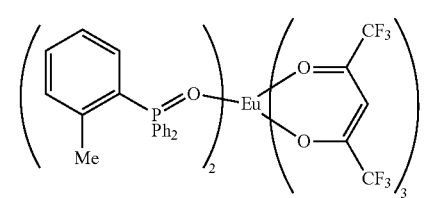
(6-22)
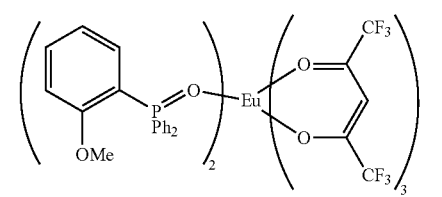
(6-23)
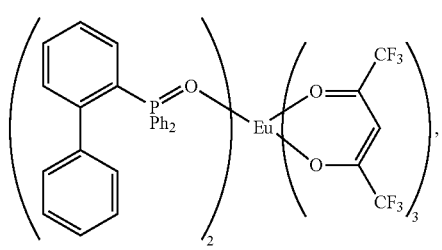
(6-1)
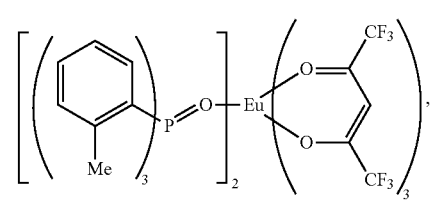
(6-2)
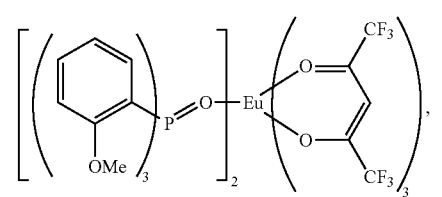
(6-3)
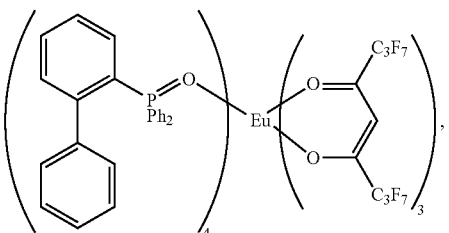
(6-4)
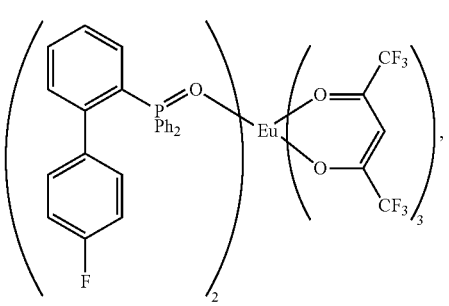
(6-5)
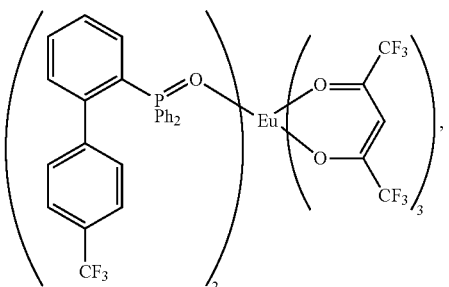
(6-6)
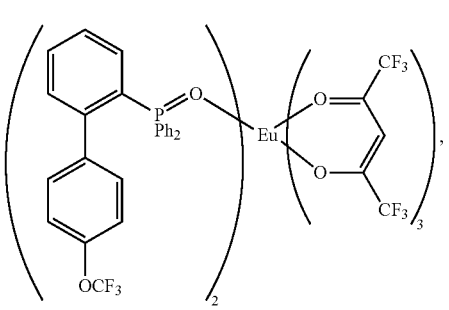
(6-7)
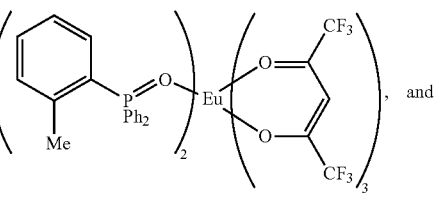
, and
(6-22)
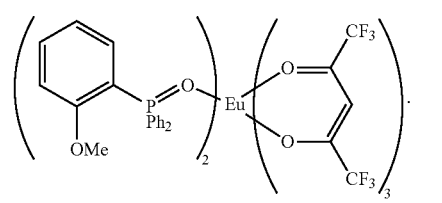
.
(6-23)
* * * * *